US006277635B1

(12) United States Patent
Roncarolo et al.

(10) Patent No.: US 6,277,635 B1
(45) Date of Patent: Aug. 21, 2001

(54) USE OF INTERLEUKIN-10 TO PRODUCE A POPULATION OF SUPPRESSOR CELLS

(75) Inventors: Maria-Grazia Roncarolo, Los Altos; Rene de Waal Malefyt, Sunnyvale, both of CA (US); Rosa Bacchetta, Milano Due (IT); Herve M. Groux, Palo Alto; Jan E. de Vries, Los Altos, both of CA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 08/643,810

(22) Filed: May 6, 1996

Related U.S. Application Data

(63) Continuation-in-part of application No. 07/846,208, filed on Mar. 4, 1992, now abandoned.

(51) Int. Cl.$^7$ .................................................. C12N 5/08
(52) U.S. Cl. ...................... 435/372.3; 435/325; 435/366; 435/372
(58) Field of Search .................................. 435/325, 366, 435/372, 372.3

(56) References Cited

U.S. PATENT DOCUMENTS

| 4,483,920 | 11/1984 | Gillespie et al. | 435/6 |
|---|---|---|---|
| 4,559,310 | 12/1985 | Cantor et al. | 436/519 |

FOREIGN PATENT DOCUMENTS

EP 405 980   2/1991 (EP) .............................. C12N/15/24

OTHER PUBLICATIONS

Becker, J.C. et al., *International Immunology*, 6 (10) : 1605–12, 1994.*
Becker, J.C., et al. 1993 *International Immunology* vol. 5, No. 12, pp. 1501–1508 Tumor escape mechanisms from immunosurveillance: induction of unresponsiveness in a specific MHC–restricted CD4+human T cell clone by the autologous MHC class II+melanoma.
Enk, Alexander H., et al. *J. Exp. Med.* vol. 179 Apr. 1994 Induction of Hapten–specific Tolerance by Interleukin 10 In Vivo.
Fabiola Cardillo, et al., *Eur. J. Immunol.*, 23:2597–2605, 1993. "An age–related γ§T cell supressor activity correlates with the outcome of autoimmunity in experimental *Trypanosoma cruzi* infection"
S. Knaan–Shanzer, et al., *Cellular Immunology*, 151:196–217, 1993. "Occurance of a Soluble nonspecific Suppressor Factor in the Serum Early after Birth."
Rolf Weimer, et al., Transplantation, 62(11):1606–1614, Dec. 15, 1996. "Pretransplant CD4 Helper Function and Interleukin 10 Response Predict Risk of Acute Kidney Graft Rejection"

Daniel M. Altman, et al., "Cotransfection of ICAM–1 and HLA–DR Reconstitutes Human Antigen–Presenting Cell Function in Mouse L Cells," *Nature* 338:512–514, Apr. 1989.
Michel Arock, et al., "Interleukin–10 Inhibits Cytokine Generation from Mast Cells," *Eur. J. Immunol.* 26:166–170, 1996.
Rosa Bacchetta, et al., "Host–Reactive CD4+ and CD8+ T Cell Clones Isolated from a Human Chimera Produce IL–5, IL–2, IFN–γ, and Granulocyte Macrophage Colony Stimulating Factor but Not IL–5," *J. Immunol.* 144:902–908, Feb. 1990.
Maria–Teresa Bejarano, et al., "Effect of Cyclosporin–A (CsA) on the Ability of T Lymphocytes Subsets to Inhibit the Proliferation of Autologous EBV–Transformed B Cells," *Int. J. Cancer* 35:327–333, 1985.
Maria–Teresa Bejarano, et al., "Interleukin 10 Inhibits Allogeneic Proliferative and Cytotoxic T Cell Responses Generated in Primary Mixed Lymphocyte Cultures," *Intl. Immunol.* 4:1389–1397, Sep. 1992.
Michael Bevan, "High Determinant Density May Explain the Phenomenon of Alloreactivity," *Immunol. Today* 5:128–130, 1984.
Andrew C. Chan et al., "The Role of Protein Tyrosine Kinases and Protein Tyrosine Phosphatases in T Cell Antigen Receptor Signal Transduction," *Ann. Rev. Immunol.* 12:555–592, 1994.
F.Q. Cunha, et al., "Interleukin–10 (IL–10) Inhibits the Induction of Nitric Oxide Synthetase by Interferon–γ in Murine Macrophages," *Biochem. Biophys. Res. Comm.* 182:1155–1159, Feb. 1992.
Annalisa D'Andrea, et al., "Interleukin 10 (IL–10) Inhibits Human Lymphocyte Interferon–g Production by Suppressing Natural Killer Cell Stimulatory Factor/IL–12 Sythesis in Accessory Cells," *J. Exp. Med.* 178:1041–1048, Sep. 1993.
Jan E. de Vries, et al., eds., *Interleukin–10*, R.G. Landes Co., Austin, Tx, title page, verso, and table of contents, 1995.
René de Waal Malefyt, et al., "Interleukin 10 (IL–10) and Viral IL–10 Strongly Reduce Antigen–specific Human T Cell Proliferation by Diminishing the Antigen–presenting Capacity of Monocytes via Downregulation of Class II Major Histocompatibility Complex Expression," *J. Exp. Med.* 174:915–924, Oct. 1991.
Rene de Waal Malefyt, et al., "Interleukin 10 (IL–10) Inhibits Cytokine Synthesis by Human Monocytes: An Autoregulatory Role of IL–10 Produced by Monocytes," *J. Exp. Med.* 174:1209–1220, Nov. 1991.

(List continued on next page.)

*Primary Examiner*—Marianne P. Allen
(74) *Attorney, Agent, or Firm*—Hugh Wang; Edwin P. Ching; Ted Apple

(57) ABSTRACT

Interleukin-10 for producing a population of cells which are capable of inhibiting or suppressing reactions to alloantigens, for example in graft-versus-host disease or tissue rejection, is described. Interleukin-10 for reducing responses in mixed lymphocyte response (MLR) is also described. Exogenous or induced endogenous IL-10 may be used for the inhibition or suppression of the reactions to alloantigens.

17 Claims, 20 Drawing Sheets

OTHER PUBLICATIONS

David F. Fiorentino, et al., "Two Types of Mouse T Helper Cell: IV. Th2 Clones Secrete a Factor that Inhibits Cytokine Production by Th1 Clones," *J. Exp. Med.* 170:2081–2095, Dec. 1989.

David F. Fiorentino, et al, "IL–10 Acts on the Antigen–Presenting Cell to Inhibit Cytokine Production by Th1 Cells," *J. Immunol.* 146:3444–3451, May 1991.

David F. Fiorentino, et al., "IL–10 Inhibits Cytokine Production by Activated Macrophages," *J. Immunol.* 147:3815–3822, Dec. 1991.

Stephen J. Forman, et al., *Bone Marrow Transplantation*, Blackwell Scientific Publications, Cambridge, MA, Chapter 4, verso and pp. 37–38, 1994.

James D. Fraser, et al., "Signal Transduction Events Leading to T–Cell Lymphokine Gene Expression," *Immunol. Today* 14:357–362, 1993.

Arnold S. Freedman, et al., "B7, a B Cell–Restricted Antigen that Identifies Preactivated B Cells," *J. Immunol.* 139:3260–3267, Nov. 1987.

Ricardo T. Gazzinelli, et al., "IL–10 Inhibits Parasite Killing and Nitrogen Oxide Production by IFN–γ–Activated Macrophges," *J. Immunol.* 148:1792–1796, 1992.

Ning Fei Go, et al., "Interleukin 10, a Novel B Cell Stimulatory Factor: Unresponsiveness of X Chromosome–Linked Immunodeficiency B Cells," *J. Exp. Med.* 172:1625–1631, Dec. 1990.

Clifford V. Harding, et al., "Functional and Ultrastructrual Evidence for Intracellular Formation of Major Histocmpatibility Complex Class II–Peptide Complexes during Antigen Processing," *Proc. Natl. Acad Sci.* 87:5553–5557, Jul. 1990.

Chyi–Song Hseih, et al., "Development of Th1 CD4+T Cells through IL–12 Produced by *Listeria* –Induced Macrophages," *Science* 260:547–549, Apr. 1993.

Di–Hwei Hsu, et al., "Expression of Interleukin–10 Activity by Epstein–Barr Virus Protein BCRFI," *Science*, 250:830–832, Nov. 1990.

Keven W. Moore, et al., "Homology of Cytokine Synthesis Inhibitory Factor (IL–10) to the Epstein–Barr Virus Gene BCRFI," *Science* 248:1230–1234, Jun. 1990.

Hiroaki Niiro, et al., "IL–10 Inhibits Prostaglandin E2 Production by Lypopolysaccharide–Stimulated Monocytes," *Intl. Immunol.* 6:661–664, 1994.

William E. Paul, ed., *Fundamental Immunology*, 2nd ed., Raven Press, NY, title page, verso, Chapter 1 pp. 15–16, 1989.

Han–Jurgen Rode, et al., "The Genome of Equine Herpesvirus Type 2 Harbors an Interleukin 10 (IL–10) –Like Gene," *Virus Genes* 7:111–116, 1993.

Maria–Grazia Roncarolo, et al., "T Cell Repertoire and Tolerance After Fetal Stem Cell Transplantation," *Bone Marrow Transplantation: Proceedings of Fetal and Neonatal Cell Transplantation and Retroviral Gene Therapy*, vol. 9, Supp. 1:127–128, 1992.

Maria–Grazia Roncarolo, et al., "SCID Patients Reconstituted by Fetal Liver Stem Cells: Possible Role of IL–10 in Transplantation Tolerance," *Journal of Cellular Biochemistry*, supp. 16A:214, 1992.

Hergen Spits, et al., "Functional Characterization of Human IL–10," *Int. Arch. Allergy Immunol.* 99:8–15, 1992.

Shingo Takanaski, et al., "Interleukin 10 Inhibits Lipopolysaccharide–Induced Survival and Cytokine Production by Human Peripheral Blood Eosinophils," *J. Exp. Med.* 180:711–715, Aug. 1994.

Bart A. E. Vandekerckhhove, et al., "Human Hematopoietic Cells and Thymic Epithelial Cells Induce Tolerance via Different Mechanisms in the SCID–hu Mouse Thymus," *J. Exp. Med.* 175:1033–1043, Apr. 1992.

P. Vieira, et al., "Isolation and Expression of Human Cytokine Synthesis Inhibitory Factor cDNA Clones: Homology to Epstein–Barr Virus Open reading Frame BCRFI," *Proc. Natl. Acad. Sci.* 88:1172–1176, Feb. 1991.

Hervé Groux, et al., *9th International Congress of immunology*, p. 604, Abstract 3582, San Francisco, CA, Jul. 23–29, 1995. "IL–10 Induces Antigen–Specific Anergy in Human Peripheral Blood CD4+ Cells".

Hervé Groux, et al., *FASEB Journal*, 10(6):A1027, Abstract 162, Apr. 30, 1996. "IL–10 Induces a Long Term Antigen–Specific State in Human CD4+ T Cells".

Fiona Powrie, et al., *Journal of Experimental Medicine*179:589–600, Feb. 1994. "Regulatory Interactions between CD45RB$^{high}$ and CD45RB$^{low}$ CD4+ T Cells Are Important for the Balance between Protective and Pathogenic Cell–mediated Immunity".

Dominique Schols, et al., *Journal of Immunology*, 154:3204–3212, 1995. "Unique Cytokine Production Profile of Anergic Human T Cells in SCID–hu Mice After Staphylococcal Enterotoxin B Administration".

H. L. Weiner, et al., *FASEB Journal*, 10(6):A1444, Abstract 2558, Apr. 30, 1996. "Induction and Characterization of TGF–BETA Secreting TH3 Cells".

Rosa Bacchetta, et al., "High Levels of Interleukin 10 Production In Vivo Are Associated with Tolerance in SCID Patients Transplanted with HLA Mismatched Hematopoietic Stem Cells," *J. Exp. Med.* 179 : 493–502, Feb. 1994.

Rosa Bacchetta, et al., "Chimerism and Tolerance to Host and Donor in Severe Combined Immunnodeficiencies Transplanted with Fetal Liver Stem Cells," *J. Clin. Invest.* 91:1067–1078, Mar. 1993.

Avilnash Bhandoola, et al., "Reduced CD3–Mediated Protein Tyrosine Phosphorylation in Anergic CD4+ and CD8+ T Cells," *J. Immunol.* 151:2355–2367, Sep. 1, 1993.

Vassiliki A. Boussiotis, et al., CD2 Is Involved in Maintenance and Reversal of Human Alloantigen–specific Clonal Anergy, *J. Exp. Med.* 180:1665–1673, Nov. 1994.

Christophe Caux, et al., "Interleukin 1 Inhibits T Cell Alloreaction Induced by Human Dendritic Cells," *Int'l. Immunol.* 6:1177–1185, 1994.

Chung–Hsing Chang, et al., "B7–1 Expression of Langerhans Cells is Up–Regulated by Proinfalmmatory Cytokines, and Is Down–Regulated by Interferon–γ or by Interleukin–10," *Eur. J. Immunol.* 25:394–398, 1995.

Youchai Chen, et al., "Regulatory T Cell Clones Induced by Oral Toerance: Suppression of Autoimmune Encephalomyelitis," *Science* 265:1237–1240, Aug. 26, 1995.

Youchai Chen, et al., "Peripheral Deletion of Antigen–Reactive T Cells in Oral Tolerance," *Nature*, 376:177–180, Jul. 13, 1995.

Dimuthu R. DeSilva, et al., "Clonal Anergy Is Induced In Vitro by T Cell Receptor Occupancy in the Absence of Proliferation," *J. Immunol.* 147:3261–3267, Nov. 15, 1991.

Rene de Waal Malefyt, et al., "Direct Effect of IL–10 on Subsets of Human CD4+ T Cell Clones and Resting T Cells," *J. Immunol.* 150:4754–4765, Jun. 1, 1993.

Linna Ding, et al., "IL–10 Inhibits Macrophage Costimulatory Activity by Selectively Inhibiting the Up–Regulation of B7 Expression," *J. Immunol.* 151:1224=1234, Aug. 1, 1993.

Linna Ding, et al., "IL–10 Inhibits Mitogen–Induced T Cell Proliferation by Selectively Inhibitn Macrophage Costimulatory Function," *J. Immunol.* 148:33133–3139, May 15, 1992.

Stephan Fasler, et al., "Peptide–Induced Anergy in Allergen–Specific Human Th2 Cells Results in Lack of Cytokine Production and B Cell Help for IgE Synthesis," *J. Immunol.* 155:4199–4206, 1995.

Patrick E. Fields, et al., "Blocked Ras Activation in Anergic CD4+ T Cells," *Science* 271:1276–1278. 1996.

Hervé Groux, et al., "Interleukin–10 Induces a Long–Term Antigen–Specific Anergic State in Human CD4+ T Cells," *J. Exp. Med.* 184:19–29, Jul. 1996.

Marc K. Jenkins, "The Role of Cell Division in the Induction of Clonal Anergy," *Immunol. Today* 16:69–73, 1992.

Marc Jenkins, et al., "Inhibition of Antigen–Specific Proliferation of Type 1 Murine T Cell Clones after Stimulation with Immobilized Anti–CD3 Monoclonal Antibody," *J. Immunol.* 144:16–22, Jan. 1, 1990.

San–Mo Kang, et al., "Transactivation by AP–1 Is a Molecular Target of T Cell Clonal Anergy," *Science* 257:1134–1138, Aug. 21, 1992.

Jonathan R. Lamb, et al., "Induction of Tolerance in Influenza Virus–Immune T Lymphocyte Clones with Synthetic Peptides of Influcenza Hemagglutinin," *J. Exp. Med.* 157:1434–1447, May 1983.

Wei Li, et al., "Blocked Signal Transduction to the ERK and JNK Protein Kinases in Anergic CD4+ T Cells," *Science* 271:1272–1276, Mar. 1, 1996.

Steven E. Macatonia, et al., "Differential Effect of IL–10 on Dendritic Cell–Induced T Cell Proliferation and IFN–γ Production," *J. Immunol.* 150:3755–3765, May 1, 1993.

Ligia M. T. Peçanha, et al., "IL–10 Inhibits T Cell–Independent but Not T Cell–Dependent Responses in Vitro," *J. Immunol.* 150:3215–3233, Apr. 15, 1993.

Josette Péguet–Navarro, et al., "Interleukin–10 Inhibits the Primary Allogenic T Cell Response to Human Epidermal Langerhans Cells," *Er. J. Immunol.* 24:884–891, 1994.

Fred Ramsdell, et al., "Maintenance of in Vivo Tolerance by Persistence of Antigen," *Science* 257:1130–1134, Aug. 21, 1994.

Maria Grazia Roncarolo, et al., "Alloreactive T Cell Clones Specific for Class I and Class II HLA Antigens Isoated from a Human Chimera," *J. Exp. Med.* 167:1523–1534, May 1988.

Ronald H. Schwartz, "A Cell Culture Model for T Lymphocyte Clonal Anergy," *Science* 248:1349–1356, Jun. 15, 1990.

Gen Suzuki, et al., "Impaired CD–28–Mediated Co–Stimulation in Anergic T Cell," *Int'l. Immunol.* 7:37–43, 1995.

Kazuyuki Taga, et al., "Human Interleukin–10 Can Directly Inhibit T–Cell Growth," *Blood* 81:2964–2971, Jun. 1, 1993.

Fabieene Williams, et al., "Interleukin–10 Inhibits B7 and Intercellular Adhesion Molecule–1 Expression on Human Monocytes, " *Eur. J. Immunol.* 25:1007–1009, 1994.

Hans Yssel, et al., "IL–10 Is Produced by Subsets of Human CD4+ T Cell Clones and Peripheral Blood T Cell," *J. Immunol. J.* 149:2378–2384, Oct. 1, 1992.

\* cited by examiner

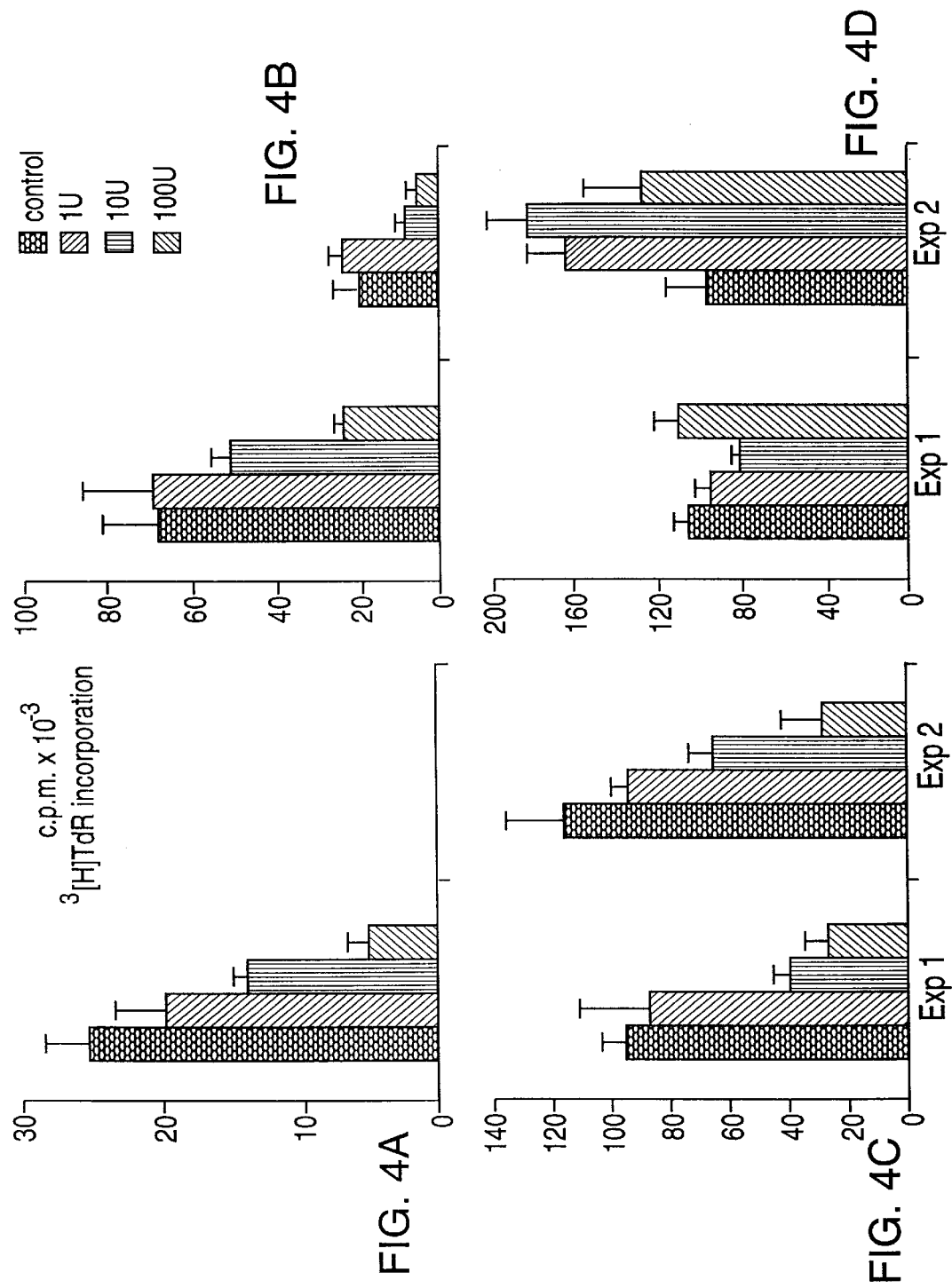

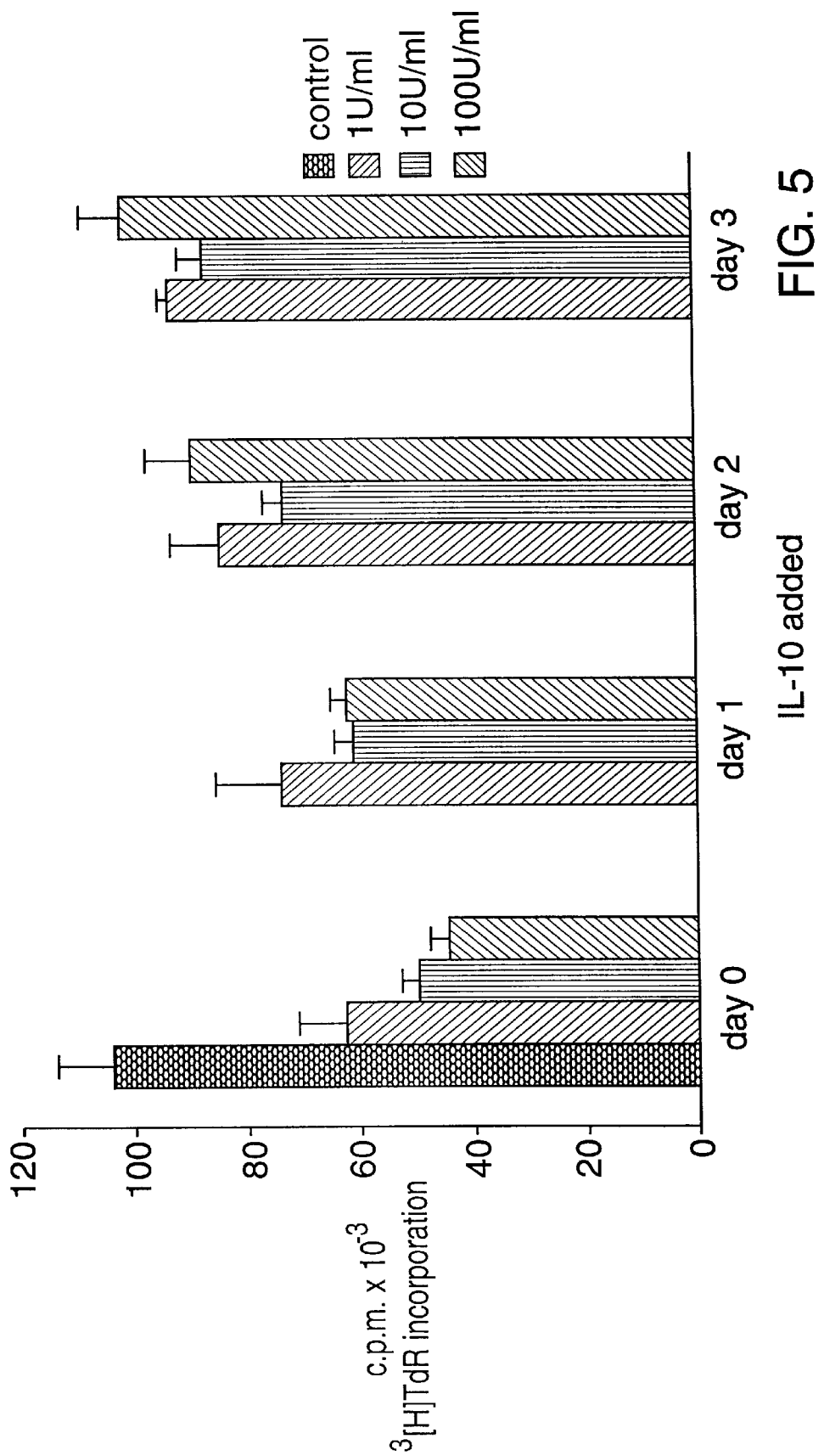

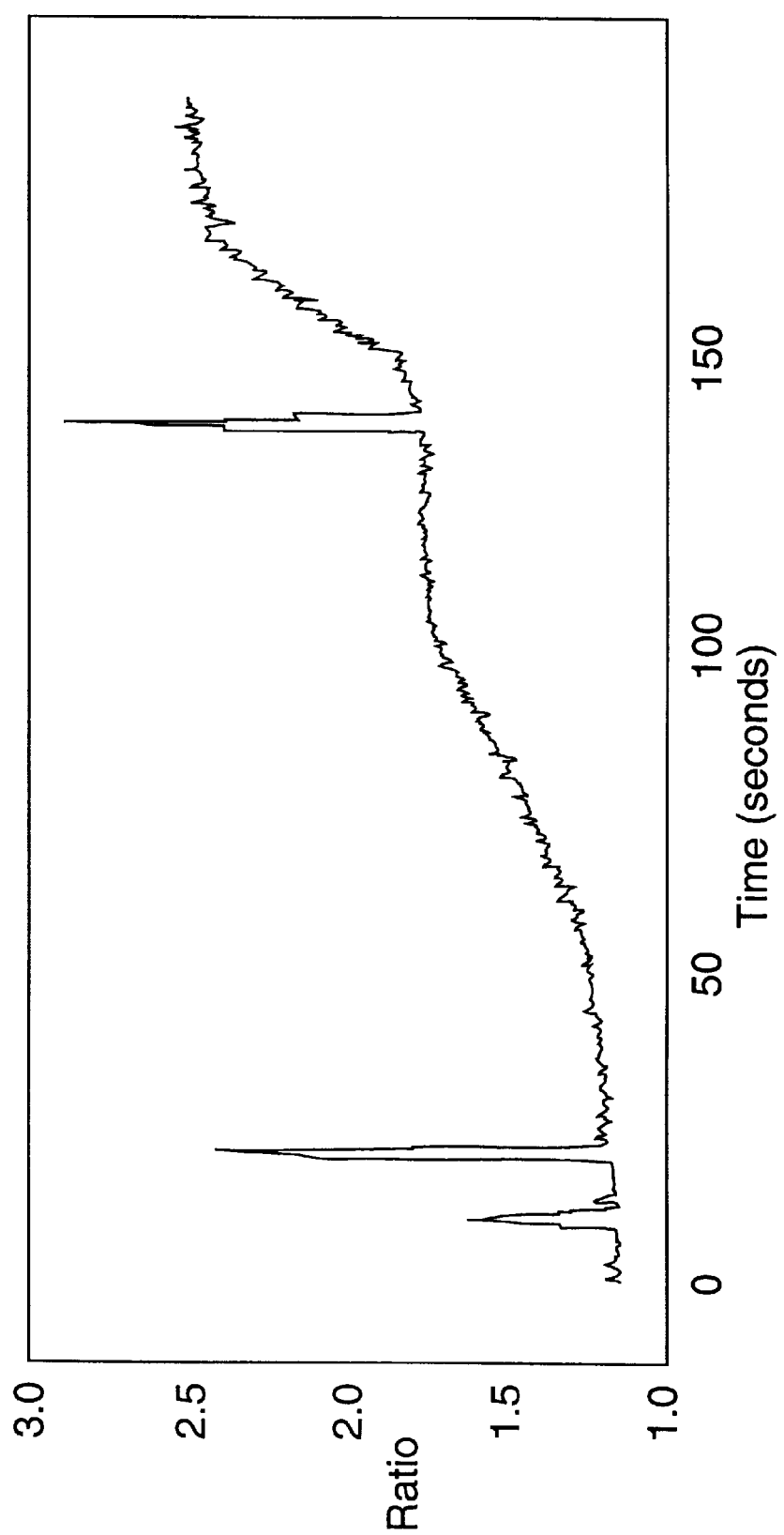

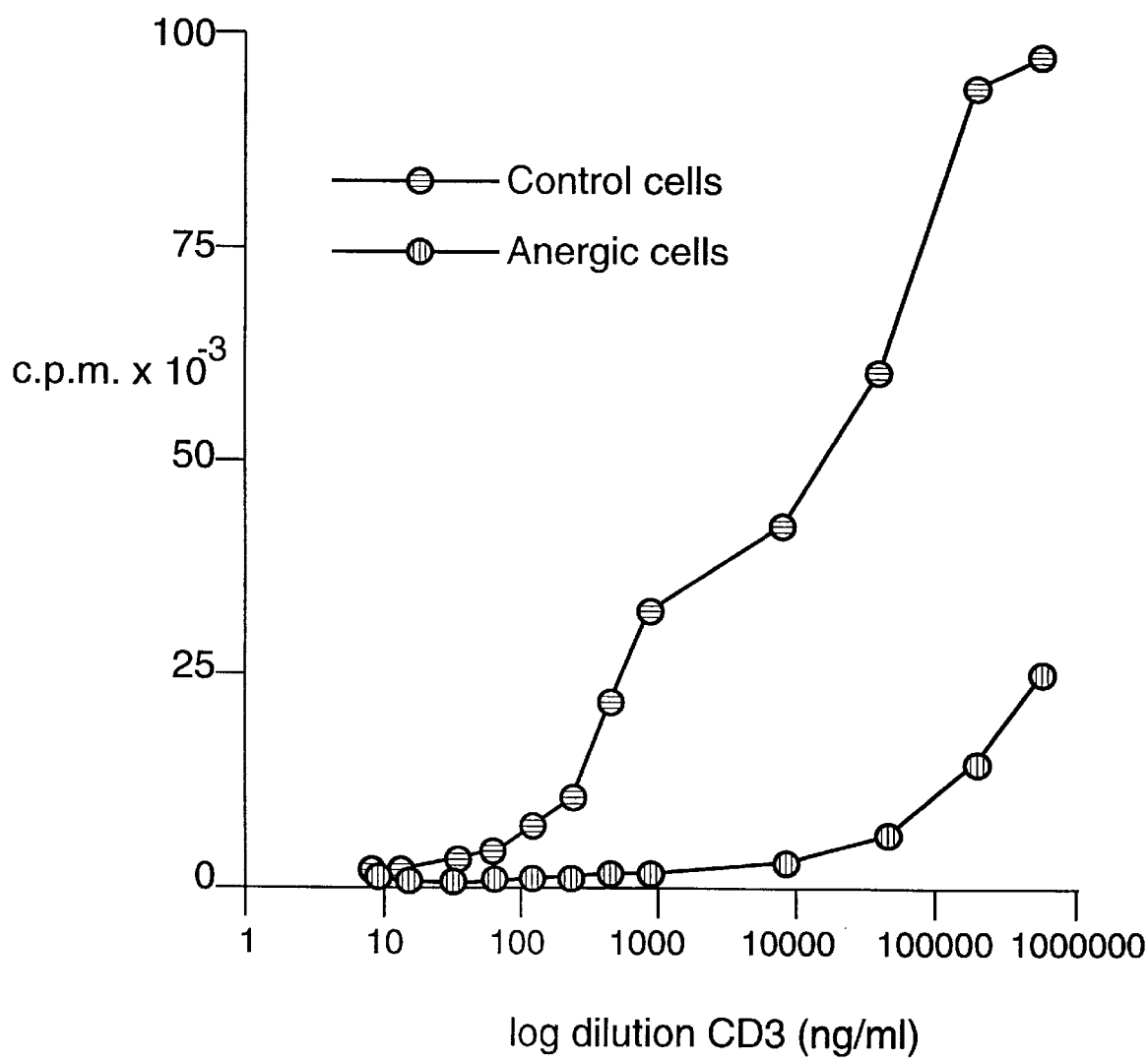

FIG. 18
Kinetics of IL-10 production by Th3 clones
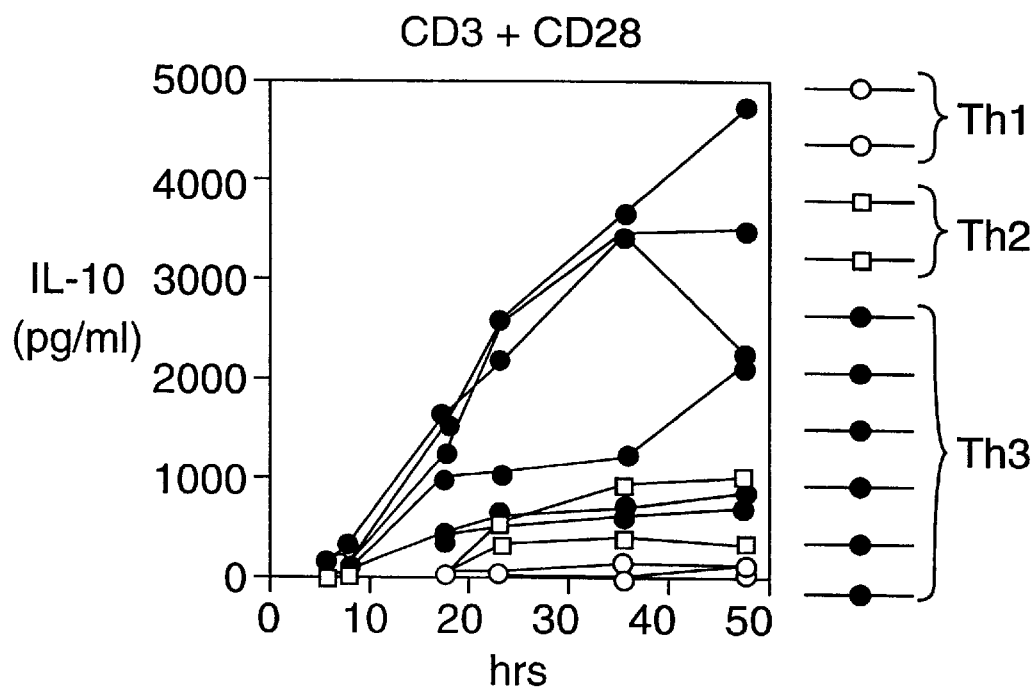
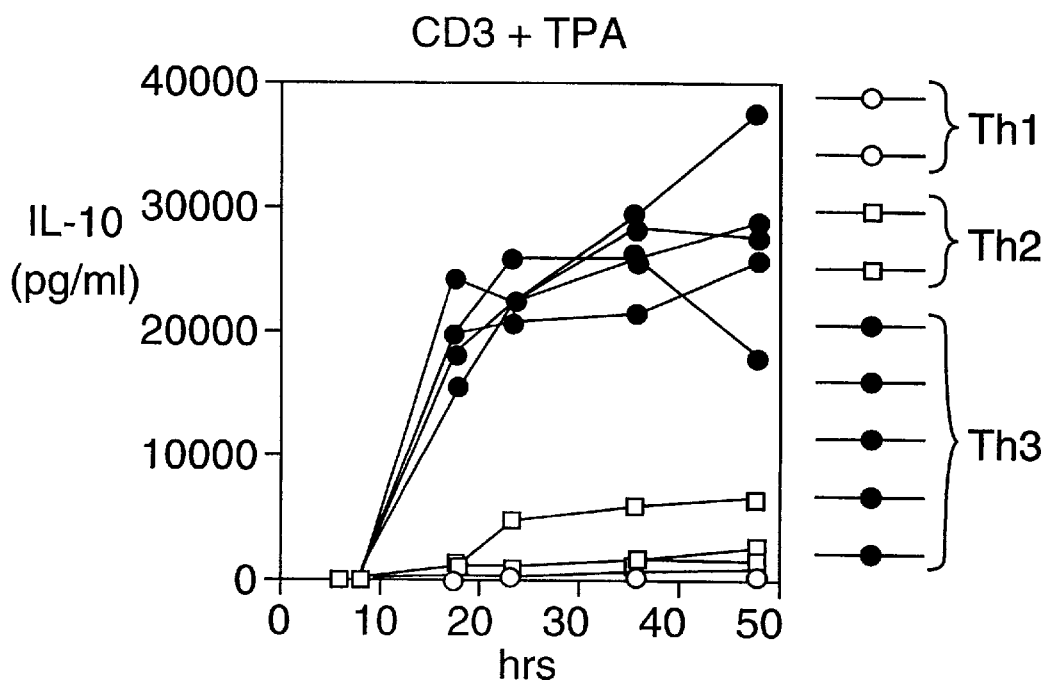

USE OF INTERLEUKIN-10 TO PRODUCE A POPULATION OF SUPPRESSOR CELLS

The present Application is a continuation-in-part of commonly assigned U.S. Ser. No. 07/846,208, filed Mar. 4, 1992, now abandoned which is incorporated herein by reference.

FIELD OF THE INVENTION

The invention relates generally use of interleukin-10 (IL-10) in producing a population of cells which act to suppress various immunological functions, e.g., methods for treating and inhibiting tissue rejection or other immune functions by administering to an afflicted individual an effective amount of interleukin-10.

BACKGROUND OF THE INVENTION

Interleukin-10 is a cytokine which was originally characterized by its activities in suppressing production of Th1 cytokines. See, e.g., de Vries and de Waal Malefyt (eds. 1995) *Interleukin*-10 Landes Co., Austin, Tex.; etc.

Suppression of immunological function finds utility in many different contexts. See, e.g., Paul (ed. 1995) *Fundamental Immunology* 3d ed., Raven Press, NY. In particular, allogeneic immunity is important in a transplantation context, due largely to its extraordinary strength. As organ and tissue transplants becomes more common in medical contexts, the ability to minimize problems from tissue rejection exhibit larger economic advantages. In addition, means to minimize autoimmune conditions, to block certain responses to particulate antigens, e.g., bacterial and parasitic, and to minimize reaction to certain soluble antigens, both protein and allergens, will be significant advances for therapeutic purposes.

The lack of fully effective therapeutics to minimize or eliminate tissue rejection, graft vs. host disease, or these other immunological responses leads to many problems. The present invention addresses and provides solutions to many of these problems.

SUMMARY OF THE INVENTION

The invention relates to the use of the cytokine interleukin-10 (IL-10) to suppress the rejection of transplanted tissues. The invention also includes pharmaceutical compositions comprising interleukin-10. Preferably, the interleukin-10 of the invention is selected from the group consisting of the mature polypeptides of the open reading frames defined by the following amino acid sequences:

```
Met His Ser Ser Ala Leu Leu Cys Cys Leu Val Leu Leu Thr Gly

Val Arg Ala Ser Pro Gly Gln Gly Thr Gln Ser Glu Asn Ser Cys

Thr His Phe Pro Gly Asn Leu Pro Asn Met Leu Arg Asp Leu Arg

Asp Ala Phe Ser Arg Val Lys Thr Phe Phe Gln Met Lys Asp Gln

Leu Asp Asn Leu Leu Leu Lys Glu Ser Leu Leu Glu Asp Phe Lys

Gly Tyr Leu Gly Cys Gln Ala Leu Ser Glu Met Ile Gln Phe Tyr

Leu Glu Glu Val Met Pro Gln Ala Glu Asn Gln Asp Pro Asp Ile

Lys Ala His Val Asn Ser Leu Gly Glu Asn Leu Lys Thr Leu Arg

Leu Arg Leu Arg Arg Cys His Arg Phe Leu Pro Cys Glu Asn Lys

Ser Lys Ala Val Glu Gln Val Lys Asn Ala Phe Asn Lys Leu Gln

Glu Lys Gly Ile Tyr Lys Ala Met Ser Glu Phe Asp Ile Phe Ile

Asn Tyr Ile Glu Ala Tyr Met Thr Met Lys Ile Arg Asn (see SEQ ID NO:1), and
Met Glu Arg Arg Leu Val Val Thr Leu Gln Cys Leu Val Leu Leu Tyr Leu Ala Pro Glu Cys Gly Gly Thr Asp Gln Cys Asp Asn Phe Pro Gln Met Leu Arg Asp Leu Arg Asp Ala Phe Ser Arg Val Lys Thr Phe Phe Gln Thr Lys Asp Glu Val Asp Asn Leu Leu Leu Lys Glu Ser Leu Leu Glu Asp Phe Lys Gly Tyr Leu Gly Cys Gln Ala Leu Ser Glu Met Ile Gln Phe Tyr Leu Glu Glu Val Met Pro Gln Ala Glu Asn Gln Asp Pro Glu Ala Lys Asp His Val Asn Ser Leu Gly Glu Asn Leu Lys Thr Leu Arg Leu Arg Leu Arg Arg Cys His Arg Phe Leu Pro Cys Glu Asn Lys Ser Lys Ala Val Glu Gln Ile Lys Asn Ala Phe Asn Lys Leu Gln Glu Lys Gly Ile Tyr Lys Ala Met Ser Glu Phe Asp Ile Phe Ile Asn Tyr Ile Glu Ala Tyr Met Thr Ile Lys Ala Arg (see SEQ ID NO:2),
``` wherein the standard three letter abbreviation is used to indicate L-amino acids, starting from the N-terminus. These two forms of IL-10 are sometimes referred to as human IL-10 (or human cytokine synthesis inhibitory factor ("CSIF") and viral IL-10 (or BCRF1), respectively, e.g., Moore, et al., Science 248:1230–1234 (1990); Vieira, et al., Proc. Natl. Acad. Sci. 88:1172–1176 (1991); Fiorentino, et al., J. Exp. Med. 170:2081–2095 (1989); and Hsu, et al., Science 250:830–832 (1990). A homolog has also been described in equine herpesvirus type 2 (Roe, et al., Virus Genes 7:111–116 (1993)) as well a numerous counterparts from various species. More preferably, the mature IL-10 used in the method of the invention is selected from the group consisting of prise reduced stimulatory capacity of peripheral blood mononuclear cells, dendritic cells, monocytes, and/or normal B cells.

In another embodiment, the invention provides a substantially pure antigen-specific anergic T cell characterized by production upon restimulation of low IL-2; low IL-4; low IL-5; intermediate IFN-γ; low GM-CSF; and high IL-10; with the population made by administering to precursors of said T cell with a combination of exogenous IL-10 and antigen. In preferred embodiments, the precursors are CD4+ T cells; the cells further produce high TNF-α; the cells induce an anergic response to the antigen; the administered IL-10 is human IL-10; the IL-10 is administered for at least about 7 days; and/or the anergic condition persists for at

```
Ser Pro Gly Gln Gly Thr Gln Ser Glu Asn Ser Cys Thr His Phe

Pro Gly Asn Leu Pro Asn Met Leu Arg Asp Leu Arg Asp Ala Phe

Ser Arg Val Lys Thr Phe Phe Gln Met Lys Asp Gln Leu Asp Asn

Leu Leu Leu Lys Glu Ser Leu Leu Glu Asp Phe Lys Gly Tyr Leu

Gly Cys Gln Ala Leu Ser Glu Met Ile Gln Phe Tyr Leu Glu Glu

Val Met Pro Gln Ala Glu Asn Gln Asp Pro Asp Ile Lys Ala His

Val Asn Ser Leu Gly Glu Asn Leu Lys Thr Leu Arg Leu Arg Leu

Arg Arg Cys His Arg Phe Leu Pro Cys Glu Asn Lys Ser Lys Ala

Val Glu Gln Val Lys Asn Ala Phe Asn Lys Leu Gln Glu Lys Gly

Ile Tyr Lys Ala Met Ser Glu Phe Asp Ile Phe Ile Asn Tyr Ile

Glu Ala Tyr Met Thr Met Lys Ile Arg Asn (see SEQ ID NO:3)

and

Thr Asp Gln Cys Asp Asn Phe Pro Gln Met Leu Arg Asp Leu Arg

Asp Ala Phe Ser Arg Val Lys Thr Phe Phe Gln Thr Lys Asp Glu

Val Asp Asn Leu Leu Leu Lys Glu Ser Leu Leu Glu Asp Phe Lys

Gly Tyr Leu Gly Cys Gln Ala Leu Ser Glu Met Ile Gln Phe Tyr

Leu Glu Glu Val Met Pro Gln Ala Glu Asn Gln Asp Pro Glu Ala

Lys Asp His Val Asn Ser Leu Gly Glu Asn Leu Lys Thr Leu Arg

Leu Arg Leu Arg Arg Cys His Arg Phe Leu Pro Cys Glu Asn Lys

Ser Lys Ala Val Glu Gln Ile Lys Asn Ala Phe Asn Lys Leu Gln

Glu Lys Gly Ile Tyr Lys Ala Met Ser Glu Phe Asp Ile Phe Ile

Asn Tyr Ile Glu Ala Tyr Met Thr Ile Lys Ala Arg (see SEQ ID NO:4).
```

Thus, in particular embodiments, the present invention provides a method of reducing or inhibiting graft vs. host disease in a bone marrow transfer in a mammal, comprising administering to the mammal an effective amount of interleukin-10. It also provides a method of inhibiting, by an immune system, an antigen-specific response to subsequent presentation of said antigen, comprising administering to said immune system an effective amount of exogenous interleukin-10 and that antigen. In preferred embodiments, the immune response is mediated by a macrophage, APC, langerhans cell, or dendritic cell; the method further inhibits proliferative response of CD4+ host-reactive T cell clones; or the inhibiting persists for at least about 21 days. In other preferred embodiments, the effective amount is sufficient to decrease responder T cell activation; or may further comprise least about 21 days. The antigen specificity may be to an antigen is selected from a protein antigen; a particulate antigen; an alloantigen; or an autoantigen.

Another embodiment is a substantially pure antigen-specific anergic T cell characterized by production upon restimulation of low IL-2; low IL-5; intermediate IFN-γ; low GM-CSF; and high IL-10. Typically, the levels of production of the cytokines is, for IL-2 less than about 500 pg/ml; for IL-5 between about 300 and 3000 pg/ml; for IFN-γ at least about 1000 pg/ml; for GM-CSF between about 300–3000 pg/ml; and for IL-10 at least about 3000 pg/ml. Preferably, the IL-10 level upon restimulation with anti-CD3 is at least about 5× that of a Th1 cell.

The invention also embraces a substantially pure T cell which exhibits an antigen-specific anergy to an antigen, including, e.g., where the antigen is an alloantigen or self antigen; which produces IL-10 upon restimulation with anti-CD3 of at least about 3000 pg/ml; or which exhibits the antigen-specific anergy for at least about 21 days.

In another embodiment, the invention provides a method of suppressing a response in a T cell to an antigen, by administering to an immune system containing such cell a combination of exogenous IL-10 and either antigen or anti-CD3 antibodies. Preferably, the antigen is alloantigen or self antigen; but is usually restricted by MHC molecules. In other embodiments, the method is performed in vivo; or further suppresses response to subsequent stimulation, e.g., a response which accompanies tissue transplantation such as an organ or bone marrow transplant. Typically, the T cell is from the recipient of said tissue transplantation and the antigen is from the donor MHC. Often, when the response accompanies tissue transplantation, the administering is prior to the tissue transplantation; the T cell is introduced to the recipient; or IL-10 is administered to the tissue to be transplanted before the transplantation, e.g., to the donor and/or during transport. In other embodiments, the antigen causes an autoimmune disease.

In other embodiments, the invention also provides a method of suppressing a subsequent response in a T cell to an antigen by administering to an immune system a combination of exogenous IL-10; and either antigen or anti-CD3 antibodies. Preferably, the IL-10 is administered for at least about 7 days.

The present invention further provides a method of inducing in a T cell anergy to an MHC antigen, by administering to a precurser to the T cell either exogenous IL-10 and antigen; or exogenous IL-10 with anti-CD3 antibodies. Preferably, the administering of IL-10 is for at least about 7 days.

Another embodiment which is embraced by the invention is a composition comprising IL-10 and antigen. The composition may be a pharmaceutical composition comprising IL-10 and a pharmaceutically acceptable carrier; the IL-10 may be human IL-10; or the antigen may be alloantigen; self antigen; protein antigen; or particulate antigen.

BRIEF DESCRIPTION OF THE DRAWINGS

FIG. 3A shows the effects of endogenous and exogenous IL-10 on proliferative responses in mixed lymphocyte response (MLR): PBMC donor A X irradiated PBMC donor B. FIG. 3B shows the effects of endogenous and exogenous IL-10 on proliferative responses in MLR: PBMC donor B X irradiated PBMC donor A. FIG. 3C shows the neutralization of the inhibitory effects of IL-10 by anti-IL-10 mAb.

FIGS. 4A through 4D shows histograms of the proliferative responses of purified T cells stimulated with various allogeneic cells, each in the presence of increasing concentrations of IL-10. FIG. 4A shows stimulation of purified T cells with allogeneic irradiated elutriated monocytes. FIG. 4B shows stimulation of purified T cells with positively sorted CD14+ monocytes. FIG. 4C shows stimulation of purified T cells with purified B cells. FIG. 4D shows stimulation of purified T cells with Epstein-Barr virus transformed lymphoblastoid cell line (EBV-LCL).

FIG. 5 shows a histogram of the kinetics of IL-10 on peripheral blood mononuclear cells (PBMC) and allogeneic irradiated PBMC.

FIG. 7A shows a graph of the effect of exogenous IL-2 on the reduced alloantigen-induced proliferative response of T cells stimulated with allogeneic irradiated PBMC and induced by IL-10. FIG. 7B shows a graph of the effect of exogenous IL-2 on the reduced alloantigen-induced proliferative response of T cells stimulated with purified allogeneic B cells and induced by IL-10.

FIG. 8A shows [$^3$H]-TdR incorporation of purified CD4+ T cells cultured for 3 days in medium alone (white bar) or stimulated in a primary MLR with allogeneic purified monocytes (gray bar) in the presence of IL-10 (100 U/ml) (black bar) or the anti-IL-2 receptor a chain mAb BB-10 (hatched bar). FIG. 8B shows three different panels which represent cells that have been preactivated as described in FIG. 8A, kept in culture for 10 days in the presence of IL-10, washed, and restimulated with either medium alone (black bars), allogeneic irradiated PBMC isolated from a third party donor different from that of the monocytes used in the preactivation step (PBMC-2, cross-hatched bars), allogeneic irradiated PBMC isolated from the same donor used in the preactivation step (PBMC-1, gray bars), PBMC-1 plus IL-2 (20 U/ml) (black-hatched bars), or PBMC-1 plus anti-CD28 mAbs (10 µg/ml) (hatched bars).

FIG. 9A: [$^3$H]-TdR incorporation of purified CD4+ T cells cultured for 3 days in medium alone (white bar), or stimulated with crosslinked anti-CD3 mAbs (500 ng/ml) (black bar) in the presence of IL-10 (100 U/ml) (cross-hatched bar) or the anti-IL-2 receptor a chain mAb BB-10 (hatched bar). FIG. 9B show three different portions which represent cells that have been preactivated as described in FIG. 9A, kept in culture for 10 days in the presence of IL-10, washed, and restimulated with either medium alone (black bars), crosslinked anti-CD3 mabs (gray bars), anti-CD3 mAbs plus IL-2 (20 U/ml) (cross-hatched bars), anti-CD3 mAbs plus anti-CD28 mAbs (10 µg/ml) (black-hatched bars), or PMA (1 ng/ml) plus $Ca^{2+}$ ionophore (A23187, 500 ng/ml) (white bars).

Figure 12:
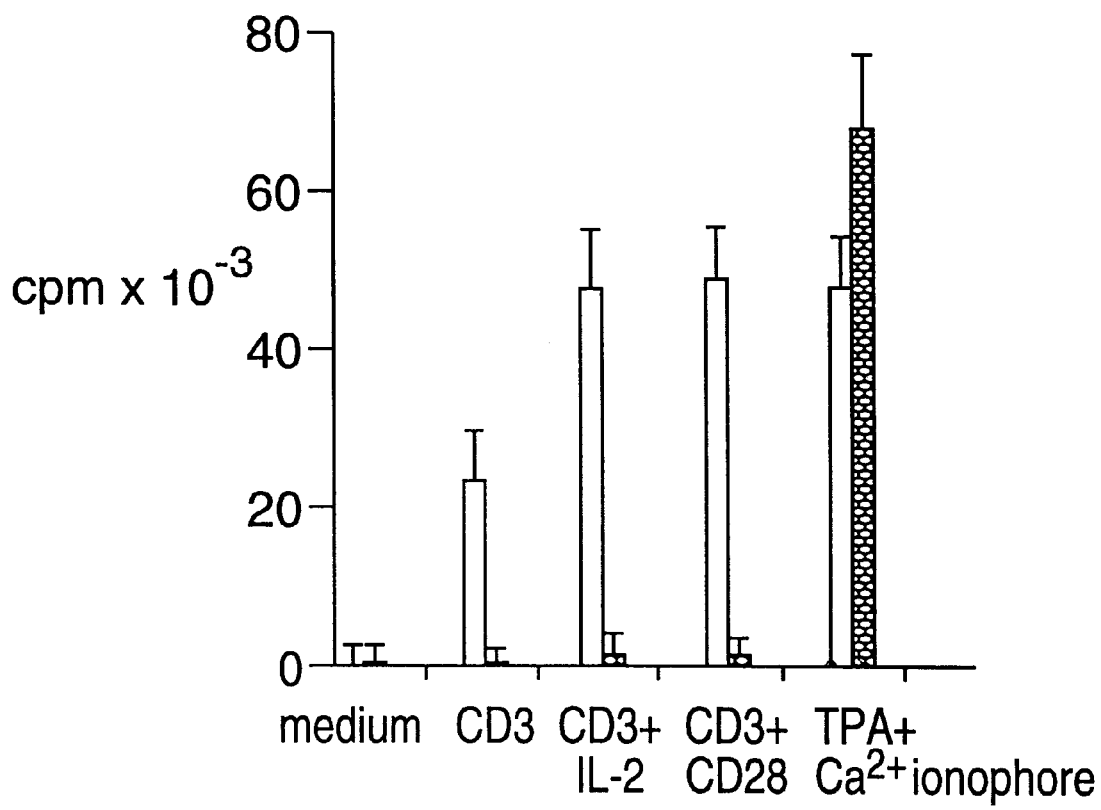

FIG. 12 shows anergy induced by IL-10 in $CD4^+$ T cells is long lasting. $CD4^+$ T cells were activated with crosslinked anti-CD3 mAbs in the absence (white bars) or presence (black bars) of IL-10 (100 U/ml) for 10 days. After 10 days, cells were collected, washed, and cultured in the presence of IL-2 (2 U/ml). Twenty four days later, cells were collected and reactivated with crosslinked anti-CD3 mAbs, crosslinked anti-CD3 mAbs plus IL-2 (20 U/ml), crosslinked anti-CD3 mAbs plus anti-CD28 mAbs (10 µg/ml), or PMA plus $Ca^{2+}$ ionophore.

Figure 13:
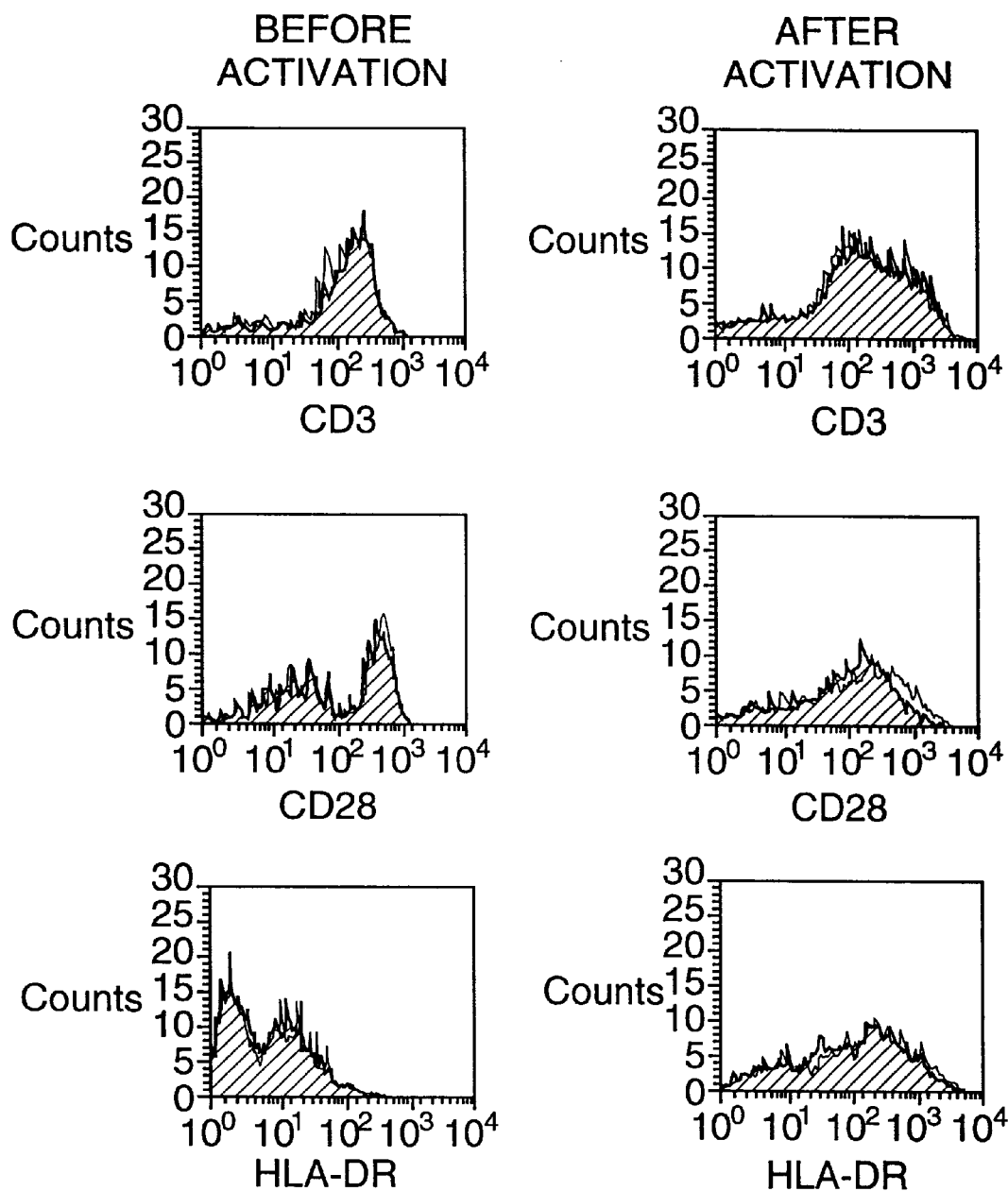

FIG. 13 shows cytofluorometric analysis of anergic T cells. $CD4^+$ T cells were activated with crosslinked anti-CD3 mAbs in the absence or presence of IL-10 (100 U/ml) for 10 days and the expression of CD3, CD28, and HLA-DR was analyzed before and after reactivation with crosslinked anti-CD3 mAbs for 24 hrs. The black line shows control T cells cultured in the absence of IL-10 and the dotted histograms anergic T cells that were cultured in the presence of IL-10.

Figure 14A:
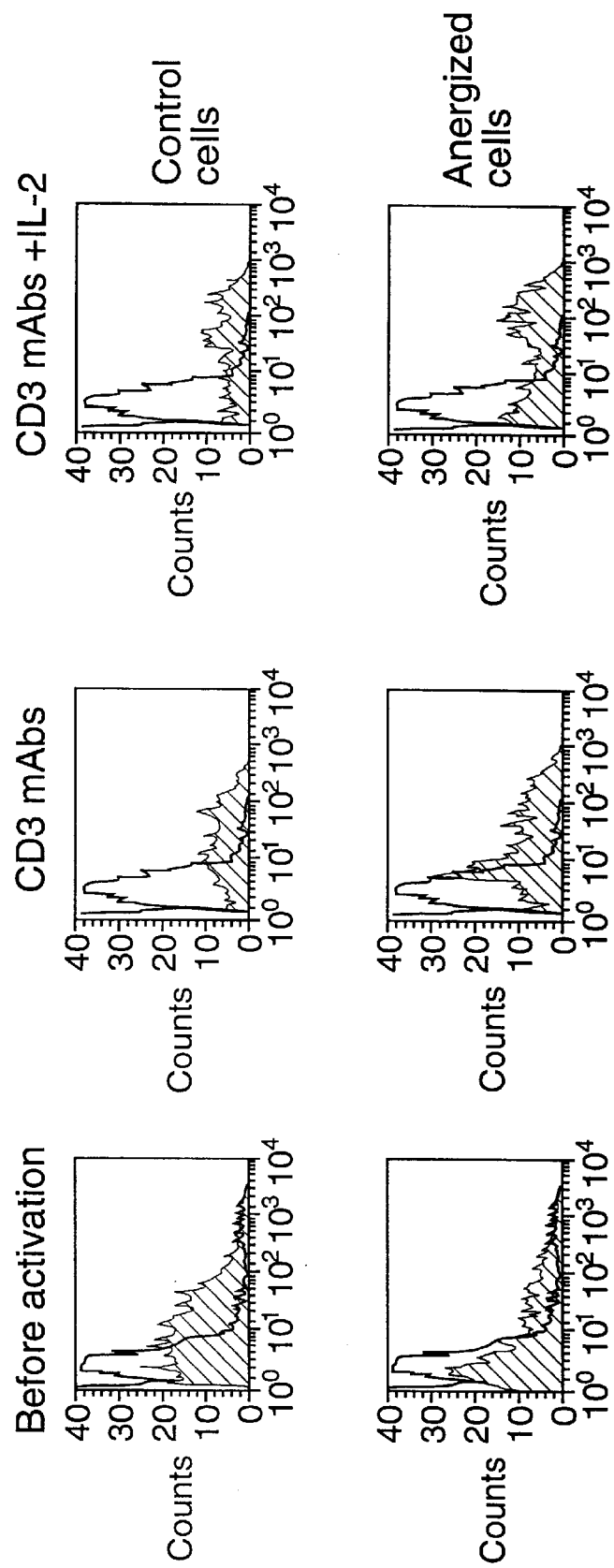
Figure 14B:
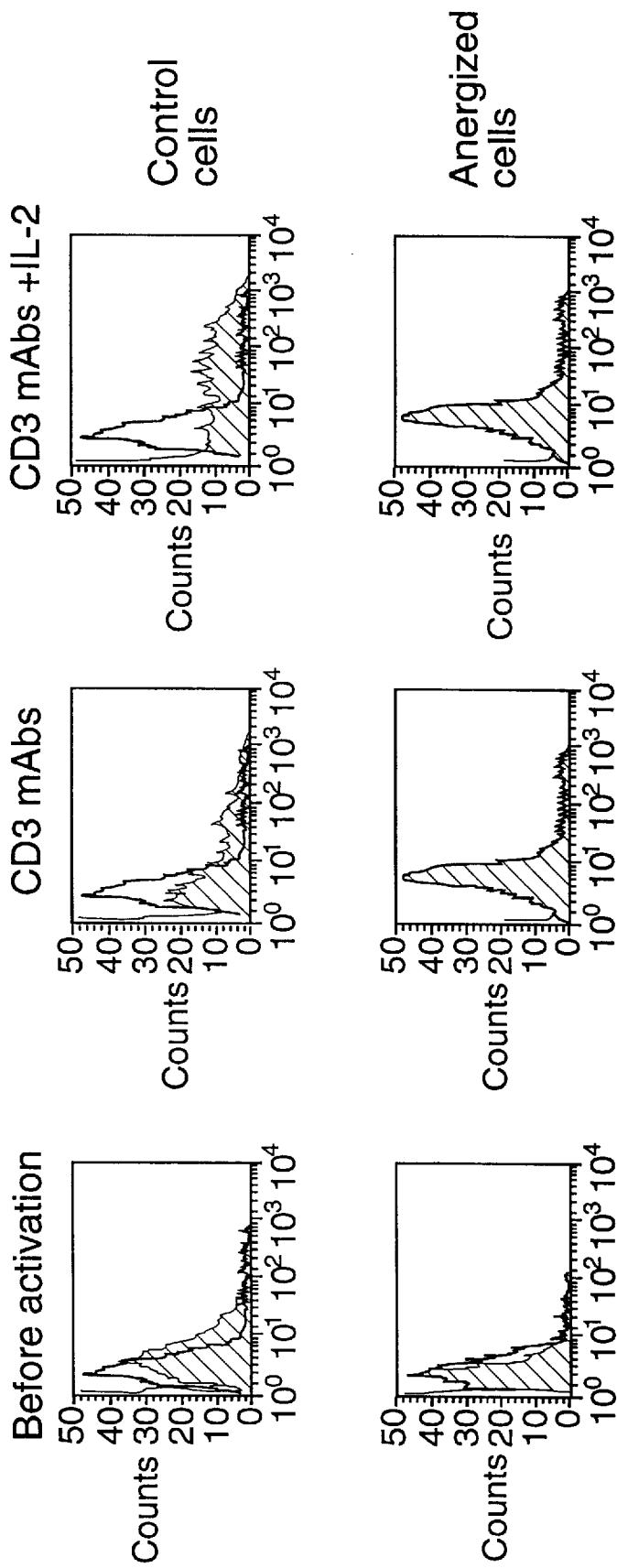

FIGS. 14A and 14B show IL-2R α chain expression on anergic T cells. $CD4^+$ T cells were activated with crosslinked anti-CD3 mAbs in the presence or absence of IL-10 (100 U/ml) for 3 days (FIG. 14A) or 10 days (FIG. 14B) and restimulated with either crosslinked anti-CD3 mAbs alone or with crosslinked anti-CD3 mAbs plus IL-2 (100 U/ml). The expression of the CD25 molecule was analyzed 24 hr after activation by cytofluorometry. The black line shows the control isotype and the dotted histogram the labeling with anti-CD25 mAbs.

Figure 15A:
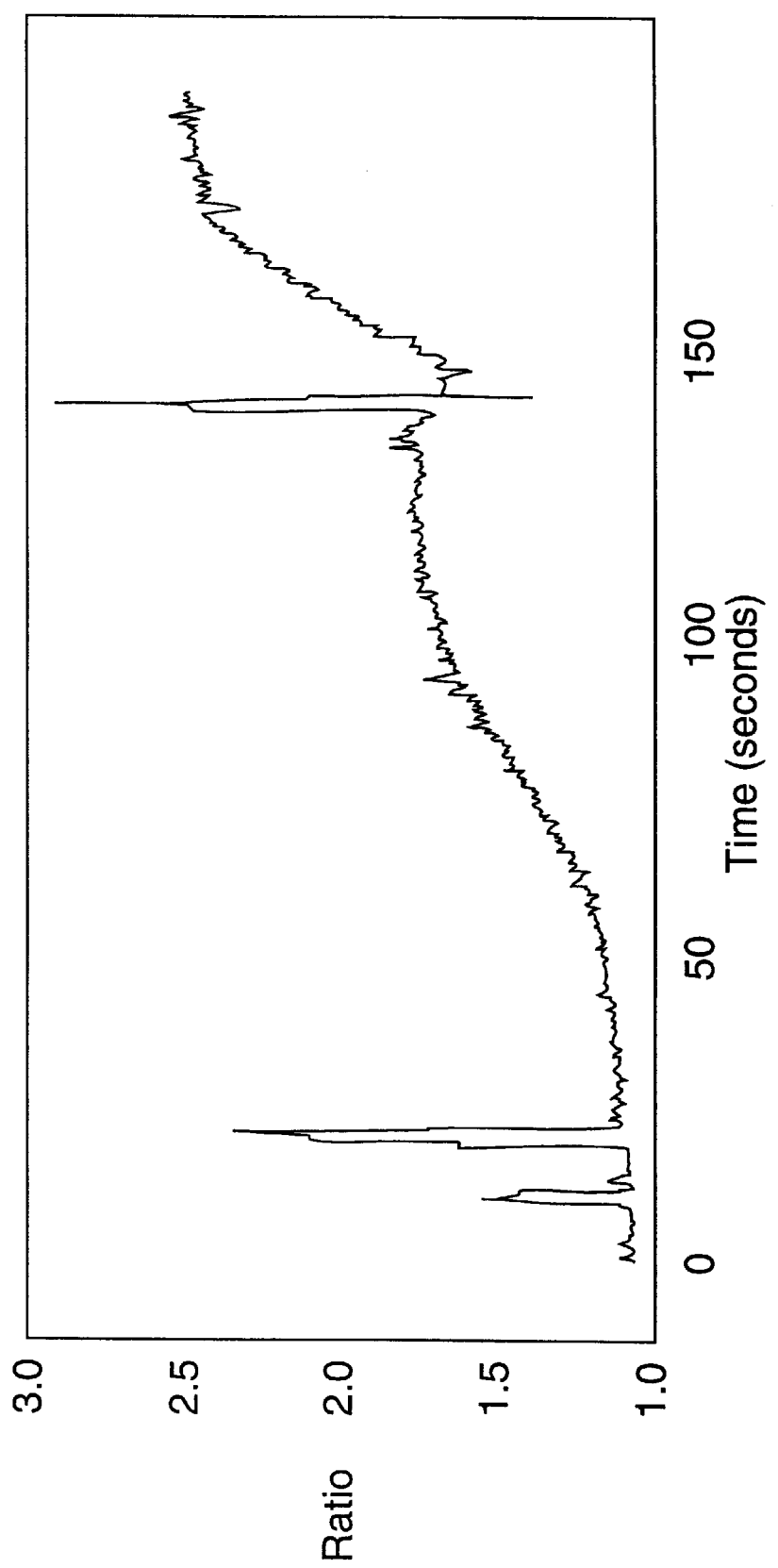

FIGS. 15A and 15B show calcium mobilization analysis in anergic cells. $CD4^+$ T cells were activated with anti-CD3 mAbs in the absence (FIG. 15A) or presence (FIG. 15B) of IL-10 (100 U/ml) for 10 days and loaded with indo-1/AM. As indicated, anti-CD3 mAbs (10 µg/ml), goat anti-mouse IgG (1 µg/ml), or $Ca^{2+}$ ionophore (500 ng/ml) were added into the cuvette and the rise of intracellular $Ca^{2+}$ was analyzed by spectrofluorimetry and measured by the ratio of emission at 405/485 nm.

FIG. 16 shows that the proliferative responses of purified $CD4^+$ T cells that had been rendered anergic following stimulation with crosslinked anti-CD3 mAbs (100 ng/ml) in the presence of IL-10 (100 U/ml) for 10 days, can be partially restored following restimulation with very high concentrations of crosslinked anti-CD3 mAbs. After the 10 day induction phase, the $CD4^+$ T cells were harvested and centrifuged over Ficoll/hypaque to remove non-viable cells. Next the cells were collected and washed 3 times with PBS. The $CD4^+$ cells ($4 \times 10^4$/well) were subsequently restimulated by increasing concentrations (10 ng to 1 mg/ml) crosslinked anti-CD3 mAbs for 3 days.

Figure 17:
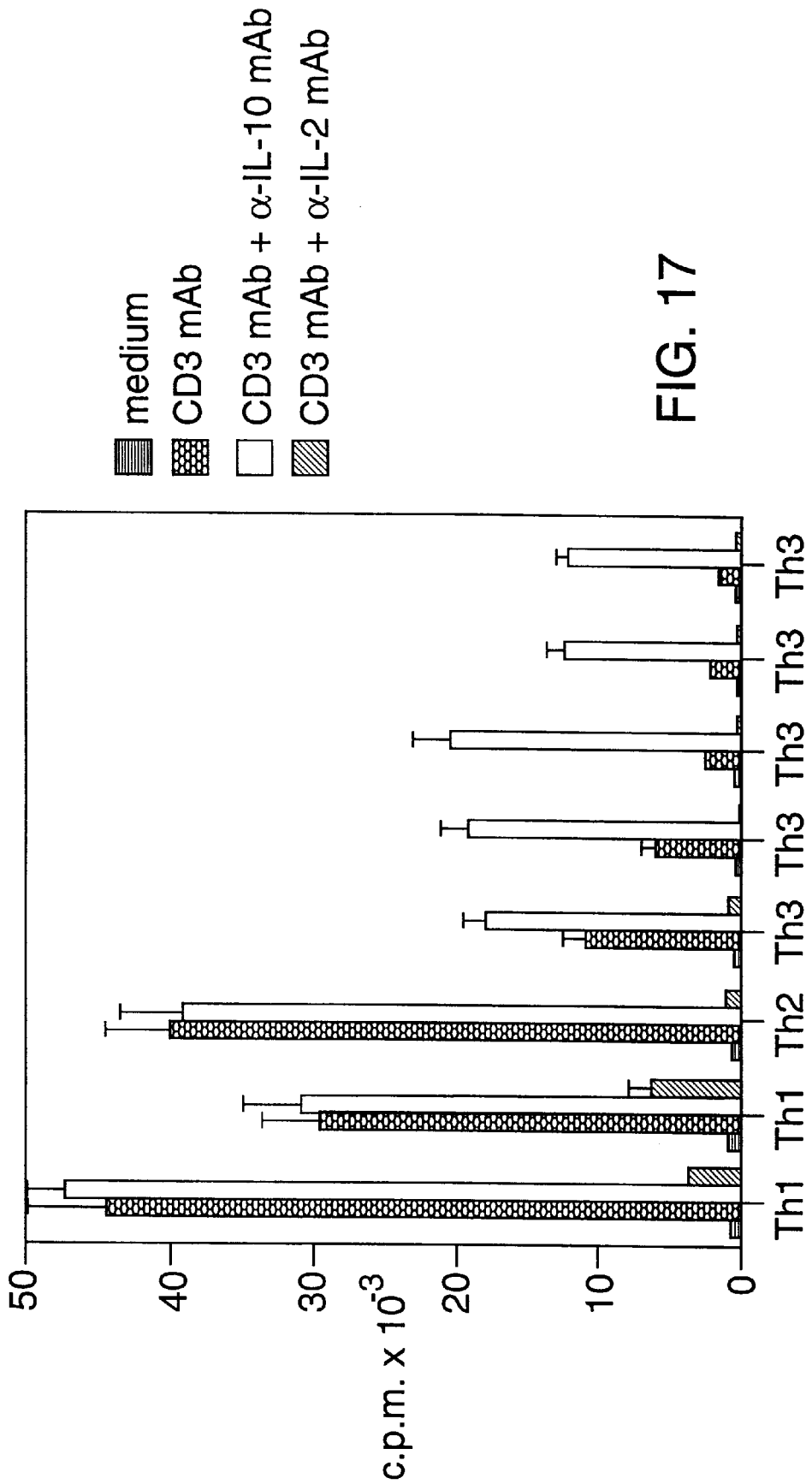

FIG. 17 shows the proliferative responses of Th3 clones as compared to those of Th1 and Th2 clones. The T-cell clones were maintained by stimulation at biweekly intervals with irradiated feeder cells and PHA. Resting T-cell clones were collected 12 days after stimulation by feeder cells and PHA, washed and restimulated with crosslinked anti-CD3 mAbs (100 ng/ml) in the presence or absence of anti-IL-10 mAb (10 µg/ml) or anti-IL-2 mAb (10 µg/ml). It is shown that the proliferative responses of the Th3 clones are very low as compared to those of the Th1 and Th2 clones. In addition, the proliferative responses of Th3 clones, in contrast to those of the control Th1 and Th2 clones, are considerably enhanced by anti-IL-10 mAbs, but even in the presence of anti-IL-10 mAbs the response never reached the levels of those of the control Th1 and Th2 clones. The proliferative responses of all types of T-cell clones, including the Th3 clones, are completely inhibited by anti-IL-2 mAbs.

FIG. 18 shows that IL-10 production by Th3 clones occurs rapidly after activation of the cells. Considerable levels of IL-10 are already produced 16 hrs following activation of the T-cell clones by combinations of either anti-CD3 or anti-CD28 mAbs (FIG. 18A), or anti-CD3 mAbs + the phorbol ester PMA (FIG. 18B). In contrast, only low levels of IL-10 production by Th1 or Th2 clones can first be measured 24 hrs after activation of the cells.

DETAILED DESCRIPTION OF SPECIFIC EMBODIMENTS

The invention is directed, in certain embodiments, to methods of using IL-10 to suppress tissue rejection in transplant patients. The invention also includes pharmaceutical compositions comprising IL-10 for carrying out the method. Various IL-10s for use in the invention are selected from the group of mature polypeptides encoded by the open reading frames defined by the cDNA inserts of pH5C, pH15C, and pBCRF1(SRα), which were deposited with the American Type Culture Collection (ATCC), Rockville, Md., on Dec. 20, 1989, under accession numbers 68191, 68192, and 68193. Constructs can also be based upon other expression systems. See, e.g., Pouwels, et al., Cloning Vectors: A Laboratory Manual (Elsevier, N.Y., 1985 and Supplements); and Rodriquez, et al. (eds.) Vectors: A Survey of Molecular Cloning Vectors and Their Uses (Buttersworth, Boston, Mass., 1988). PCR methods may be applied to isolate other genes encoding IL-10s, e.g., polymorphic or species variants.

IL-10 is a cytokine with potent immunosuppressive properties. IL-10 inhibits antigen-specific T-cell proliferation at different levels. IL-10 inhibits the antigen-presenting and accessory cell function of professional antigen-presenting cells such as monocytes, dendritic cells and Langerhans cells by downregulation of the expression of MHC class II molecules and of the adhesion and co-stimulatory molecules ICAM-1 and B7.1 and B7.2 (reviewed in Interleukin 10, de Vries and de Waal Malefyt, eds., Landes Co, Austin Tex., 1995). IL-10 also inhibits IL-12 production by these cells, which promotes T-cell activation and the differentiation of Th1 cells (D'Andrea, et al., J. Exp. Med., 178:1041 (1993); Hsieh, et al., Science, 260:547 (1993)). In addition, IL-10 directly inhibits T-cell proliferation by inhibiting IL-2 gene transcription and IL-2 production by these cells (reviewed in Interleukin 10, de Vries and de Waal Malefyt, eds., Landes Co, Austin Tex., (1995)).

Moreover, IL-10 has strong anti-inflammatory properties. It inhibits the production of the pro-inflammatory cytokines TNF-α, IL-1α, IL-1β, IL-6, and chemokines such as IL-8, MIP-1α, and MIP-1β by activated monocytes/macrophages, neutrophils, eosinophils, and mast cells (reviewed in Interleukin 10, de Vries and de Waal Malefyt, eds., Landes Co, Austin Tex. (1995); Takanashi, et al., J. Exp. Med. 180:711 (1994); Arock, et al., Eur. J. Med. 26:166 (1996)). In addition, IL-10 supports nitric oxide-dependent microbicidal activity of macrophages and prostaglandin production by these cells (Gazzinelli, et al., J. Immunol. 148:1792 (1992); Cunha, et al., Biochem. Biophys. Res. Commun. 182:1155 (1992); Niiro, et al., Int. Immunol. 6:661 (1994). On the other hand, it upregulates the production of the IL-1 receptor antagonist by monocytes and granulocytes (reviewed in Interleukin 10, de Vries and de Waal Malefyt, eds., Landes Co, Austin Tex. (1995)).

Collectively, these data indicate that IL-10 may have potential clinical utility in the treatment of diseases associated with undersired T-cell activation and T-cell expansion such as autoimmune diseases, organ and bone marrow transplant rejection, graft-versus-host disease, parasitic infections, e.g., granulomas, inflammatory diseases, e.g., Crohn's disease, colitis, pancreatitis, inflammatory lung and eye diseases, parasitic diseases, and allergic diseases, e.g., asthma, atopic dermatitis, and rhinitis.

I. Assays for Interleukin-10

IL-10s exhibit several biological activities which could form the basis of assays and units. See, e.g., Coligan (ed) Current Protocols in Immunology (Greene/Wiley, NY, 1989 and periodic supplements). In particular, IL-10s have property of inhibiting the synthesis of at least one cytokine in the group consisting of IFN-$\gamma$, lymphotoxin, IL-2, IL-3, and GM-CSF in a population of T helper cells induced to synthesize one or more of these cytokines by exposure to antigen and antigen presenting cells (APCs). In this activity, the APCs are treated so that they are incapable of replication, but that their antigen processing machinery remains functional. This is conveniently accomplished by irradiating the APCs, e.g., with about 1500–3000 R (gamma or X-radiation) before mixing with the T cells.

Alternatively, cytokine inhibition may be assayed in primary or, preferably, secondary mixed lymphocyte reactions (MLR), in which case syngeneic APCs need not be used. MLRs are well known in the art, e.g., Bradley, pgs. 162–166, in Mishell, et al., eds. *Selected Methods in Cellular Immunology* (Freeman, San Francisco, 1980); and Battisto et al., Meth. in Enzymol. 150:83–91 (1987) Academic Press. Briefly, two populations of allogeneic lymphoid cells are mixed, one of the populations having been treated prior to mixing to prevent proliferation, e.g., by irradiation. Preferably, the cell populations are prepared at a concentration of about $2 \times 10^6$ cells/ml in supplemented medium, e.g., RPMI 1640 with 10% fetal calf serum. For both controls and test cultures, mix 0.5 ml of each population for the assay. For a secondary MLR, the cells remaining after 7 days in the primary MLR are re-stimulated by freshly prepared, irradiated stimulator cells. The sample suspected of containing IL-10 may be added to the test cultures at the time of mixing, and both controls and test cultures may be assayed for cytokine production from 1 to 3 days after mixing.

Obtaining T cell populations and/or APC populations for IL-10 assays employs techniques well known in the art which are fully described, e.g., in DiSabato, et al., eds., Meth. in Enzymol. vol. 108 (1984) Academic Press. APCs for the preferred IL-10 assay are peripheral blood monocytes. These are obtained using standard techniques, e.g., as described by Boyum, Meth. in Enzymol. 108:88–102 (1984); Mage, Meth. in Enzymol. 108:118–132 (1984); Litvin, et al., Meth. in Enzymol. 108:298–302 (1984); Stevenson, Meth. in Enzymol. 108:242–249 (1984); and Romain, et al., Meth. in Enzymol. 108:148–153 (1984), which references are incorporated by reference. Preferably, helper T cells are used in the IL-10 assays, which are obtained by first separating lymphocytes from the peripheral blood then selecting, e.g., by panning or flow cytometry, helper cells using a commercially available anti-CD4 antibody, e.g., OKT4 described in U.S. Pat. No. 4,381,295 and available from Ortho Pharmaceutical Corp. The requisite techniques are fully disclosed in Boyum, Scand. J. Clin. Lab. Invest. 21(Suppl. 97):77 (1968); Meth. in Enzymol. Vol. 108 (cited above), and Bram, et al., Meth. in Enzymol. 121:737–748 (1986). Generally PBLs are obtained from fresh blood by Ficoll-Hypaque density gradient centrifugation.

A variety of antigens can be employed in the assay, e.g., Keyhole limpet hemocyanin (KLH), fowl $\gamma$-globulin, or the like. More preferably, in place of antigen, helper T cells are stimulated with anti-CD3 monoclonal antibody, e.g., OKT3 disclosed in U.S. Pat. No. 4,361,549, in the assay.

Cytokine concentrations in control and test samples are measured by standard biological and/or immunochemical assays. Construction of immunochemical assays for specific cytokines is well known in the art when the purified cytokine is available, e.g., Campbell, Monoclonal Antibody Technology (Elsevier, Amsterdam, 1984); Tijssen, Practice and Theory of Enzyme Immunoassays (Elsevier, Amsterdam, 1985); and U.S. Pat. No. 4,486,530 are exemplary of the extensive literature on the subject. ELISA kits for human IL-2, human IL-3, and human GM-CSF are commercially available from Genzyme Corp. (Boston, Mass.); and an ELISA kit for human IFN-$\gamma$ is commercially available from Endogen, Inc. (Boston, Mass.). Polyclonal antibodies specific for human lymphotoxin are available from Genzyme Corp. which can be used in a radioimmunoassay for human lymphotoxin, e.g., Chard, An Introduction to Radioimmunoassay and Related Techniques (Elsevier, Amsterdam, 1982). See also Coligan, et al. (eds.) Current Protocols in Immunology.

Biological assays of the cytokines listed above can also be used to determine IL-10 activity. A biological assay for human lymphotoxin is disclosed in Aggarwal, Meth. in Enzymol. 116:441–447 (1985), and Matthews, et al., pgs. 221–225, in Clemens, et al., eds., Lymphokines and Interferons: A Practical Approach (IRL Press, Washington, D.C., 1987). Human IL-2 and GM-CSF can be assayed with factor dependent cell lines CTLL-2 and KG-1, available from the ATCC under accession numbers TIB 214 and CCL 246, respectively. Human IL-3 can be assayed by its ability to stimulate the formation of a wide range of hematopoietic cell colonies in soft agar cultures, e.g., as described by Metcalf, The Hemopoietic Colony Stimulating Factors (Elsevier, Amsterdam, 1984). INF-$\gamma$ can be quantified with anti-viral assays, e.g., Meager, pgs. 129–147, in Clemens, et al., eds. (cited above).

Cytokine mRNA production can be measured and analyzed by cytoplasmic dot hybridization as described by White, et al., J. Biol. Chem. 257:8569–8572 (1982) and Gillespie, et al., U.S. Pat. No. 4,483,920. Accordingly, these references are incorporated by reference. Other approaches include dot blotting using purified RNA, e.g., chapter 6, in Hames, et al., eds., Nucleic Acid Hybridization A Practical Approach (IRL Press, Washington, D.C., 1985).

In some cases, samples to be tested for IL-10 activity may be pretreated to remove predetermined cytokines that might interfere with the assay. For example, IL-2 increases the production of IFN-$\gamma$ in some cells. Thus, depending on the helper T cells used in the assay, IL-2 should be removed from the sample being tested. Such removals are conveniently accomplished by passing the sample over a standard anti-cytokine affinity column.

For convenience, units of IL-10 activity are defined in terms of the ability of IL-10 to augment the IL-4-induced proliferation of MC/9 cells, which are described in U.S. Pat. No. 4,559,310 and available from the ATCC under accession number CRL 8306. 1 unit/ml is defined as the concentration of IL-10 which gives 50% of maximum stimulation of MC/9 proliferation above the level of IL-4 in the following assay. Prepare multiple duplicate dilutions of IL-4 and IL-10 in 50 µl of medium per well in a standard microtiter plate. For example, medium consists of RPMI 1640, 10% fetal calf serum, 50 µM 2-mercaptoethanol, 2 mM glutamine, penicillin (100 U/L) and streptomycin (100 µg/L). Add IL-4, 25 µl/well of 1600 U/ml (400 U/ml final) diluted in medium and incubate overnight, e.g., 20–24 hours. $^3$H-thymidine (e.g., 50 µCi/ml in medium) is added at 0.5–1.0 µCi/well and the cells are again incubated overnight, after which cells are harvested and incorporated radioactivity measured.

II. Purification and Pharmaceutical Compositions

When polypeptides of the present invention are expressed in soluble form, for example as a secreted product of transformed yeast or mammalian cells, they can be purified according to standard procedures of the art, including steps of ammonium sulfate precipitation, ion exchange chromatography, gel filtration, electrophoresis, affinity chromatography, and/or the like, e.g., "Enzyme Purification and Related Techniques," Methods in Enzymology, 22:233–577 (1977), and Scopes, Protein Purification: Principles and Practice (Springer-Verlag, New York, 1982) provide guidance in such purifications. Likewise, when polypeptides of the invention are expressed in insoluble form, for example as aggregates, inclusion bodies, or the like, they can be purified by standard procedures in the art, including separating the inclusion bodies from disrupted host cells by centrifugation, solubilizing the inclusion bodies with chaotropic and reducing agents, diluting the solubilized mixture, and lowering the concentration of chaotropic agent and reducing agent allowing the polypeptide to take on a biologically active conformation. The latter procedures are disclosed in the following references, which are incorporated by reference: Winkler, et al., Biochemistry, 25:4041–4045 (1986); Winker, et al., Biotechnology, 3:992–998 (1985); Koths, et al., U.S. Pat. No. 4,569,790; and European patent applications 86306917.5 and 86306353.3. Recombinant methods allow production of proteins with either fusion products, which allow for purification, or epitope tags, which also assist in purification or detection. Specific means may be engineered into the construct to allow for removal of extraneous sequences. It is believed that the amino terminus of the IL-10 molecule is important for binding to its receptor, so it will usually be preferred to make fusions at the carboxy terminus.

As used herein, "effective amount" means an amount sufficient to provide the desired result, e.g., in an appropriate context, to reduce or prevent tissue rejection. Preferably, such amount will have minimal negative side effects. The effective amount for a particular patient may vary depending on such factors as the state, type, and amount of tissue transplanted, the overall health of the patient, method of administration, the severity of side-effects, and the like. Generally, IL-10 is administered as a pharmaceutical composition comprising an effective amount of IL-10 and a pharmaceutical carrier. A pharmaceutical carrier can be any compatible, non-toxic substance suitable for delivering the compositions of the invention to a patient. Generally, compositions useful for parenteral administration of such drugs are well known, e.g., Remington's Pharmaceutical Science, 15th Ed. (Mack Publishing Company, Easton, Pa. 1980); Gilman, et al. (eds.) Goodman and Gilman's: The Pharmacological Bases of Therapeutics (Permagon Press). Alternatively, compositions of the invention may be introduced into a patient's body by implantable or injectable drug delivery system, e.g., Urquhart et al., Ann. Rev. Pharmacol. Toxicol., Vol. 24, pgs. 199–236 (1984); Lewis, ed. Controlled Release of Pesticides and Pharmaceuticals (Plenum Press, New York, 1981); U.S. Pat. No. 3,773,919; U.S. Pat. No. 3,270,960; and the like.

When administered parenterally, the IL-10 is preferably formulated in a unit dosage injectable form (solution, suspension, emulsion) in association with a pharmaceutical carrier. See, e.g., Avis, et al. (eds.) Pharmaceutical Dosage Forms: Parenteral Medications (Dekker, N.Y., 1993); Lieberman, et al. (eds.) Pharmaceutical Dosage Forms: Tablets (Dekker, N.Y., 1990); and Lieverman, et a. (eds.) Pharmaceutical Dosage Forms: Disperse Systems (Dekker, N.Y., 1990). Examples of such carriers include normal saline, Ringer's solution, dextrose solution, and Hank's solution. Nonaqueous carriers such as fixed oils and ethyl oleate may also be used. A preferred carrier is 5% dextrose/saline. The carrier may contain minor amounts of additives such as substances that enhance isotonicity and chemical stability, e.g., buffers and preservatives. The IL-10 is preferably formulated in purified form substantially free of aggregates and other proteins at a concentration in the range of about 5 to 20 µg/ml. Preferably, IL-10 is administered by continuous infusion so that an amount in the range of about 50–800 µg is delivered per day (i.e., about 1–16 µg/kg/day). The daily infusion rate may be varied based on monitoring of side effects and blood cell counts.

III. Th3 Cells

The present invention also provides antigen-specific anergic T cells, which fail to respond in an antigen-specific fashion to representation of the antigen. See, e.g., Paul (ed.) Fundamental Immunology, Raven Press (1993). This antigen-specific anergy can be distinguished from generic tolerance in that many forms of tolerance result from blockage of the T cell receptor signal at the cell surface and thus will be independent of the antigen. The antigen-specific anergy described here, as shown below, does not appear to affect the $Ca^{++}$ dependent signaling pathway, e.g., the Ras/Raf/MAPK pathway, of signal transduction, since the T cell receptor and the $Ca^{++}$ flux responses to antigen engagement remain. Moreover, the anergy does not require constant administration of an agent to block the early stages of signal transduction, e.g., necessary to actively block T cell receptor function. The anergy seems to be maintained for a period of time, e.g., for at least about 14 days, 18 days, 21 days, 24 days, etc. It may remain for weeks, months, and preferably years.

The antigen-specific anergy described herein can be produced by presenting a combination of IL-10 with antigen. The components are presented to the immune system, or cells thereof, for adequate periods of time, often completely coextensive, though the period may not necessarily require both components for the entire duration. This period will typically be at least about 5 days, more typically at least about 7 days, preferably at least about 9–11 days, and more preferably at least about 13–15 days or more. The dosing of the IL-10 and or antigen may depend on various factors, including, e.g., the antigen, the duration of the periods, whether both are present, whether the IL-10 is presented before antigen, etc. Preferably, both components are presented for at least about 7 days.

IL-10 has been described above. Other means to effect higher IL-10 levels include stimulation of endogenous IL-10, including, e.g., LPS, TNF-α, IL-12, BCG1 (Bacillus Calmett Guerin), Corynebacterium parvus, poly I-C (alloadjuvant for activating monocytes and macrophages), etc. Agonistic antibodies to the IL-10 receptor may also function as an agonist.

Various types of antigens exist for which antigen-specific T cell anergy may be important. Both alloantigens and self antigens are presented in the context of MHC. See, e.g., Paul (ed.) Fundamental Immunology. Other antigens for which T cell anergy may be important include soluble antigens, e.g., soluble proteins or fragments of insoluble complexes, particulate antigens, e.g., bacteria or parasites, and allergens. Various forms of antigen will be presented with IL-10 to induce antigen-specific antigen, as described.

Antigen-specific anergy involves a mechanism which is distinguishable from certain other forms of non-responsiveness. These Th3 cells appear to be memory T cells, e.g., CD45+, in contrast to naive T cells, e.g., CD45RA+ or CD45RO−. In particular, this antigen-specific anergy reflects the inability of these antigen-specific cells to respond to subsequent restimulation with the specific antigen, typically with IL-2. When antigen-specific anergic cells are restimulated with IL-2 and antigen at normal levels, the cells fail either to proliferate significantly, or to produce the cytokines. However, the anergic population containing Th3 cells, when stimulated in a subsequent presentation with anti-CD3 antibodies (at about 100 ng/ml) will stimulate only the growth of the Th0, Th1, and Th2 T cells. Analysis of the cytokine production by these defined T helper subset cells is well known when stimulated at the higher levels of anti-CD3 of about 1–10 μg/ml. However, at this level of stimulation, the Th3 cells seem not to be stimulated to proliferate or produce cytokines. The Th3 cells seem to be stimulated both to proliferate and produce cytokines with anti-CD3 antibodies at about 100–700 μg/ml. Thus, if the cells in a mixed population are diluted out to single cells in wells, all of the T helper subsets will be stimulated with anti-CD3 antibodies at the 100–700 μg/ml, which allows evaluation of the cytokine production profiles of the different subsets Th0, Th1, Th2, and Th3, as described.

The response to subsequent anti-CD3 antibody general stimulation, e.g., through the T cell receptor/Cd3 complex, can be quantitated by various methods. As described above, various cytokines may be measured according to biological activity. Preferably, a quantitation of accumulated protein may be determined by various immuno- or other assays, as described below. Alternatively, mRNA production may be measured to establish levels of stimulation of transcription.

Typically, cytokines are measured after accumulation of secreted protein over set periods of time upon subsequent, e.g., secondary or subsequent, stimulation using anti-CD3 antibody (100–700 μg/ml). Thus, the time for accumulation is preferably at least about 24 h in a volume of about 1 ml, but may be longer, and may include other feeder cell layers, etc.

Cell proliferation after subsequent stimulation can be measured by standard methods. Often this includes measuring incorporation of nucleotides, but may also involve measuring cell numbers, cell volumes, etc.

While certain responses of tolerance characterized as anergy result from blockage of signaling at the T cell receptor (see Weiss and Littman Cell 76:263–274 (1994); Chan, et al. Ann. Rev. Immunol. 12:555–592 (1994); and Fraser, et al. Immunol. Today 14:357–362), the anergy described herein exists with functional T cell receptor. In particular, stimulation with anti-CD3 still results in a $Ca^{++}$ flux. But the antigen-specific T cells do not respond to the antigen stimulation in the normal manner, e.g., by production of cytokines and/or cell proliferation.

The anergy provided herein involves either a much lowered proliferative responsiveness to IL-2 and/or antigen, e.g., less than about 50% response, usually less than about 40% response, more usually less than about 30% response, preferably less than about 20%, and more preferably 10%, or less as compared to non-anergic cells. Alternatively, the stimulation required to induce a response requires much larger amounts of IL-2 and antigen, e.g., 5–50×, to elicit the equivalent proliferative response. The anergy also is reflected in a different cytokine production profile upon restimulation of clones with anti-CD3 antibodies. See below.

The measure of cytokine production is after restimulation of clones with the specific antigen, although more usually after generic stimulation with anti-CD3 (in vitro at about 10 μg/ml or more), which apparently activates through the T cell receptor. This stimulation results in a much attenuated cellular proliferation response, and a distinguishable cytokine production profile. Among the notable differences in cytokine production after restimulation and cloning are undetected IL-4 and high IL-10 production. See below, e.g., Table 7. The amount of anti-CD3 antibodies used can also affect the response, as indicated above.

Comparing the amounts of cytokines produced, note that the Th3 cell clones produce a different profile of cytokines from the Th0, Th1, or Th2 clones after anti-CD3 (10 μg/ml) stimulation. With respect to IL-2, these anergic Th3 cell clones produce less than about 30%, preferably less than about 10%, and typically less than about 2% of the corresponding Th0 or Th1 cell clones. For IL-4, these anergic Th3 cells produce less than about 30%, preferably less than about 10%, and typically less than about 1% of the corresponding Th0 or Th1 cell clones. For IL-5, these anergic Th3 cell clones produce about 10–20% of the corresponding Th0 cell clones, about 5–10% of the corresponding Th2 cell clones, and about 5–30× the corresponding Th1 cell clones. For IL-10, these anergic Th3 cells produce about 10–50× as much as corresponding Th0 or Th1 cell clones, and about 5–25× as much as corresponding Th2 cells. For IFN-γ, these anergic Th3 cells produce about 3–20× as much as corresponding Th2 cell clones, and comparable amounts, within a factor of about 2 or 3 of that produced by Th0 or Th1 cell clones. For TNF-α, these Th3 cell clones produce about 2–5× as much as Th0 or Th2 cell clones, and comparable amounts, within a factor of about 2 or 3, as Th1 cell clones. The anergic Th3 cell clones also produce only low levels of GM-CSF.

Note also that the duration of IL-10 with antigen can affect the extent of reversibility. While treatments over about 7 days leads to substantial irreversibility with normal amounts of IL-2 or anti-CD3 antibody (10 μg/ml); very high amounts of IL-2, antigen, or anti-CD3 antibody (e.g., 700 μg/ml) will tend to have a greater capacity to either attenuate or reverse the anergy.

IL-10 inhibited in a dose-dependent fashion the alloantigen-induced proliferative responses in primary mixed lymphocyte response. The suppressive effect was optimal when IL-10 was added at the beginning of the cultures suggesting that it acts on the early stages of T cell activation. The proliferative responses were enhanced in the presence of anti-IL-10 mAb, indicating that endogenously produced IL-10 suppresses proliferation in primary MLR. The inhibitory effects of IL-10 were observed irrespective of whether irradiated allogeneic peripheral blood mononuclear cells (PBMC), purified monocytes, or B cells were used as stimulator cells. The reduced proliferative responses were not restored by high concentrations of exogenous IL-2 indicating that the effects of IL-10 are not related to inhibition of IL-2 synthesis. Furthermore, the production of IL-2, IFN-γ, IL-6, GM-CSF, and TNF-α in primary MLR was diminished by IL-10 and enhanced in the presence of anti-IL-10 mAb. The strongest effects were observed on the production of IFN-γ. Although IL-10 reduces the proliferative responses, the ratio of $CD3^+CD4^+$ and $CD3^+CD8^+$ T cells remained the same in IL-10 treated and control cultures. However, the percentages of activated $CD3^+$ T cells as judged by $CD25^+$ and $HLA-DR^+$ expression were consistently reduced in the presence of IL-10.

h-IL-10 inhibits the synthesis of IFN-γ and granulocyte-macrophage colony stimulating factor (GM-CSF) induced in human PBMC by PHA, anti-CD3 mAb, and IL-2 (Bacchetta, et al., J. Immunol. 144:902 (1989); and Bevan, Immunol Today 5:128 (1984). This inhibition occurs at the transcriptional levels (Altmann, et al. Nature 338:512 (1989); Bacchetta, et al., supra). Murine IL-10 (m-IL-10) has pleiotropic activities on different cell types, including growth promoting effects on thymocytes (Chen, et al., J. Immunol. 147:528 (1991)), cytotoxic T cells (De Koster, et al., J. Exp. Med. 169:1191 (1989)), and mast cells (de Waal Malefyt, et al., J. Exp. Med. 174:1209 (1991)). m-IL-10 induces class II MHC antigen expression on B cells and sustains the viability of these cells (de Waal Malefyt, et al., J. Exp. Med. 174:915 (1991)). Furthermore, IL-10 inhibits cytokine production by macrophages (Bejarano, et al., Int. J. Cancer. 35:327 (1985); Fiorentino, et al., J. Exp. Med. 170:2081 (1989)). h- and m-IL-10 have extensive homology to BCRF-1, an open reading frame of the Epstein Barr virus (EBV) genome (Azuma, et al., J. Exp. Med. 175:353 (1992); Bacchetta, et al., J. Immunol. 144:902 (1989)). The protein product of BCRF-1, designated as viral IL-10 (v-IL-10), shares most properties with h- and m-IL-10 including CSIF activity on human and mouse T cells (Bacchetta, et al., supra; Bevan, M. J., supra).

h-IL-10 and v-IL-10 inhibit antigen specific proliferative responses by reducing the antigen presenting capacity of human monocytes via downregulation of class II MHC molecules (Figdor, et al., J. Immunol. Methods 68:68 (1984)). Moreover, IL-10 inhibits cytokine synthesis by LPS or IFN-γ activated monocytes, including CM-CSF, G-CSF, and the proinflammatory cytokines IL-1α, IL-1β, IL-6, IL-8, and TNF-α (Bejarano, et al., Int. J. Cancer. 35:327 (1985); Fiorentino, et al, supra.). Interestingly, LPS activated monocytes produce high levels of IL-10, and enhanced production of cytokines was observed in the presence of anti-IL-10 mAb indicating an autoregulatory effect of IL-10 on monokine production (Bejarano, et al., supra).

Alloreactivity reflects, at least in part, recognition of foreign MHC molecules plus antigenic peptides of various origin (Fiorentino, et al., *J. Immunol.* 146:3444 (1991); Fiorentino, et al., *J. Immunol.* 147:3815 (1991); Freedman, et al., *J. Immunol.* 139:3260 (1987); Go, et al., *J. Exp. Med.* 172:1625 (1990)). Moreover, alloreactive T cells may recognize conformational differences between MHC molecules largely independent of the peptides bound, or even on empty MHC molecules (Harding, et al., *Proc. Natl. Acad. Sci. USA* 87:5553 (1990); Hsu, et al., *Science* 250:830 (1990); Julius, et al., *Eur. J. Immunol.* 3:645 (1973)). IL-10 inhibits allospecific proliferative responses, and cytokine production. In addition, the reduced proliferative responses could not be restored by exogenous IL-2.

Thus, the present invention provides means to generate large quantities of alloantigen specific Th3 cells by stimulating host derived $CD4^+$ T cells with donor derived irradiated PBMC in the presence of IL-10, e.g., for minimally at least about 3 days, preferably at least about 5 days, more preferably at least about 7 days, and in certain embodiments 9, 11, 13, 15, or more days. These cells can be administered prior or simultaneously with the transplant (organ or bone marrow). The transplant event and/or therapy may be with or without administration of IL-10.

The above cell therapy can be extended to treat other chronic diseases causing by antigens, such as gliadin (e.g., gluten) for the treatment of coeliac disease, allergens for the treatment of chronic allergic diseases (asthma, atopic dermatitis, rhinitis), or GAD (glutamic acid decarboxylase) or insulin for the treatment of diabetes.

In addition, this may provide treatment for inappropriate sensitivity to many other potential autoantigens. The cells or treatment may provide means for induction of long term tolerance and Th3 cell development in vivo. Long term, e.g., 5–15 day treatment with IL-10 may enhance in vivo production of anergy, with copresentation of appropriate MHC antigens, e.g., with class I or class II, or other soluble antigens.

The invention also provides means for administration of IL-10 in order to induce antigen specific Th3 cells and long term antigen specific tolerance in vivo for the treatment of diseases with undesired T-cell activation, e.g., in transplant rejection, graft versus host disease, parasitic diseases, chronic inflammatory diseases such as Crohn's disease, colitis, chronic inflammatory eye diseases, chronic inflammatory lung diseases, and chronic inflammatory liver diseases. See, e.g., Frank, et al. (eds.) Samter's Immunologic Diseases, Little, Brown, Boston, Mass.

In other contexts, it may be useful to administer of IL-10 in order to induce autoantigen specific Th3 cells and autoantigen specific tolerance in vivo for the treatment of autoimmune diseases such as rheumatoid arthritis, diabetes, multiple sclerosis.

In many embodiments, the IL-10 should be typically administered for a minimum of 5–15 days, preferably at least about 7 days.

All references cited herein are incorporated herein by reference to the same extent as if each individual reference, e.g., publication or patent application, was specifically and individually indicated to be incorporated by reference.

EXAMPLES

The following examples serve to illustrate the present invention. Selection of vectors and hosts as well as the concentration of reagents, temperatures, and the values of other variable parameters are only to exemplify applications of the present: invention and the claimed embodiments are not to be limited to the specific embodiments described herein.

Some of the standard methods are described or referenced, e.g., in Maniatis, et al. (1982) *Molecular Cloning, A Laboratory Manual* Cold Spring Harbor Laboratory, Cold Spring Harbor Press; Sambrook, et al. (1989) *Molecular Cloning: A Laboratory Manual* (2d ed.), vols. 1–3, CSH Press, NY; Ausubel, et al., *Biology*, Greene Publishing Associates, Brooklyn, N.Y.; or Ausubel, et al. (1987 and Supplements) *Current Protocols in Molecular Biology* Greene/Wiley, New York; Innis, et al. (eds.)(1990) *PCR Protocols: A Guide to Methods and Applications* Academic Press, N.Y. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology* vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, N.Y.; and Crowe, et al. (1992) *QIAexpress: The High Level Expression & Protein Purification System* QIAGEN, Inc., Chatsworth, Calif.

Fluorescent activated cell sorting was performed using standard methods on a Becton-Dickinson FACStar PLUS. See, e.g., Shapiro (1988) *Practical Flow Cytometry* (2d ed.) Alan Liss, New York.

Example 1
Expression of Human CSIF in a Bacterial Host

A synthetic human CSIF gene is assembled from a plurality of chemically synthesized double stranded DNA fragments to form an expression vector designated TAC-RBS-hCSIF. Cloning and expression are carried out in a standard bacterial system, for example, *E. coli* K-12 strain JM101, JM103, or the like, described by Vieira and Messing, in Gene 19:259–268 (1982). Restriction endonuclease digestions and ligase reactions are performed using standard protocols, e.g., Maniatis, et al., Molecular Cloning: A Laboratory Manual (Cold Spring Harbor Laboratory, New York, 1982). See also, Ausubel (ed) Current Protocols in Molecular Biology (Greene/Wiley, NY, 1987 and periodic supplements); Sambrook, et al. Molecular Cloning: A Laboratory Manual (2d ed., Cold Spring Harbor Laboratory, New York, 1989).

The alkaline method (Maniatis et al., cited above) is used for small scale plasmid preparations. For large scale preparations, a modification of the alkaline method is used in which an equal volume of isopropanol is used to precipitate nucleic acids from the cleared lysate. Precipitation with cold 2.5 M ammonium acetate is used to remove RNA prior to cesium chloride equilibrium density centrifugation and detection with ethidium bromide.

For filter hybridizations Whatman 540 filter circles are used to lift colonies which are then lysed and fixed by successive treatments with 0.5 M NaOH, 1.5 M NaCl; 1 M Tris HCl pH 8.0, 1.5 M NaCl (2 min each); and heating at 80° C. (30 min). Hybridizations are in 6×SSPE, 20% formamide, 0.1% sodium dodecylsulphate (SDS), 100 µg/ml E. coli tRNA at 42° C. for 6 hrs using $^{32}$P-labelled (kinased) synthetic DNAs. (20×SSPE is prepared by dissolving 174 g of NaCl, 27.6 g of NaH$_2$PO$_4$9H$_2$O, and 7.4 g of EDTA in 800 ml of H$_2$O, pH is adjusted to 7.4 with NaOH, volume is adjusted to 1 liter, and sterilized by autoclaving). Filters are washed twice (15 min, room temperature) with 1×SSPE, 0.1% SDS. After autoradiography (Fuji RX film), positive colonies are located by aligning the regrown colonies with the blue-stained colonies on the filters. DNA is sequenced by the dideoxy method, Sanger, et al. Proc. Natl. Acad. Sci. 74:5463 (1977). Templates for the dideoxy reactions are either single stranded DNAs of relevant regions recloned into M13mp vectors, e.g., Messing, et al., Nucleic Acids Res. 9:309 (1981), or double-stranded DNA prepared by the minialkaline method and denatured with 0.2 M NaOH (5 min, room temperature) and precipitated from 0.2 M NaOH, 1.43 M ammonium acetate by the addition of 2 volumes of ethanol. DNA is synthesized by phosphoramidite chemistry using Applied Biosystems 380A synthesizers. Synthesis, deprotection, cleavage, and purification (7M urea PAGE, elution, DEAE-cellulose chromatography) are performed, e.g., as described in the Applied Biosystems 380A synthesizer manual.

Complementary strands of synthetic DNAs to be cloned (400 ng each) are mixed and phosphorylated with polynucleotide kinase in a reaction volume of 50 µl. This DNA is ligated with 1 µg of vector DNA digested with appropriate restriction enzymes, and ligations are in a volume of 50 µl at room temperature for 4 to 12 hours. Conditions for phosphorylation, restriction enzyme digestions, polymerase reactions, and ligation have been described (Maniatis et al., cited above). Colonies are scored for lacZ$^+$ (when desired) by plating on L agar supplemented with ampicillin, isopropyl-1-thio-beta-D-galactoside (IPTG) (0.4 mM) and 5-bromo-4-chloro-3-indolyl-beta-D-galactopyranoside (X-gal) (40 mg/ml).

Figure 2:
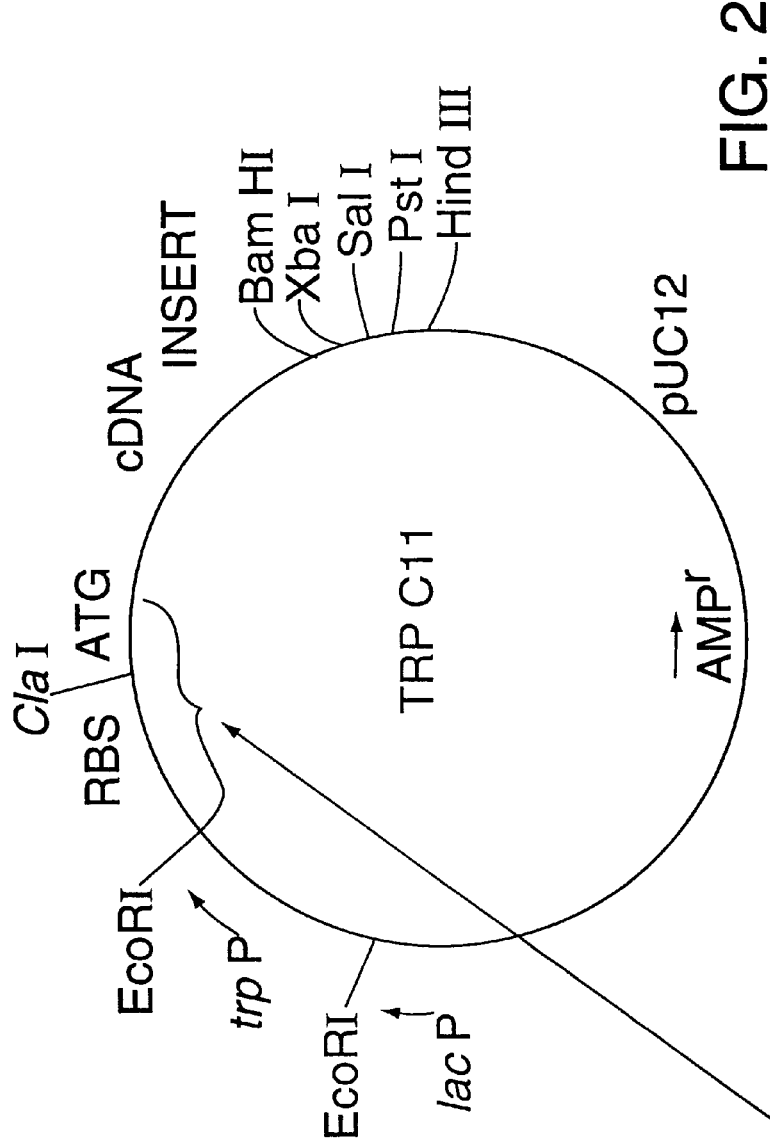
FIG. 2 shows a diagram of the vector TRP-Cll used for expressing IL-10 in bacteria. See SEQ ID NO: 26.

The TAC-RBS vector is constructed by filling-in with DNA polymerase the single BamHI site of the tacP-bearing plasmid pDR540 (Pharmacia). This is then ligated to unphosphorylated synthetic oligonucleotides (Pharmacia) which form a double-stranded fragment encoding a consensus ribosome binding site (RBS) GTAAGGAGGTTTAAC (SEQ ID NO:5). After ligation, the mixture is phosphorylated and re-ligated with the SstI linker ATGAGCTCAT (SEQ ID NO: 6). This complex was then cleaved with SstI and EcoRI, and the 173 bp fragment isolated via polyacrylamide gel electrophoresis (PAGE) and cloned into EcoRI-SstI restricted pUC19 (Pharmacia) as described below. The sequence of the RBS-ATG-polylinker regions of the final construction (called TAC-RBS) is shown in FIG. 2.

The synthetic IL-10 gene is assembled into a pUC19 plasmid in eight steps. At each step inserts free of deletions and/or inserts can be detected after cloning by maintaining the lacZ(a) gene of pUC19 in frame with the ATG start codon inserted in step 1. Clones containing deletion and/or insertion changes can be eliminated by scoring for blue colonies on L-ampicillin plates containing X-gal and IPTG. Alternatively, at each step sequences of inserts can be readily confirmed using a universal sequencing primer on small scale plasmid DNA preparations, e.g., available from Boehringer Mannheim.

In step 1 the TAC-RBS vector is digested with SstI, treated witlh T4 DNA polymerase (whose 3' exonuclease activity digests the 3' protruding strands of the SstI cuts to form blunt end fragments), and after deactivation of T4 DNA polymerase, treated with EcoRI to form a 173 base pair (bp) fragment containing the TAC-RBS region and having a blunt end at the ATG start codon and the EcoRI cut at the opposite end. Finally, the 173 bp TAC-RBS fragment is isolated.

In step 2 the isolated TAC-RBS fragment of step 1 is mixed with EcoRI/KpnI digested plasmid pUC19 and synthetic fragment 1A/B which, as shown below, has a blunt end at its upstream terminus and a staggered end corresponding to a KpnI cut at its downstream terminus. This KpnI end is adjacent to and downstream of a BstEII site. The fragments are ligated to form the pUC19 of step 2.

In step 3 synthetic fragments 2A/B and 3A/B (shown below) are mixed with BstEII/SmaI digested pUC19 of step 2 (after amplification and purification) and ligated to form pUC19 of step 3. Note that the downstream terminus of fragment 3A/B contains extra bases which form the SmaI blunt end. These extra bases are cleaved in step 4. Also, fragments 2A/B and 3A/B have complementary 9 residue single stranded ends which anneal upon mixture, leaving the upstream BstEII cut of 2A/B and the downstream blunt end of 3A/B to ligate to the pUC19.

In step 4 AflII/XbaI digested pUC19 of step 3 (after amplification and purification) is repurified, mixed with synthetic fragment 4A/B (shown below), and ligated to form the pUC19 of step 4.

In step 5 XbaI/SalI digested pUC19 of step 4 (after amplification and purification) is mixed with synthetic fragment 5A/B (shown below) and ligated to form the pUC19 of step 5. Note that the SalI staggered end of fragment 5A/B is eliminated by digestion with HpaI in step 6.

In step 6 HpaI/PstI digested pUC19 of step 5 (after amplification and purification) is mixed with synthetic 6A/B (shown below) and ligated to form the pUC19 of step 6.

In step 7, ClaI/SphI digested pUC19 of step 6 (after amplification and purification) is mixed with synthetic fragment 7A/3 (shown below) and ligated to form the pUC19 of step 7.

In step 8 MluI/HindIII digested pUC19 of step 7 (after amplification and purification) is mixed with synthetic fragments 8A/B and 9A/B and ligated to form the final construction. The final construction is inserted into *E. coli* K-12 strain JM101, e.g., available from the ATCC under accession number 33876, by standard techniques. After culturing, protein is extracted from the JM101 cells and dilutions of the extracts are tested for biological activity.

```
AGCCCAGGCC AGGGCACCCA GTCTGAGAAC AGCTGCACCC ACTTCCCAGG-
TCGGGTCCGG TCCCGTGGGT CAGACTCTTG TCGACGTGGG TGAAGGGTCCtAACCggtac                      SEQ ID NO:7
aTTGGc                          SEQ ID NO:8
                             Fragment 1A/B GtAACCTGCC TAACATGCTT CGAGATCTCC GAGATGCCTT CAGCAGAGTG-
     GACGG ATTGTACGAA GCTCTAGAGG CTCTACGGAA GTCGTCTCAC- AAGACTTTCTTT                    SEQ ID NO:9
TTC                             SEQ ID NO:10
                             Fragment 2A/B CAAATGAAGG ATCAGCTGGA CAACTTGTTc TtAAG  SEQ ID NO:11
TGAAAGAAA GTTTACTTCC TAGTCGACCT GTTGAACAAg AaTTC  SEQ ID NO:12
                             Fragment 3A/B GAGTCCTTGC TGGAGGACTT TAAGGGTTAC CTGGGTTGCC AAGCCTTGTC TGAGATGATC-
CTCAGGAACG ACCTCCTGAA ATTCCCAATG GACCCAACGG TTCGGAACAG ACTCTACTAG- CAGTTTTAt                       SEQ ID NO:13
GTCAAAATaG AtC                  SEQ ID NO:14
                             Fragment 4A/B CTaGAGGAGG TGATGCCCCA AGCTGAGAAC CAAGACCCAG ACATCAAGGC-
GAtCTCCTCC ACTACGGGGT TCGACTCTTG GTTCTGGGTC TGTAGTTCCG- GCATCTtAAC g                    SEQ ID NO:15
CGTACAaTTG cagct                SEQ ID NO:16
                             Fragment 5A/B AACTCCCTGG GGGAGAACCT GAAGACCCTC AGGCTGAGGC TACGGCGCTG-
TTGAGGGACC CCCTCTTGGA CTTCTGGGAG TCCGACTCCG ATGCCGCGAC- TCATCGATct gca                  SEQ ID NO:17
AGTAGCTAg                       SEQ ID NO:18
                             Fragment 6A/B CGATTTCTTC CCTGTCAAAA CAAGAGCAAG GCCGTGGAGC AGGTGAAGAA-
   TAAAGAAG GGACAGTTTT GTTCTCGTTC CGGCACCTCG TCCACTTCTTcGCgTgcatg                      SEQ ID NO:19
gCGcAc                          SEQ ID NO:20
                             Fragment 7A/B CGCGTTTAAT AATAAGCTCC AAGACAAAGG CATCTACAAA GCCAT-
    AAATTA TTATTCGAGG TTCTGTTTCC GTAGATGTTT CGGTA- GAGTGAGTTT GAC                  SEQ ID NO:21
CTCA                            SEQ ID NO:22
                             Fragment 8A/B ATCTTCATCA ACTACATAGA AGCCTACATG ACAATGAAGA-
CTCAAACTG TAGAAGTAGT TGATGTATCT TCGGATGTAC TGTTACTTCT- TACGAAACTC A                    SEQ ID NO:23
ATGCTTTGAC Ttcga                SEQ ID NO:24
                             Fragment 9A/B
```

(Lower case letters indicate that a base differs from that of the native sequence at the same position.)

Example 2
Expression of vIL-10 in COS 7 Monkey Cells

Figure 1:
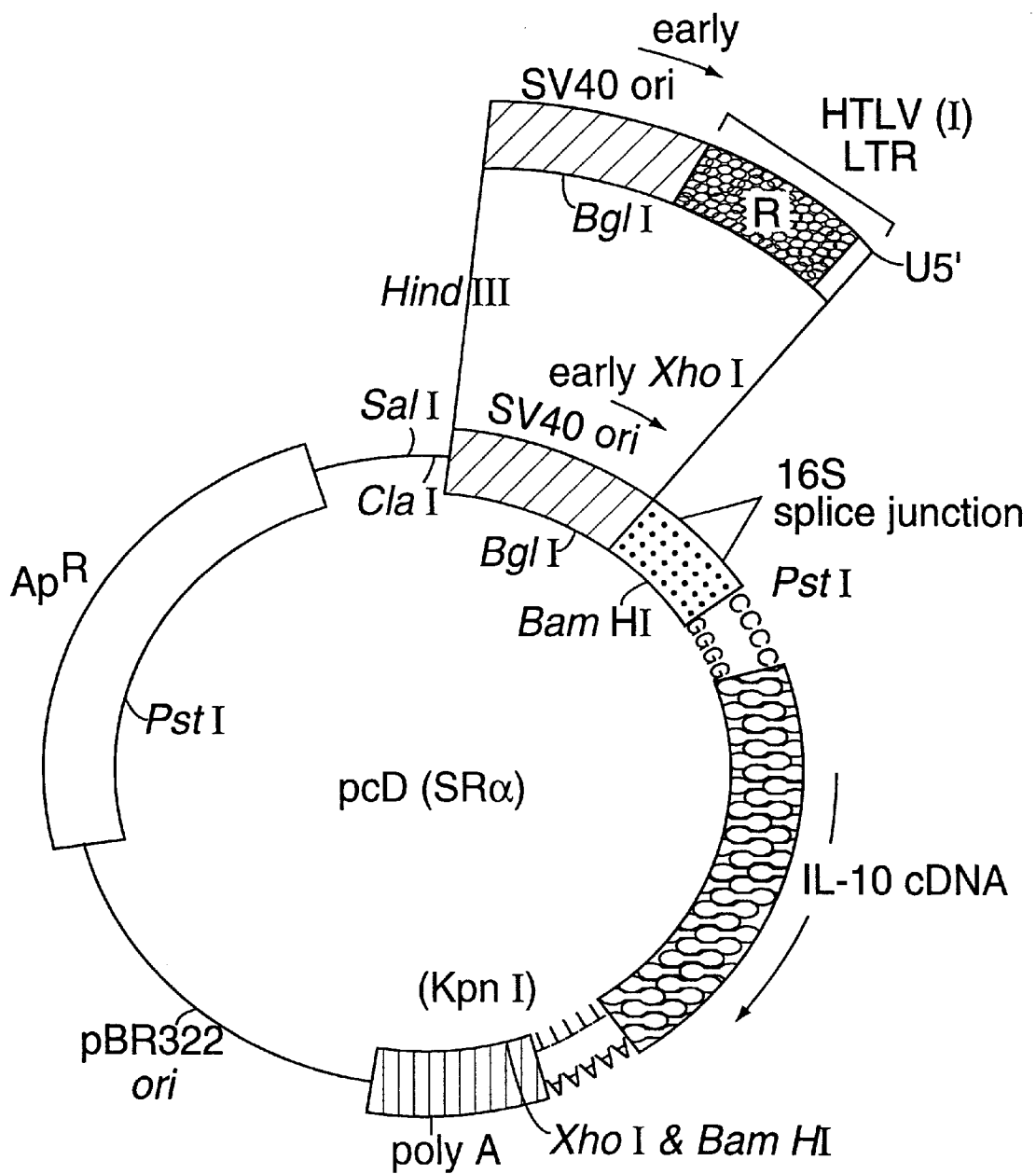
FIG. 1 shows a diagram of the vector pcD(SRα) used for expressing IL-10 in mammalian cells.

A gene encoding the open reading frame for vIL-10 was amplified by polymerase chain reaction using primers that allowed later insertion of the amplified fragment into an EcoRI-digested pcD(SRa) vector (FIG. 1). The coding strand of the inserted fragment is shown below (the open reading frame being given in capital letters).

```
aattcATGGA GCGAAGGTTA GTGGTCACTC TGCAGTGCCT

GGTGCTGCTT TACCTGGCAC CTGAGTGTGG AGGTACAGAC

CAATGTGACA ATTTTCCCCA GACCTAAGAG ATGCCTTCAG

TCGTGTTAAA ACCTTTTTCC AGACAAAGGA CGAGGTAGAT

AACCTTTTGC TCAAGGAGTC TCTGCTAGAG GACTTTAAGG

ATGCCAGGCC CTGTCAGAAA TGATCCAATT CTACCTGGAG

GAAGTCATGC CACAGGCTGA AACCAGGAC  CCTGAAGCCA

AAGACCATGT CAATTCTTTG GGTGAAAATC TAAAGACCCT

ACGGCTCCGC CTGCGCAGGT GCCACAGGTT CCTGCCGTGT

GAGAACAAGA GTAAAGCTGT GGAACAGATA AAAAATGCCT

TTAACAAGCT GCAGGAAAAA GGAATTTACA AAGCCATGAG

TGAATTTGAC ATTTTTATTA ACTACATAGA AGCATACATG

ACAATTAAAG CCAGGTGAg
(see SEQ ID NO:25)
```

Clones carrying the insert in the proper orientation were identified by expression of vIL-10 and/or the electrophoretic pattern of restriction digests. One such vector carrying the vIL-10 gene was designated pBCRF1(SRα) and was deposited with the ATCC under accession number 68193 on Dec. 20, 1989. PBCRF1(SRα) was amplified in *E. coli* MC1061, isolated by standard techniques, and used to transfect COS7 monkey cells as follows: One day prior to transfection, approximately 1.5×10⁶ COS7 monkey cells were seeded onto individual 100 mm plates in Dulbeccols modified Eagle medium (DME) containing 5% fetal calf serum (FCS), and 2 mM glutamine. To perform the transfection, COS7 cells were removed from the dishes by incubation with trypsin, washed twice in serum-free DME, and suspended to 10⁷ cells/ml in serum-free DME. A 0.75 ml aliquot was mixed with 20 μg DNA and transferred to a sterile 0.4 cm electroporation cuvette. After 10 minutes, the cells were pulsed at 200 volts, 96 μF in a BioRad Gene Pulser unit. After another 10 minutes, the cells were removed from the cuvette and added to 20 ml of DME containing 5% FCS, 2 mM glutamine, penicillin, streptomycin, and gentamycin. The mixture was aliquoted to four 100 mm tissue culture dishes. After 12–24 hours at 37° C., 5% $CO_2$, the medium was replaced with similar medium containing only 1% FCS and the incubation continued for an additional 72 hours at 37° C., 5% $CO_2$, after which the medium was collected and assayed for its ability to inhibit IFN-γ synthesis.

10 ml aliquots of freshly isolated PBLs (about 2×10⁶ cells/ml) were incubated at 37° C. with PHA (100 ng/ml) in medium consisting of (i) 90% DME supplemented with 5% FCS and 2 mM glutamine, and (ii) 10% supernatant from COS 7 cells previously transfected with pBCRF1(SRα). After 24 hours the cells and supernatants were harvested to assay for the presence of either IFN-γ mRNA or IFN-γ protein, respectively. Controls were treated identically, except that the 10% supernatant was from COS 7 cultures previously transfected with a plasmid carrying an unrelated cDNA insert. The vIL-10-treated samples exhibited about a 50% inhibition of IFN-γ synthesis relative to the controls.

Example 3

Expression of vIL-10 in *Escherichia coli*

A gene encoding the following mature vIL-10 may be expressed in *E. coli*.

```
Thr Asp Gln Cys Asp Asn Phe Pro Gln Met Leu Arg Asp Leu Arg

Asp Ala Phe Ser Arg Val Lys Thr Phe Gln Thr Lys Asp Glu

Val Asp Asn Leu Leu Leu Lys Glu Ser Leu Leu Glu Asp Phe Lys

Gly Tyr Leu Gly Cys Gln Ala Leu Ser Glu Met Ile Gln Phe Tyr

Leu Glu Glu Val Met Pro Gln Ala Glu Asn Gln Asp Pro Glu Ala

Lys Asp His Val Asn Ser Leu Gly Glu Asn Leu Lys Thr Leu Arg

Leu Arg Leu Arg Arg Cys His Arg Phe Leu Pro Cys Glu Asn Lys

Ser Lys Ala Val Glu Gln Ile Lys Asn Ala Phe Asn Lys Leu Gln

Glu Lys Gly Ile Tyr Lys Ala Met Ser Glu Phe Asp Ile Phe Ile

Asn Tyr Ile Glu Ala Tyr Met Thr Ile Lys Ala Arg. (see SEQ ID NO:4).
```

The cDNA insert of pBCRF1(SRα) is recloned into an M13 plasmid where it is altered twice by site-directed mutagenesis: first to form a ClaI site at the 5' end of the coding region for the mature vIL-10 polypeptide, and second to form a BamHI site at the 3' end of the coding region for the mature vIL-10 polypeptide. The mutated sequence is then readily inserted into the TRPCll expression vector described below.

The TRPCll vector was constructed by ligating a synthetic consensus RBS fragment to ClaI linkers (ATGCAT) and by cloning the resulting fragments into ClaI restricted pMT11hc (which had been previously modified to contain the ClaI site). PMT11hc is a small (2.3 kilobase) high copy, $AMP^R$, $TET^S$ derivative of pBR322 that bears the πVX plasmid EcoRI-HindIII polylinker region. (πVX is described by Maniatis, et al., Molecular Cloning: A Laboratory Manual, Cold Spring Harbor Laboratory, 1982). This was modified to contain the ClaI site by restricting pMT11hc with EcoRI and BamHI, filling in the resulting sticky ends, and ligating with ClaI linker (CATCGATG), thereby restoring the EcoRI and BamHI sites and replacing the SmaI site with a ClaI site. One transformant from the TRPCll construction had a tandem RBS sequence flanked by ClaI sites. One of the ClaI sites and part of the second copy of the RBS sequence were removed by digesting this plasmid with PstI, treating with Bal31 nuclease, restricting with EcoRI, and treating with T4 DNA polymerase in the presence of all four deoxynucleotide triphosphates. The resulting 30–40 bp fragments were recovered via PAGE and cloned into SmaI restricted pUC12. A 248 bp $E.$ $coli$ trpP-bearing EcoRI fragment derived from pKC101 (described by Nichols, et al. in Methods in Enzymology 101:155 (Academic Press, N.Y. 1983)) was then cloned into the EcoRI site to complete the TRPCll construction, which is illustrated in FIG. 2. TRPCll is employed as a vector for vIL-10 by first digesting it with ClaI and BamHI, purifying it, and then mixing it in a standard ligation solution with the ClaI-BamHI fragment of the M13 containing the nucleotide sequence coding for the mature BCRF1. The insert-containing TRPCll, referred to as TRPCll-BCRF1, is propagated in $E.$ $coli$ K12 strain JM101, e.g., available from the ATCC under accession number 33876.

Example 4
IL-10 Effects on Generation of Alloreactivity in Primary MLR

Cells were cultured in Yssel's medium (Koulova, et al., $J.$ $Exp.$ $Med.$ 173:759 (1991)) supplemented with 10% pooled heat inactivated human AB serum.

The neutralizing anti-IL-10 mAb 19F1 was raised against v-IL-10 and efficiently neutralized h- and v-IL-10 (Bejarano, et al., Int. J. Cancer. 35:327 (1985)). The BB10 mAb which recognizes the IL-2R p55 chain was a kind gift of Dr. J. Wijdenes (CRTS, Bensancon, France). Murine anti-CD3 (anti-Leu-4, IgG1), anti-CD4 (Anti-Leu-3a, IgG1), anti-CD8 (anti-Leu-2a, IgG2a), anti-CD14 (anti-Leu-M3, IgG2b), anti-CD19 (anti-Leu-12, IgG1), anti-CD25 (anti-IL2R p55, IgG1), anti-CD56 (anti-Leu-19, IgG1), anti-HLA-DR (clone L243, IgG2a) mAb and control mAb of appropriate isotypes were obtained from Becton Dickinson (Mountain View, Calif.).

Buffy coat preparations were obtained from the Blood Bank of Stanford University Hospital. PBMC were isolated by density gradient centrifugation over Ficoll-hypaque (Pharmacia, Uppsala, Sweden).

For purification of T cells, PBMC were depleted of monocytes by plastic adherence and iron phagocytosis using the method of Linsley, et al., $J.$ $Exp.$ $Med.$ 173:721 (1991). Non-adherent cells were passed through nylon wool as described in MacNeil, et al., $J.$ $Immunol.$ 145:4167 (1990)). Thereafter, NK cells were removed by depletion with magnetic beads. Briefly, following staining with saturating concentrations of anti-CD56 mAb for 30 min at 4° C., cells were washed 2 times with Hank's balanced salt solution (HBSS), and subsequently rosetted with magnetic beads coated with sheep anti-mouse IgG (Dynabeads M-450 sheep anti-mouse IgG, Dynal AS, Oslo, Norway) at a bead to cell ratio of 40:1. The mixture was incubated for 30 min at 4° C. with gentle shaking before removal of rosetted cells with the magnetic particle concentrator according to the manufacturer's recommendations. The resulting cell preparations were >99% $CD3^+$, <1%, $CD14^+$, <1% $CD19^+$, <1% $CD56^+$.

For isolation of $CD14^+$monocytes, PBMC were stained with PE-conjugated CD14 mAb (Becton-Dickinson, Mountain View, Calif.), washed twice in HBSS and thereafter sorted in CD14+ and CD14− populations using a FACStar-Plus (Becton-Dickinson, Sunnyvale, Calif.). Reanalysis of the sorted populations showed that more than 99.5% of the purifiecl cells were $CD14^+$. In some experiments monocytes were isolated from peripheral blood by density centrifugation in a blood component separator, followed by centrifugal elutriation as described in detail by Moore, et al., Science 248:1230 (1990). These monocyte preparations were 95% pure, as judged by nonspecific esterase staining.

Purified B lymphocytes were obtained by magnetic bead depletion. Non-adherent PBMC were incubated with saturating concentrations of anti-CD3, CD4, CD8, CD14, and CD56 mAb for 30 min at 4° C. The cells were washed twice in HBSS and thereafter rosetted with magnetic beads coated with sheep anti-mouse IgG (Dynal, AS, Oslo, Norway) at a 40:1 bead to cell ratio. Subsequently, the rosetted cells were depleted as described above. The resulting population consisted of >98% $CD19^+$ cells.

For proliferation assays, PBMC or highly purified T cells ($1\times10^5$ cells/well), were stimulated by various irradiated (4000 rad) allogeneic stimulator cells. PBMC, $CD14^+$ monocytes, monocytes separated by centrifugal elutriation, or purified B lymphocytes were used as stimulator cells at R:S ratios of 1:1, 5:1, 5:1, and 3:1, respectively. Cultures were carried out in triplicate in 96-well flat-bottomed microtiter plates in the absence or in the presence of IL-10 in 200 $\mu$l medium.

Cultures were pulsed with [$^3$H]TdR during the last 10 hr of a 5 day incubation period and harvested onto fiberglass filters and the radioactivity determined by liquid scintillation counting. The results are expressed as cpm of [$^3$H]TdR incorporation and represent the means of multiple cultures.

For bulk cultures, PBMC or highly purified T cells were culturecl with irradiated allogeneic cells at the R:S ratios described above in 50 ml flasks at a concentration of $1\times10^6$ responder cells/ml in the presence or in the absence of 100 U/ml of IL-10. Five to six days later the supernatants were collected and frozen at −20° C. for determination of their cytokine contents, whereas the cells were recovered for phenotype analysis.

For fluorescence analysis, cells ($10^5$) recovered from the bulk cultures were incubated in V-bottomed microtiter plates (Flow Laboratories, city, state) with 10 $\mu$l of purified PE-conjugated mAb for 30 min at 4° C. In the double-labeling experiments, the cells were washed twice in 1% normal mouse serum after the FITC labeling, and a PE-conjugated mAb was added. The cells were washed twice with HBSS containing 1% BSA and 0.02M $NaN_3$ and thereafter analyzed on a FACScan.

For cytokine determinations, supernatants collected from bulk cultures at day 5 or 6 were assayed for the content of GM-CSF IFN-γ, TNF-α, IL-2, IL-4, IL-5, and IL-6 by lymphokine specific ELISA as described in Ohlen, et al, J. Immunol. 145:52 (1990). For the quantification of IL-2 production, cultures were carried out in the presence of 10 $\mu$g/ml of the anti-IL-2 receptor antibody, BB10, in order to minimize IL-2 consumption. Supernatants were harvested after 72 hr and the IL-2 levels were determined by specific ELISA. The sensitivity of the various ELISA were: 40 pg/ml for IL-4; 20 pg/ml for IL-2, IL-S and IL-6; 50 pg/ml for GM-CSF; and 100 pg/ml for TNF-α, and IFN-γ.

Figures 3A, 3B:
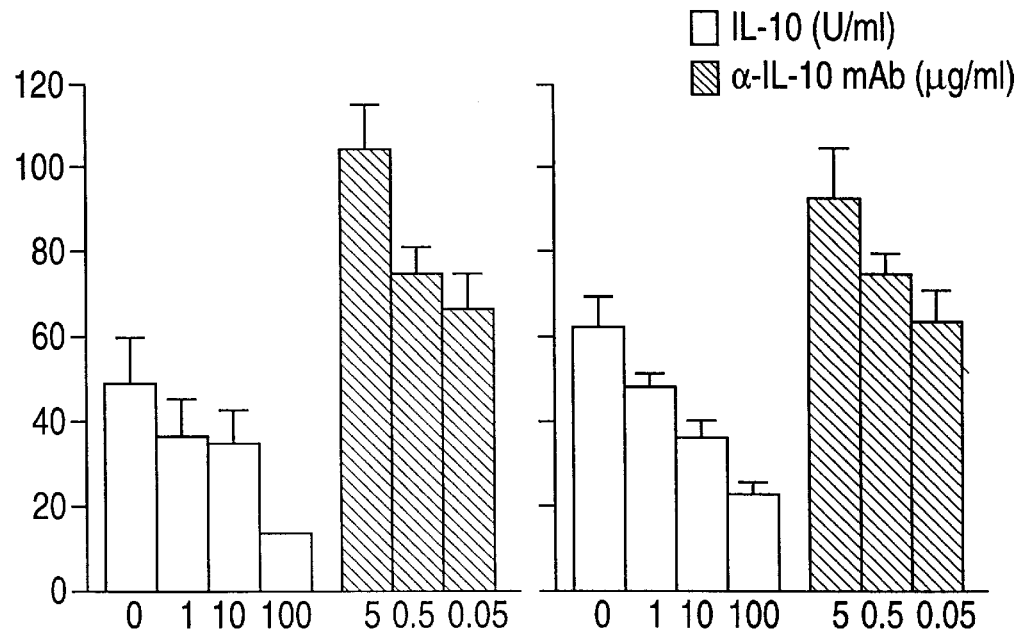
FIGS. 3A through 3C show histograms of the effects of endogenous and exogenous IL-10 on proliferative responses in mixed lymphocyte response.

To determine the effects of IL-10 on the proliferative responses in classical one-way primary MLR. PBMC were stimulated with irradiated allogeneic PBMC in the absence or presence of different concentrations of IL-10. In FIG. 3 it is shown that IL-10 inhibited the proliferative responses in a dose-dependent fashion.

As shown in FIG. 3, PBMC (1×10⁵/well) and allogeneic irradiated PBMC (1×10⁵/well) (PBMC donor A×irradiated PBMC donor B (A): PBMC donor B×irradiated PBMC donor A (B)) were cultured for 5 days in the presence of increasing concentrations of IL-10 (open bars) and anti-IL-10 mAb (solid bars). MLR were carried out in the absence (solid bars) or in the presence (hatched bars) of 100 U/ml IL-10 and increasing concentrations of anti-IL-10 mAb.

Figure 3C:
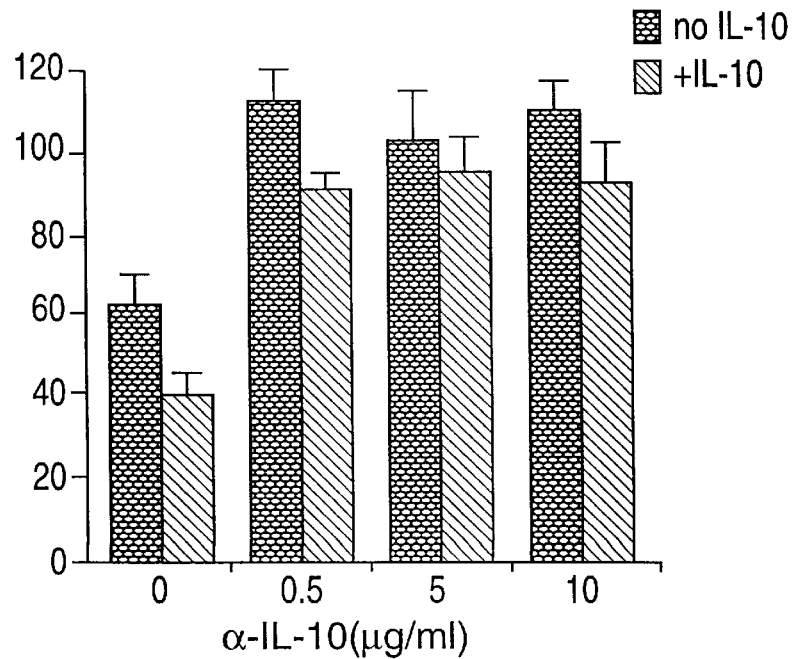

Significant inhibitory effects on proliferation were already observed at IL-10 concentrations as low as 1 U/ml, whereas maximal inhibitory effects (ranging from 33 to 95% inhibition in different experiments) were obtained at IL-10 concentrations of 100 U/ml. These inhibitory effects of IL-10 on PBMC proliferation were completely neutralized by the anti-IL-10 mAb indicating the specificity of the inhibition (FIG. 3C). The proliferative responses in MLR carried out in the presence of the neutralizing anti-IL-10 mAb were significantly enhanced, indicating that endogenously produced IL-10 is responsible for suppressing proliferative responses in primary MLC\R.

Recently it was demonstrated that IL-10 strongly reduces the antigen (Ag) presenting (AP) capacity of monocytes through downregulation of class II MHC antigens. In contrast, class II MHC expression and AP-capacity of EBV-transformed B cells (EBV-LCL) were not affected by IL-10 (Figdor, et al., *J. Immunol. Methods* 68:68 (1984)). Therefore, whether the inhibitory effects of IL-10 in MLR were observed only when monocytes were present was investigated. For this purpose highly enriched T cells obtained by negative selection were used as responder cells. Purified monocyte populations enriched either by centrifugal elutriation or by direct sorting of CD14⁺ cell, from PBMC, purified B lymphocytes, and EBV-LCL were used as stimulator cells.

FIGS. 4A–4D show the effects of IL-10 on the proliferative responses of purified T cells stimulated with various allogeneic cells. Purified T cells (1×10⁵/well) were cultured for 5 days with allogeneic irradiated elutriated monocytes (2×10⁴/well) (4A), positively sorted CD14⁺ monocytes (2×10⁴/well) (4B), purified B cells (3.3×10⁴/well) (4C), EVC-LCL (1×10⁴/well) (4D) in the presence of increasing concentrations of IL-10.

As can be seen in FIGS. 4A–4D, IL-10 strongly inhibited the proliferative responses induced by allogeneic monocytes independently of whether the monocytes were obtained by centrifugal elutriation (FIG. 4A) or positively sorted by the FACS (FIG. 4B), whereas the proliferative responses towards allogeneic EBV-LCL remained unaffected (FIG. 4D). As observed with specific proliferative responses to soluble antigens, these results indicate that allospecific proliferation is blocked when allogeneic monocytes, but not when allogeneic EBV-LCL are used as stimulator cells. Interestingly, the proliferative responses induced by freshly isolated highly purified allogeneic B cells were also inhibited by IL-10 (FIG. 4C), indicating that the suppressive effect of IL-10 is also present when B cells are used as stimulators, despite the fact that IL-10 has no measurable effect on class I or class II MHC expression on these cells.

Kinetic experiments revealed that the effect of IL-10 on MLR-induced proliferation decreased gradually with time. These results are shown in FIG. 5, wherein PBMC (1×10⁵/well) and allogeneic irradiated PBMC (1×10⁵/well) were cultured for 5 days, and increasing concentrations of IL-10 were added at times indicated. IL-10 was most effective when added at the beginning of the primary cultures: if added at days 2 or 3 after the onset of the cultures, the effects were only marginal and no clear dose response effects were observed. These results indicate that IL-10 acts on the early stages of activation of T cells in MLR.

Example 5
IL-10 Effects on Cytokine Production in MLC

IL-10 has been shown to reduce IFN-γ and GM-CSF production by PBMC activated by anti-CD3 or PHA (Bacchetta, et al., *J. Immunol.* 144:902 (1989); Bevan, 1984, supra). In addition, IL-10 inhibits the production of cytokines by monocytes (Bejarano, et al., *Int. J. Cancer.* 35:327 (1985); Fiorentino, et al., supra.). To determine the effect of IL-10 on cytokine production in one-way MLR, allogeneic PBMC were used as responder and as stimulator cells. The cultures were carried out in the absence or in the presence of IL-10 or anti-IL-10 mAb, and supernatants were collected at day 5 and assayed for their cytokine content. In Table I it is shown that IFN-γ, IL-6, GM-CSF, and TNF-α were produced in MLR, and that IL-10 inhibited the production of these cytokines to various extents.

TABLE I

EFFECT OF EXOGENOUS AND ENDOGENOUS IL-10 ON CYTOKINE PRODUCTION BY ALLOANTIGEN-STIMULATED LYMPHOCYTES

| Condition | | | Cytokine | | | | |
|---|---|---|---|---|---|---|---|
| IL-10 (U/ml) | αIL-10 (μg/ml) | IL-6 (ng/ml) | IL-10 (ng/ml) | GM-CSF (pg/ml) | TNF-α (pg/ml) | IFN-γ (ng/ml) | |
| A | 0 | | 22.2 | 572 | 109 | 79 | <1 |
| | 1 | | 20.5 | | 41 | 61 | <1 |
| | 10 | | 13.0 | | 11 | 38 | <1 |
| | 100 | | 12.1 | | 16 | 47 | <1 |
| | | .05 | 22.9 | | 144 | 144 | <1 |
| | | .5 | 25.8 | | 165 | 111 | <1 |
| | | 5 | 24.9 | | 172 | 51 | <1 |
| A + B | 0 | | 35.4 | 1473 | 1744 | 141 | 29.5 |
| | 1 | | 35.3 | | 928 | 151 | 20.8 |
| | 10 | | 23.9 | | 784 | 82 | 18.1 |
| | 100 | | 24.7 | | 612 | 66 | 11.4 |
| | | .05 | 36.9 | | 2372 | 137 | 33.1 |
| | | .5 | 39.1 | | 2355 | 137 | 45.3 |
| | | 5 | 39.1 | | 3487 | 250 | 43.8 |

Human PBMC (A) were cultured for 5 days alone or with allogeneic irradiated PBMC (B) in the absence and in the presence of IL-10 or the anti-IL-10 mAb, 19F1. Production of cytokines was determined in the supernatants by cytokine-specific ELISAs.

No significant IL-4 production was detected and the levels of IL-5 were below 100 pg/ml. The production of IL-10 ranged from 1000 to 3000 pg/ml in different experiments. The strongest inhibitory effects of exogenous IL-10 were observed on the production of IFN-γ, whereas the weakest inhibitory effects were observed on IL-6 production.

Figure 6:
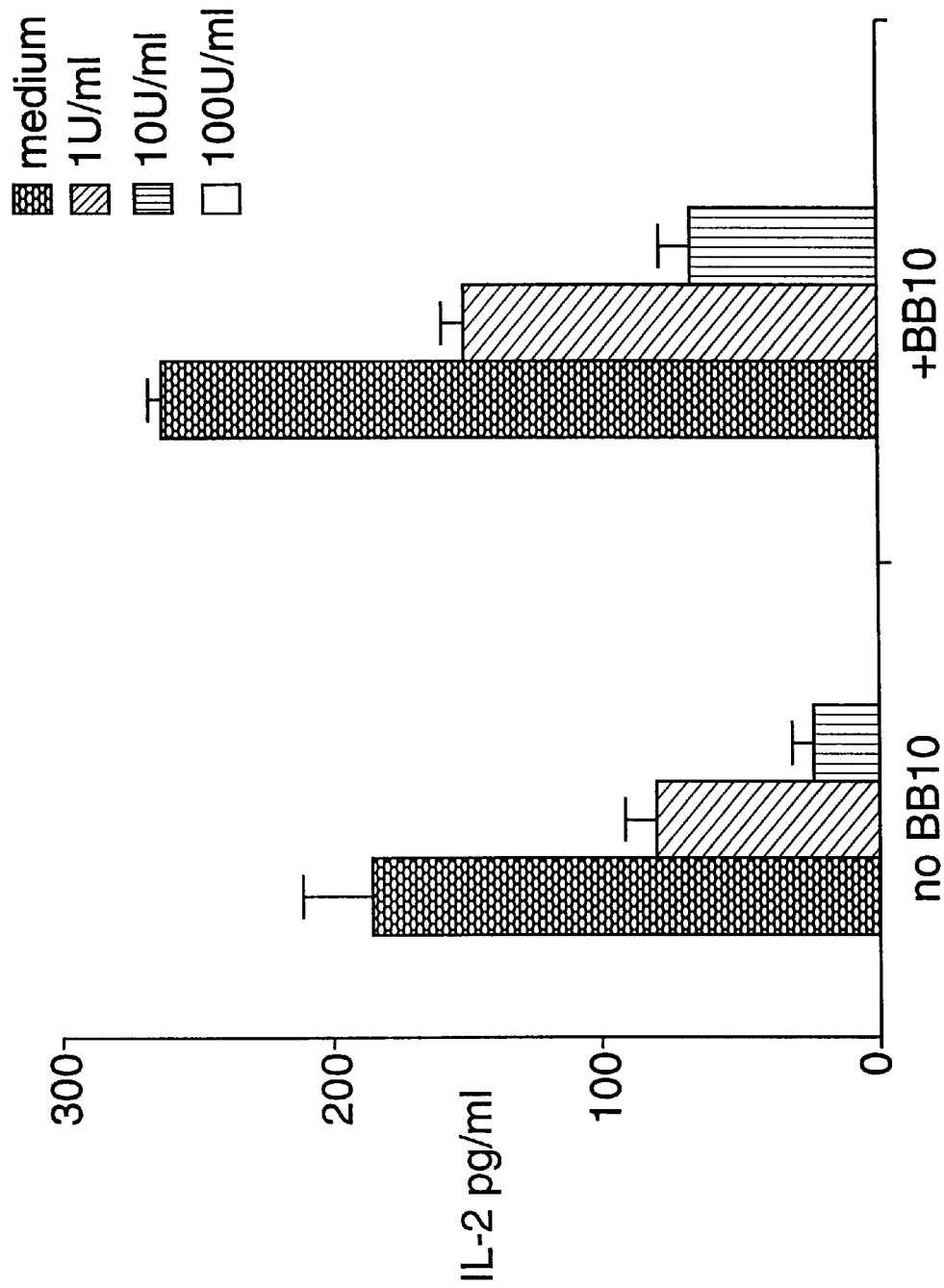
FIG. 6 shows a histogram of the effect of IL-10 on IL-2 products in MLR in the presence or absence of the anti-IL-2 receptor α chain mAb BB10.

Increased IFN-γ, GM-CSF, and TNF-α levels were observed in supernatants of MLR carried out in the presence of anti-IL-10 mAb, as, shown in Table I. These enhancing effects of anti-IL-10 mAb on cytokine production were dose-dependent. Taken together these results indicate that both endogenous and exogenous IL-10 reduce the production of the cytokines tested. To evaluate the effect of IL-10 on IL-2 production in MLR, and to minimize IL-2 consumption by activated T cells, the cultures were carried out in the presence or in the absence of IL-10 and the anti-IL-2 receptor mAb BB10. In these experiments IL-10 prevented IL-2 production in a dose-dependent manner (FIG. 6). No measurable levels of IL-2 could be detected when IL-10 was added at 100 U/ml. In FIG. 6, PBMC (1×10⁵/well) and allogeneic irradiated PBMC (1×10⁵/well) were cultured with increasing concentrations of IL-10 and in the presence or in the absence of 10 pg/ml of the anti-IL-2 R antibody, BB10. Three days later the supernatants were harvested and assayed for the IL-2 content by cytokine specific ELISA.

Figures 7A, 7B:
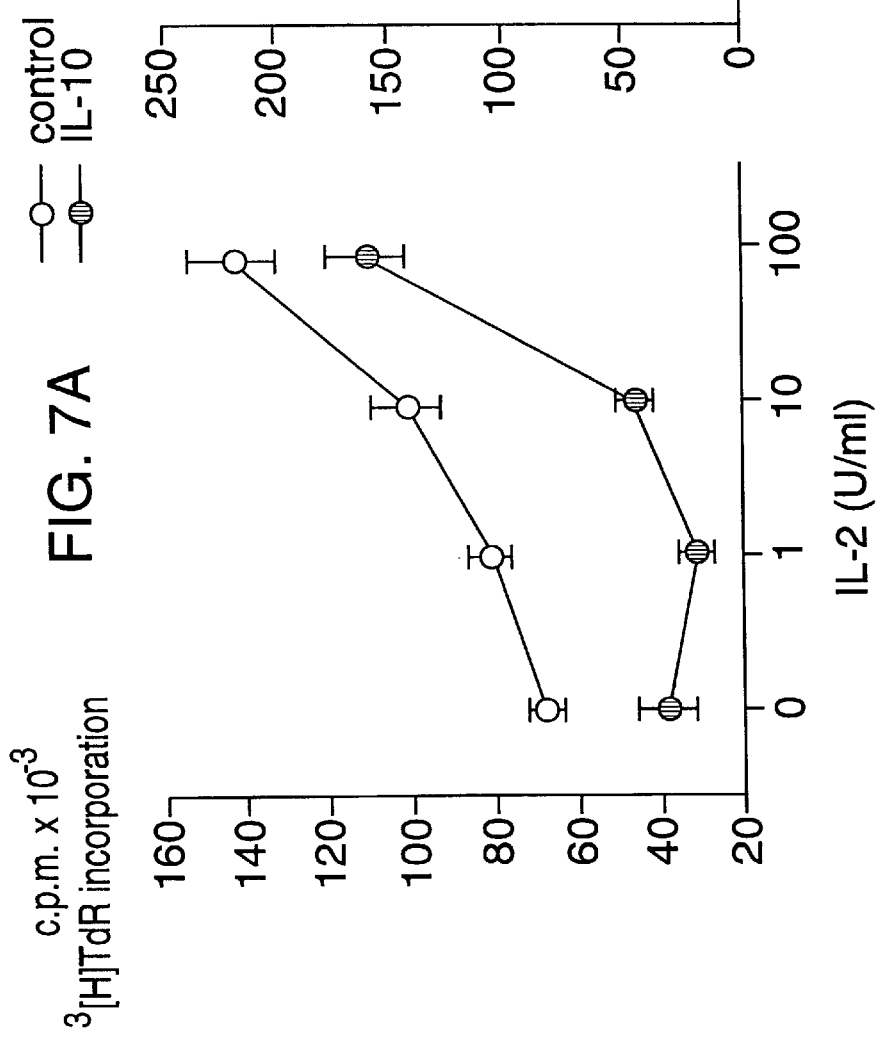
FIGS. 7A through 7B show the effect of exogenous IL-2 on the reduced alloantigen-induced proliferative response of stimulated T cells.

To investigate whether the inhibitory effects of IL-10 were observed in the presence of exogenous IL-2, MLR were carried out with various concentrations of IL-2. In FIGS. 7A–7B, the effects of exogenous IL-2 on the reduced alloantigen-induced proliferative response of T cells induced by IL-10 is shown. Purified T cells ($10^5$/well) stimulated with allogeneic irradiated PBMC ($10^5$/well) (7A), or purified B cells ($3.3 \times 10^4$/well) (7B), were cultured with increasing amounts of IL-2 in the absence (open symbols) or in the presence (closed symbols) of 100 U/ml of IL-10. These show that addition of increasing amounts of IL-2 to MLR, in which purified T cells were used as responders and PBMC or purified B cells as stimulators, enhanced the proliferation both in the absence or in the presence of IL-10. However, the inhibitory effects of IL-10 were still present when IL-2 was added at concentrations up to 100 U/ml [10 U/ml are sufficient to saturate high affinity IL-2 receptor (IL-2R)]. Similarly, addition of 400 U/ml of IL-4, which has T cell growth factor activity (Panina-Bordignon, et al., Science 252:1548 (1991)), failed to restore the reduced proliferative responses induced by IL-10. Taken together, these results demonstrate that the lack of IL-2 is not the limiting factor responsible for the reduced proliferative responses observed when MLR are carried out in the presence of IL-10.

Example 6
IL-10 Effects on Propagation of Activated T Cells in MLC

In order to determine whether the reduced proliferative responses in MLR in the presence of IL-10 differentially affected $CD4^+$ or $CD8^+$ T cell subsets, the proportions of $CD3^+CD4^+$ and $CD3^+CD8^+$ cells were determined and data are as indicated in Table 2.

$CD8^+$ T cells remained the same, indicating that IL-10 has no preferential effect on each of these T cell subsets.

In contrast, the proportion of activated T cells expressing CD25 and HLA-DR antigens was consistently reduced in IL-10 containing cultures. The strongest reduction was usually observed in MLR where purified $CD3^+$ T cells were stimulated with purified B cells or monocytes.

Thus, IL-10 reduces in a dose-dependent fashion the proliferation of alloresponsive T cells in classical one-way primary MLR in which allogeneic PBMC of two different donors were used as responder and irradiated stimulator cells, respectively. These inhibitory effects were completely neutralized by an anti-IL-10 mAb, demonstrating the specificity of the inhibition. The proliferative responses were considerably enhanced in the presence of the anti-IL-10 mAb, indicating that endogenous IL-10 production is responsible for suppression of proliferative responses in MLR.

IL-10 also reduced the proliferative responses in MLR where highly purified T cells were used as responders and purified monocytes as stimulators. Interestingly, IL-10 was ineffective when purified T cells were stimulated by irradiated allogeneic EBV-LCL. IL-10 strongly blocked the specific proliferative responses of T cells or T cell clones towards soluble antigens or antigenic peptides when monocytes, but not when EBV-LCL, were used as APC. This reduced antigen presenting capacity was found to be associated with the downregulatory effect of IL-10 on class II MHC expression on monocytes. In contrast, IL-10 did not affect class II MHC expression on EBV-LCL (Figdor, et al., J. Immunol. Methods 68:68 (1984)). From these data it was concluded that the reduced antigen specific proliferative T cell responses reflected prevention of activation of the responder cells, rather than a direct suppressive effect on T cell proliferation. This conclusion was further supported by the reduced $Ca^{2+}$ fluxes in the responder T cell clones

TABLE 2

Effect of IL-10 on Alloantigen-Stimulated T cells

| | T cell count | | % positive cells | | | | | | | |
|---|---|---|---|---|---|---|---|---|---|---|
| | $10^{-6}$/ml | | $CD3^+CD4^+$ | | $CD3^+CD8^+$ | | $CD3^+CD25^+$ | | $CD3^+DR^+$ | |
| | — | IL-10 | — | IL-10 | — | IL-10 | — | IL-10 | — | IL-10 |
| experiment 1 | | | | | | | | | | |
| T + PBMC | 1.3 | .76 | 69 | 73 | 21 | 24 | 4 | 2 | 3 | 2 |
| T + B cells | 1.2 | .72 | 55 | 62 | 28 | 28 | 24 | 18 | 19 | 8 |
| experiment 2 | | | | | | | | | | |
| T + PBMC | 1.4 | 1.0 | $ND^b$ | ND | ND | ND | 39 | 27 | 36 | 32 |
| T + B cells | .90 | .68 | ND | ND | ND | ND | 20 | 8 | 18 | 4 |
| T + monocytes[a] | 1.2 | .40 | ND | ND | ND | ND | 52 | 24 | 43 | 25 |
| experiment 3 | | | | | | | | | | |
| T + PBMC | 1.02 | .37 | 77 | 78 | 18 | 16 | 16 | 13 | 15 | 9 |
| T + monocytes[c] | .50 | .17 | 76 | 79 | 19 | 16 | 7 | 4 | 8 | 5 |

Purified T cells were cultured with allogeneic irradiated PBMC, purified B cells, or monocytes in the absence or presence of IL-10 (100 U/ml). Six days later the recovered T cells were counted and phenotype-determined by indirect immunofluorescence.
[a]Negatively sorted monocytes
[b]ND = not done
[c]positively sorted monocytes ($CD14^+$)

In Table 2, it is shown that the total T cell number decreased by 30 to 60% when the T cells were stimulated with allogeneic PBMC, purified monocytes, or B cells in the presence of IL-10. However, the proportion of $CD4^+$ and activated in the presence of IL-10 (Figdor, et al, J. Immunol. Methods 68:68 (1984)).

Interestingly, MLR-induced proliferation was not only inhibited by IL-10 when monocytes, but also when purified B cells were used as stimulators. Several studies have shown that T cell recognition of MHC alloantigens is mechanistically similar to recognition of viral, bacterial or other foreign protein antigens (Fiorentino, et al., J. Immunol. 146:3444 (1991); Fiorentino, et al., J. Immunol. 147:3815 (1991); Freedman, et al., J. Immunol. 139:3260 (1987); Go, et al., J. Exp. Med. 172:1625 (1990)). Recently, it has been shown that a significant proportion of MHC class II alloreactive T cell clones recognize processed determinants from human serum proteins in association with allogeneic class II molecules (Fiorentino, et al., *J. Immunol.* 147:3815 (1991)). In contrast to the situation where new MHC-peptide complexes have to be formed to activate antigen-specific T cell clones (Rotzchke, et al., *J. Exp. Med.* 174:1059 (1991)), there is no evidence to indicate that new allo-MHC-peptide complexes must be formed on monocytes and B cells to stimulate T cells in a MLR. It is unlikely that the inhibitory effects of IL-10 on MLR-induced T cell proliferation can be solely attributed to a downregulation of MHC class II expression on the monocytes.

It has been demonstrated that, in addition to crosslinking of the TCR/CD3 complex by specific alloantigen, LFA-1—ICAM-1 interactions are required for cytokine production by allospecific T cells (Santos-Aguado, et al., Proc. Natl. Acad. Sci. USA 86:8936 (1989)). Furthermore, CD28—B7/BB1 interactions have been shown to be necessary for induction of alloantigen-specific activation of resting T cells, resulting in cytokine production, proliferation, and cytotoxic activity (Spits, et al., J. Immunol. 139:1143 (1987); Thompson-Snipes, et al., J. Exp. Med. 173:507 (1991); Vieira, et al., Proc. Natl. Acad. Sci. USA 88:1172 (1991)). B7 is weakly expressed on resting B cells and monocytes, but is elevated following activation of these cells. Hokochi, et al. J. Immunol. 128:823 (1982); Yssel, et al., Eur. J. Immunol. 16:1187 (1986)). However, it could be ruled out that the reduced proliferative and cytotoxic alloresponses were due to downregulatory effects of IL-10 on the expression of either TCR/CD3 or these accessory molecules.

The reduced proliferative responses towards alloantigens also reflects prevention of activation of the responder T cells. IL-10 had to be present from the onset of the cultures to exert its maximal inhibitory effects. In addition, the proportion of activated T cells, as judged by the expression of CD25 and HLA-DR antigens, was considerably lower in the IL-10 containing cultures as compared to the control MLR. Although the total number of $CD3^+$ T cells generated in MLR carried out in the presence of IL-10 was reduced, IL-10 did not preferentially affect the responses of $CD4^+$ or $CD8^+$ T cells, since the proportions of these T cells subsets were comparable to those in control MLR carried out in the absence of IL-10. The reduced expression of CD25 indicates that the inhibitory effect on T cell proliferation in a MLR is not a mere consequence of the cytokine inhibitory activity of IL-10. This is supported by the finding that IL-10 also reduces the proliferative responses when exogenous IL-2 is added at concentrations that are sufficient to saturate high affinity IL-2 receptors. Collectively, these data suggest that IL-10 reduces the stimulatory capacity of PBMC, monocytes, and normal B cells in MLR.

The levels of cytokines produced in MLR in which total allogeneic PBMC were used as responder and stimulator were also significantly reduced in the presence of exogenous IL-10. The amounts of IL-2, IFN-$\gamma$, TNF-$\alpha$, and GM-CSF were approximately two to three fold lower than those of control MLR carried out in the absence of IL-10. IL-6 production was much less affected, which may be due to the fact that monocytes present in these cultures already produced considerable amounts of this cytokine very early after activation, before the suppressor activity IL-10 becomes effective (Bejarano, et al. Int. J. Cancer 35:327 (1985)).

Example 7

IL-10 and Tolerance in SCID Patients

The T cell repertoire and mechanism of tolerance in two patients with severe combined immunodeficiency (SCID) transplanted with HLA mismatched fetal liver stem cells was investigated. Two very young SCID children were transplanted 17 and 5 years ago with fetal liver stem cells from fully HLA disparate donors. Patient SP received 2 fetal liver stem cell transplantations and in both cases syngeneic fetal thymus was simultaneously injected. Although standard HLA typing showed engraftment of cells only from the second donor, a more precise cytofluorometric analysis, using monoclonal antibodies specific for polymorphic HLA determinants, indicated that 10–20% of the T lymphocytes were actually from the first donor. The second patient, RV, received 7 fetal liver stem cell transplantations, but only one donor cell population could be identified in the peripheral blood (Table 3).

TABLE 3

| | HLA TYPING | | | | |
|---|---|---|---|---|---|
| | A | C | B | DR | DQ |
| SP | | | | | |
| recipient | 3–33 | 6 | 14–47 | 4–5 | 3 |
| 1st donor | 2–11 | 4 | 27–62 | 1–8 | 1 |
| 2nd donor | 1–2 | 0 | 8–18 | 3–9 | 3 |
| RV | | | | | |
| recipient | 2–31 | 4–7 | –62 | 8–10 | 4–5 |
| donor | 2–30 | 4 | 8–35 | 11–13 | 6–7 |

In such patients, sustained engraftment of donor T cells was observed after transplantation, whereas B cells and monocytes were of host origin (Table 4).

TABLE 4

| CHIMERISM | |
|---|---|
| $\alpha\beta TCR^+$ T cells | Donor Origin |
| $\gamma\delta TCR^+$ T cells | |
| Monocytes | Host Origin |
| B cells | Host Origin -> Patient SP |
| NK cells | Donor Origin -> Patient RV |

Despite this state of split chimerism within cells of the immune system, complete reconstitution was achieved and normal in vivo and in vitro antibody responses to recall antigens were observed. This is due to the ability of donor T cells to cooperate with the APC of the host, across the allogeneic barrier. In particular, these studies demonstrated that tetanus toxoid (TT) specific T cell clones of donor origin, isolated from the peripheral blood of patient SP, can recognize the antigen (Ag) processed and presented by host B cells, EBV transformed B cell lines, and NK cell clones. In contrast, none of the Ag specific T cell clones tested recognized TT presented by the class II HLA antigen expressed by the donor cells, Roncarolo, et al., J. Exp. Med. 167:1523 (1989).

The chimerism in the NK population differed in the two patients, as shown in Table 4. In one case, fresh NK cells and NK cell clones showed the HLA phenotype of the host; in the other case, they were of donor origin. These NK cells expressed the CD16 and CD56 antigens and displayed normal cytotoxic activity against a variety of NK sensitive targets.

These findings suggest that the presence of host or donor functional NK cells do not prevent stable engraftment of donor T cells after fetal stem cell transplantation. Despite the coexistence of lymphoid cells with major and/or minor histocompatibility antigen differences, complete tolerance was achieved in vivo in these two patients and no signs of acute or chronic graft versus host disease were observed. Furthermore, in vitro studies showed that specific nonresponsiveness by the donor T cells towards the HLA antigens expressed by the host was present in a primary mixed leucocyte culture (MLC), whereas the proliferative responses against allogeneic cells were normal. At the clonal level, however, the findings have differed. Host-reactive proliferative and cytotoxic T cell clones of donor origin recognizing either HLA class I or HLA class II antigens of the host have been derived from the peripheral blood of both patients. In contrast to what has been reported in SCID patients transplanted with marrow from HLA-haploidentical parental donors (Keeren, et al. Hu. Immunol. 29:42, (1990)), no donor-reactive T cell clones could be isolated in these two patients. Furthermore, in patient RV, no T cell clones specific for the HLA class I locus A antigens of the host that were shared by the donor could be identified. Frequency analysis using a modified limiting dilution assay confirmed the lack of donor reactivity and demonstrated that the frequency of $CD8^+$ host-reactive T cells was in the same range as the frequency of T cells reacting against third party HLA antigens. Thus, host-reactive cells are not clonally deleted from the donor T cell repertoire. Presumably, such host-reactive T cells are under regulation since clinical manifestations of graft versus host disease were not evident in these patients. One possibility is that the host-reactive cells are anergic in vivo and that in vitro stimulation in the presence of IL-2 can break this anergy. It is known that host-reactive T cells display a peculiar pattern of lymphokine production after polyclonal and antigen-specific stimulation. None of the $CD4^+$ as well as the $CD8^+$ T cell clones are able to secrete IL-4 whereas they synthesize normal levels of IL-2, IL-5, and GM-CSF after polyclonal activation. IFN-$\gamma$ production by these clones is usually very high. In addition, IL-10 production by $CD4^+$ host-reactive T-cell clones of patent RV is extremely high after antigen-specific stimulation and seems inversely correlated to the low IL-2 synthesis. Furthermore, addition of exogenous IL-10 can significantly suppress the proliferative responses of $CD4^+$ host-reactive T cell clones in vitro. Therefore, IL-10 production by host-reactive T cells may play an important role in down-regulating their responses in vivo.

The patients are now (1992) age 17 and 5 years old, healthy, and show normal immunoresponses to recall antigens. Their T cells are of donor origin, whereas monocytes and B cells remained of the host. The NK cells have different sources since in one patient they derive from the donor and in the other one from the host. Despite the HLA mismatch between donor and host cells, no acute or chronic graft versus host disease was observed. In vitro experiments with PBMC showed specific nonresponsiveness for the HLA antigens expressed by the host cells. However, an extensive clonal analysis showed that $CD4^+$ and $CD8^+$ host-reactive T cell clones recognizing class II and class I HLA molecules of the host, respectively, were present in the peripheral blood of both patients. Limiting dilution experiments indicated that the frequency of $CD8^+$ host-reactive cells was in the same range as that observed for alloreactive T cells. In contrast, no donor reactive $CD8^+$ T cells could be isolated. Host-reactive $CD4^+$ and $CD8^+$ T cell clones were normal in their capacity to produce IL-2, IFN-$\gamma$, GM-CSF, and IL-5, but they failed to synthesize IL-4. In addition, $CD4^+$ T cell clones from patient RV secreted very high levels of IL-10. Exogenous IL-10 was able to inhibit the proliferative responses of the $CD4^+$ host-reactive T cell clones. The host-reactive cells are not deleted from the donor T cell repertoire following allogeneic fetal liver stem cell transplantation. Therefore, in vivo tolerance between the host and the donor is maintained by a peripheral autoregulatory mechanism in which cytokines may play a role.

Example 8

Induction of Long Term Antigen-Specific Anergy in Human $CD4^+$ T Cells

Human $CD4^+$ T cells, activated by allogeneic monocytes in a primary MLR in the presence of exogenous IL-10, specifically failed to proliferate after restimulation with the same alloantigens. A comparable state of T-cell unresponsiveness could be induced by activation of $CD4^+$ T cells by crosslinked anti-CD3 mAbs in the presence of exogenous IL-10. The anergic T cells failed, upon restimulation with alloantigen or anti-CD3 mAb, to produce IL-2, IL-5, IL-10, IFN-$\gamma$, TNF-$\alpha$, and GM-CSF. However, restimulation of anergized T cells with anti-CD3 mAbs induced normal $Ca^{2+}$ fluxes and resulted in increased CD3, CD28, and class II MHC expression indicating that calcineurin mediated signaling occurs in these anergic cells. The IL-10-induced anergic state was long-lasting. T-cell anergy could not be reversed following restimulation of the cells with anti-CD3 mAbs and anti-CD28 mAbs, although CD3 and CD28 expression was normal. However, the expression of the IL-2R $\alpha$ chain was not upregulated, which may account for the failure of exogenous IL-2 to reverse the anergic state. Interestingly, anergic T cells and their non anergic counterparts showed comparable levels of proliferation and cytokine production following activation with PMA and $Ca^{2+}$ ionophore indicating that a direct activation of a PKC dependent-pathway can overcome the tolerizing effect of IL-10. Taken together, these data demonstrate that IL-10 induces T-cell anergy and therefore may play an important role in the induction and maintenance of antigen-specific T-cell tolerance.

IL-10 has been shown to inhibit antigen-specific activation and proliferation of human peripheral blood T cells and T cell clones belonging to the Th0, Th1, or Th2 subsets. Yssel, et al., J. Immunol. 149:2378–2384 (1992); and de Waal Malefyt, et al., J. Exp. Med. 174:915–924 (1991). These inhibitory effects were indirect and mediated through inhibition of the function of antigen-presenting cells (APCs). Macatonia, et al., J. Immunol. 150:3755–3765 (1993); Caux, et al., Int. Immunol. 6:1177–1185. (1994); Pecanha et al., J. Immunol. 150:3215–3223. (1993); and Ding and Shevach, J. Immunol. 148:3133–3139 (1992). IL-10 regulates constitutive and IFN-$\gamma$ or IL-4 induced class II MHC expression on monocytes, dendritic cells, and Langerhans cells. de Waal Malefyt, et al., J. Exp. Med. 174:915–924 (1991); and Peguet-Navarro, et al., Eur J. Immunol. 24:884–891 (1994). In addition, IL-10 inhibits the expression of CD54 (ICAM-1, the ligand for LFA-1), and of CD80 and CD86 (ligands for CD28) which function as important costimulatory molecules for T cell activation. Ding, et al., J. Immunol. 15:1224–234 (1993); Willems, et al., Eur. J. Immunol. 24:1007–1009 (1994); Chang, et al., Eur. J. Immunol. 25:394–398 (1995). More recently, it has been shown that IL-10 also has a direct effect on $CD4^+$ T by suppressing IL-2 secretion. de Waal Malefyt, et al., J.

Immunol. 150:4754–4765 (1993); and Taga, et al., Blood 81:2964–2971 (1993).

Similar to its inhibitory effects on T cell proliferation in response to soluble antigens, IL-10 strongly reduced the proliferation of human alloreactive cells in mixed lymphocyte reactions (MLR) and the levels of cytokines produce in these MLR were significantly reduced in the presence of exogenous IL-10. Bejarano, et al., Int. Immunol. 4:1389–1397 (1992) and above. In addition, IL-10 suppressed the proliferative responses of CD4+ allogeneic T cell clones. In parallel with the reduced proliferation, reductions in the levels of IL-2, IL-5, GM-CSF, and IFN-γ production by these T cell clones were observed. Roncarolo, "Interleukin-10 and transplantation tolerance" in de Waal Malefyt and de Vries (eds.) Interleukin-10, Landes Company, Austin, Tex., p. 113–120 (1995).

Recently, it was reported that in SCID patients successfully transplanted with HLA-mismatched hematopoietic cells, CD4+ T cell clones specifically recognizing the host alloantigens produce very low levels of IL-2 after antigenic stimulation, but secrete high amounts of IL-10, which partially inhibits their proliferation in vitro. Bacchetta, et al., J. Exp. Med. 179:493–502 (1994). Furthermore,. PBMC from these SCID patients express considerably higher levels of IL-10 transcript compared with PBMC of normal controls, especially in the non-T cell subset. Bacchetta, et al., J. Exp. Med. 179:493–502 (1994). These results suggest that the high expression of IL-10 detected in SCID human chimeras may play a key role in the maintenance of in vivo tolerance, by inducing an anergic state in donor-derived T cells specific for the host alloantigens.

Optimal activation and expansion of alloreactive T cells requires, in addition to ligation of the TCR complex, costimulatory signals provided by one or more accessory molecules expressed on alloantigen-presenting cells. Engagement of the TCR by antigens without costimulation results in T cell anergy. De Silva, et al., J. Immunol. 147:3261–3267 (1991); Jenkins, et al., J. Immunol. 144:16–22 (1990); Schwartz, Science 248:1349–1356 (1990); and Sloan-Lancaster, et al., J. Exp. Med. 180:1195–1205 (1994). This state of unresponsiveness may also be induced in vitro, in long-term T cell clones by stimulation with agents that mimic T cell receptor occupancy, in the absence of CD28 signaling, and/or by inhibition of IL-2 secretion by T cells. De Silva, et al., J. Immunol. 147:3261–3267 (1991); Jenkins, et al., J. Immunol. 144:16–22 (1990); Schwartz, Science 248:1349–1356 (1990); and Sloan-Lancaster, et al., J. Exp. Med. 180:1195–1205 (1994). The observations that high levels of IL-10 are associated with transplantation tolerance, and that this cytokine has been shown to inhibit both the antigen presenting and accessory function of monocytes and the IL-2 production by T cells, suggest that IL-10 may be involved in the induction of anergy in CD4+ T cells.

In the present study, we demonstrate that IL-10 is able to induce a long-lasting antigen-specific unresponsiveness against allogeneic antigens that cannot be reversed by IL-2 or CD28 stimulation.

Cells

Peripheral blood mononuclear cells were prepared by centrifugation over Ficoll-hypaque. CD4+ T cells were purified by negative selection. Negative purification was performed using a cocktail of antibodies directed against non-CD4+ T cells: CD8, CD14, CD16, CD19, CD20, CD56, HLA-DR. Cells were incubated with saturating amounts of antibodies for 20 min at 4° C. After washing, Dynabeads (Dynal, Oslo, Norway) were added at a ratio of 10 beads/target cell and incubated for 1 hr at 4° C. Beads and contaminating cells were removed by magnetic field. The remaining cells were resuspended with the same number of beads and a second incubation period for 1 hr at 4° C. was performed. After removing contaminating cells, CD4+ T cells were analyzed by FACScan (Becton Dickinson, Mountain View, Calif.) and revealed to be more than 90–95% positive. Monocytes were purified using the same procedure with a cocktail containing antibodies for: CD2, CD3, CD8, CD16, CD19, CD20, CD56. These monocytes were >95% CD14+ by FACScan analysis. In some experiments, CD4+ T were purified by positive selection using magnetic beads directly coated with CD4 mAbs, according to the manufacturer instructions (Dynal, Oslo, Norway). With this procedure cells were more than 95% pure.

Reacents

Purified recombinant IL-10 was provided by Schering-Plough Research Institute (Kenilworth, N.J.). The anti-IL-2 receptor monoclonal antibody B-B10 (Herve, et al., Blood 75:1017–1023 (1990)), anti-CD3 mAb SPV-T3 (Spits, et al., Hybridoma 4:423–437 (1983)), and anti-CD28 (Becton Dickinson, Mountain View, USA) were previously described. Non-conjugated, PE- or FITC-conjugated antibodies for CD2, CD3, CD4, CD8, CD14, CD16, CD19, CD20, CD56, HLA-DR, an controls mAbs of the appropriate isotypes were purchased from Becton Dickinson (Mountain View, Calif.).

Proliferation Assays

In these proliferation assays, cells were cultured in Yssel's medium (Yssel, et al., J. Immunol. Methods 72:219–227 (1984)) supplemented with 10% FCS and 1% human serum. For MLR, purified CD4+ T cells ($5 \times 10^4$ cells/well) were stimulated with purified allogeneic: monocytes ($5 \times 10^4$ cells/well) or with irradiated PBMC ($10^5$ cells/well) in 200 μl. flat bottomed 96 well plates (Falcon, Becton Dickinson, Lincoln Park, N.J.). PBMC used as stimulators were irradiated at 4,000 rad.

For crosslinked anti-CD3 mAb activation, 500 ng/ml of anti-CD3 mAbs diluted in 0.1 M Tris buffer pH 9.5 was incubated for a week at 4° C. in flat bottom 96 or 24 well plates. These experimental conditions were found to be optimal in experiments in which different concentrations of antibodies and different incubation times were tested. After washing the plates three times, CD4+ T cells were added at $5 \times 10^4$ cells/well.

For activation with phorbol ester (PMA)+$Ca^{2+}$ ionophore (A23187 Sigma, USA), cells were cultured at $5 \times 10^4$ cells/well and activated for 3 days with PMA (1 ng/ml) and A23187 (500 ng/ml).

To measure the proliferation of T cells, cells were cultured for 72 h or 5 days for MLR experiments at 37° C. in 5% $CO_2$, and subsequently pulsed with [$^3$H]-TdR for 12 h, and harvested as described in Bacchetta, et al., J. Exp. Med. 179:493–502 (1994).

Induction of Anergy

To induce anergy, CD4+ T cells were cultured at $2.5 \times 10^5$ cells/ml in 24 well plates (Linbro, ICN Biomedical, Ohio) and activated either with purified allogeneic monocytes or with crosslinked anti-CD3 mAbs in the presence of IL-10 (100 U/ml). After different incubation periods (ranging from 3 to 10 days, see below) cells were collected, layered on a Ficoll-hypaque gradient to remove dead cells, washed twice, and restimulated with irradiated allogeneic PBMC or crosslinked anti-CD3 mAbs.

Immunofluorescence Analysis

For detection of cell surface antigens, $10^5$ cells were labeled with PE- or FITC-conjugated mAbs. Cells were incubated for 30 min with the appropriate antibody at 4° C. in PBS with 0.1% BSA and 0.02 mM NaN3. After 3 washes, the labeled cell samples were analyzed on a FACScan (Becton Dickinson).

Determination of Lymphokine Production

Cells were stimulated by cross-linked anti-CD3 mAbs, by PMA and $Ca^{2+}$ ionophore (A23187), or by allogeneic monocytes for 24 hr. The secretion of IL-2, IL-4, IL-5, IL-10, TNF-α, IFN-γ, and GM-CSF was measured by immunoenzymetric assays as described ion Bacchetta, et al., J. Exp. Med. 179:493–502 (1994) and Bacchetta, et al., Blood 85:1944–953 (1995). The sensitivity of the various ELISAs was: 20 pg/ml for IL-2; 40 pg/ml for IL-4 and IL-5; 50 pg/ml for GM-CSF and IL-10; and 100 pg/ml for IFN-γ and TNF-α.

Calcium Mobilization Studies

Mobilization of intracellular calcium in anergic cells loaded with indo-l/AM was assessed by using standard fluorometry. Cells were loaded with 2 μM indo-1/AM in complete growth medium at 20° C. for 45 min. Cells were then washed, resuspended in Na-HBSS (in mM: 2 $CaCl_2$, 145 NaCl, 5 KCl, 1 $MgCl_2$, 5 d-glucose, 20 HEPES; pH 7.3) containing 1% BSA, and maintained at 20° C. for up to two hours. Approximately $5 \times 10^5$ cells were then suspended in 2 ml Na-HBSS and maintained at 37° C. in a constantly stirred acrylic cuvette. Anti-CD3 mAbs (1 μg/ml) were added, followed by goat anti-mouse immunoglobulin to crosslink the anti-CD3 mnAbs on the cell surface. No $Ca^{2+}$ fluxes were detected in the absence of crosslinking, neither in anergic nor in control cells. Fluorescence measurements to determine $[Ca^{2+}]_i$ were made using a Photon Technologies Inc. spectrofluorimeter.

IL-10 Induces Alloantigen-specific T-cell Anergy

Figure 8A:
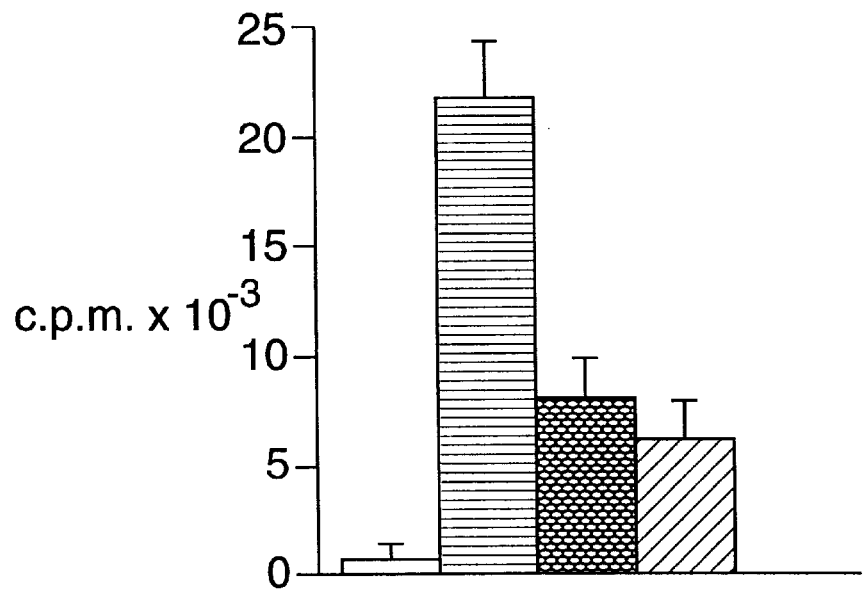
FIGS. 8A and 8B show that IL-10 induces an alloantigen-specific anergy in CD4+ T cells in a MLR.
Figure 8B:
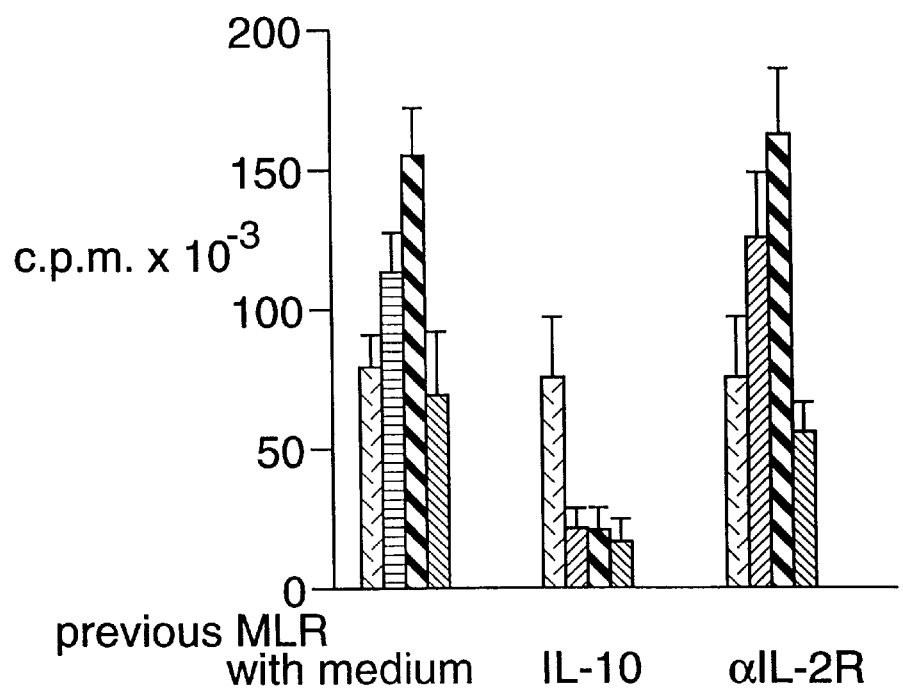

As shown previously (Bejarano, et al., Int. Immunol. 4:1389–1397 (1992) and above), IL-10 partially inhibits the proliferation of peripheral blood $CD4^+$ T cells in response to allogeneic monocytes in a primary MLR (FIG. 8A). This inhibition was comparable to that induced by anti-IL-2 α chain receptor mAbs (anti-CD25 mAbs). To determine whether prolonged incubation of the alloantigen-stimulated $CD4^+$ T cells in IL-10 might also downregulate their proliferative responses following restimulation, the cells were kept in culture in the presence or absence of IL-10 for 10 days (FIG. 8B). No significant cell death was observed in either culture condition and comparable cell numbers were harvested at termination of the assays. After this culture period, $CD4^+$ control T cells stimulated with alloantigens in the absence of IL-10 reached a resting state, and could be fully reactivated by the same allogeneic irradiated PBMC in a secondary MLR, or by third party allogeneic monocytes in a primary MLR (FIG. 8B). In contrast, $CD4^+$ T cells incubated in the presence of IL-10 failed to proliferate in a secondary MLR in response to the same allogeneic PBMC, but they retained their capacity to proliferate normally to third party alloantigens in a primary MLR. This unresponsive state could not be reversed by saturating concentrations of exogenous IL-2 (20 U/ml), or by anti-CD28 mAbs (10 μg/ml). Furthermore, this state of T-cell unresponsiveness is specific for IL-10 and is not due to inhibition of the primary MLR, since $CD4^+$ T cells incubated in the presence of anti-CD25 mAbs (10 μg/ml) for 10 days exhibited proliferative responses that were comparable to those of their untreated counterparts.

IL-10 Induces an Anergic State in $CD4^+$ T Cells Activated by Anti-CD3 mAbs

Figure 9A:
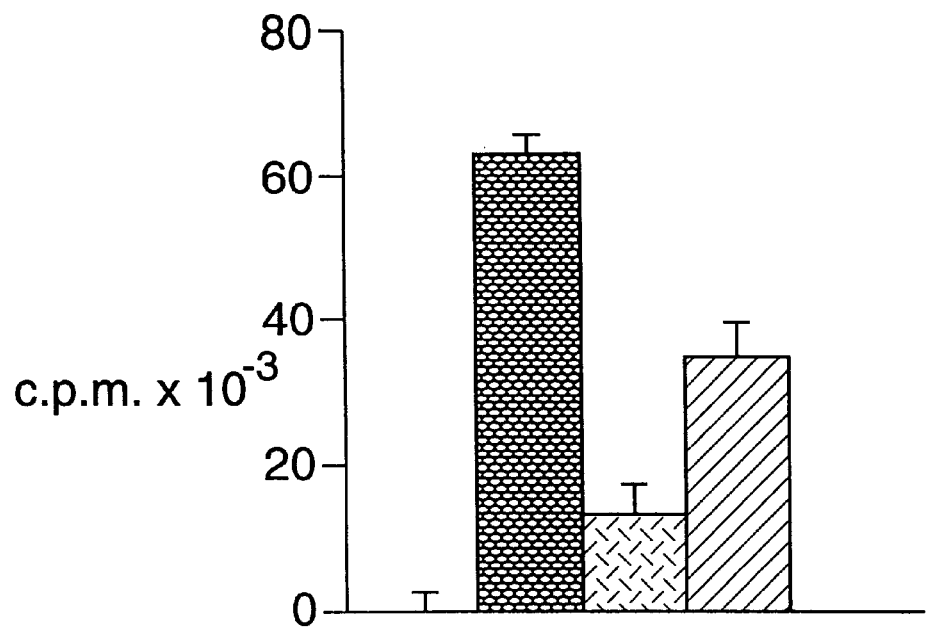
FIGS. 9A and 9B show IL-10 induces a polyclonal anergy in CD4+ T cells activated with CD3 mAb.
Figure 9B:
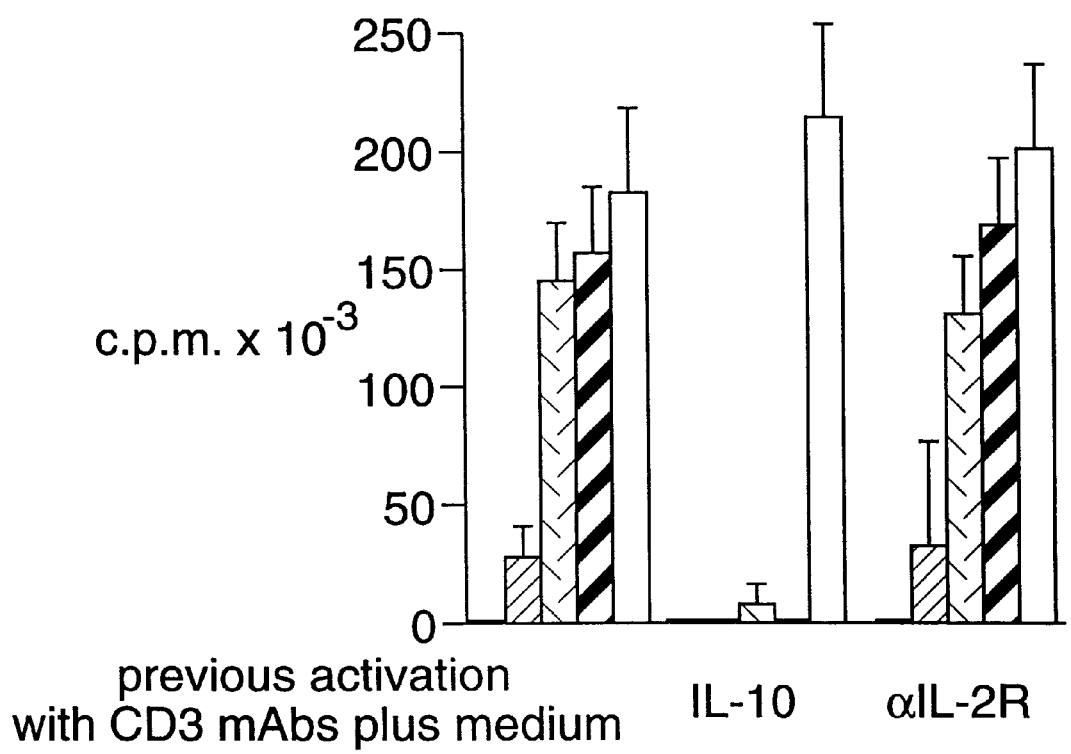
Figure 10:
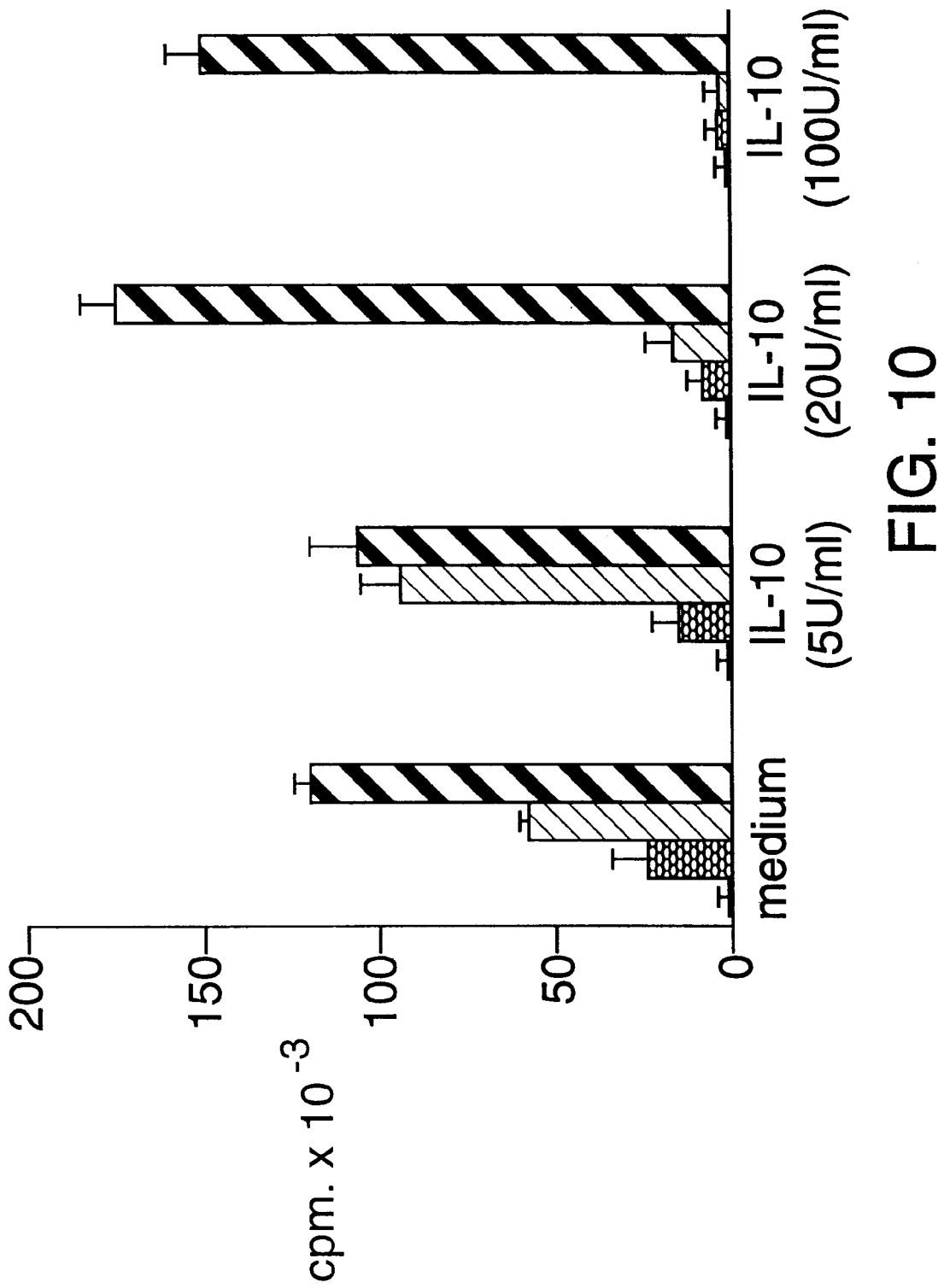
FIG. 10 shows dose dependent effect of IL-10 on anergy induction in CD4+ T cells. CD4+ T cells were activated for 10 days with crosslinked anti-CD3 mabs in the presence medium alone, IL-10 (5 U/ml), IL-10 (20 U/ml), or IL-10 (100 U/ml), as indicated under the 4 different panels. After 10 days, cells were collected, washed, and restimulated with medium alone (white bars), crosslinked anti-CD3 mAbs (black bars), crosslinked anti-CD3 mAbs plus IL-2 (20 U/ml) (hatched bars), or PMA plus $Ca^{2+}$ ionophore (black hatched bars).

Next was analyzed whether the IL-10-induced anergy reflected a direct effect of IL-10 on $CD4^+$ T cells. For this purpose, highly purified peripheral blood $CD4^+$ T cells were activated by crosslinked anti-CD3 mAbs, in the presence or absence of exogenous IL-10 for 10 days. A direct effect of IL-10 on $CD4^+$ T cells proliferation was observed (de Waal Malefyt, et al., J. Immunol. 150:4754–4765 (1993); and Taga, et al., Blood 81:2964–2971 (1993)) and this inhibitory effect was comparable to that induced by anti-CD25 mAbs (FIG. 9A). Activation of the $CD4^+$ T cells in the presence of IL-10 resulted in a profound state of T-cell unresponsiveness, which could not be reversed by exogenous IL-2, or anti-CD28 mAbs (FIG. 9B). However, anergic cells proliferated normally in response to stimulation by $Ca^{2+}$ ionophore and PMA. These results indicate that IL-10 induces an anergic state in $CD4^+$ T cells, but that these cells respond normally to signals circumventing TCR activation. This induction of anergy is IL-10-specific, similarly to IL-10 induced T-cell unresponsiveness to alloantigens, and not related to inhibition of cell proliferation, since $CD4^+$ T cells incubated in the presence of anti-CD25 mAbs for IC days proliferated normally in response to restimulation with crosslinked anti-CD3 mAbs. The induction of anergy by IL-10 was dose-dependent with maximal effects observed at 100 U/ml (FIG. 10). Cells that had been activated by anti-CD3 nAbs and cultured in the presence or absence of IL-10 for 10 days were in a resting state and no apoptoic cell death was observed in the control or IL-10 treated cell cultures. Thus, IL-10 induces a comparable state of T-cell anergy in alloantigen-specific and anti-CD3 stimulated $CD4^+$ T cells.

Kinetics of Anergy Induction by IL-10

Figure 11:
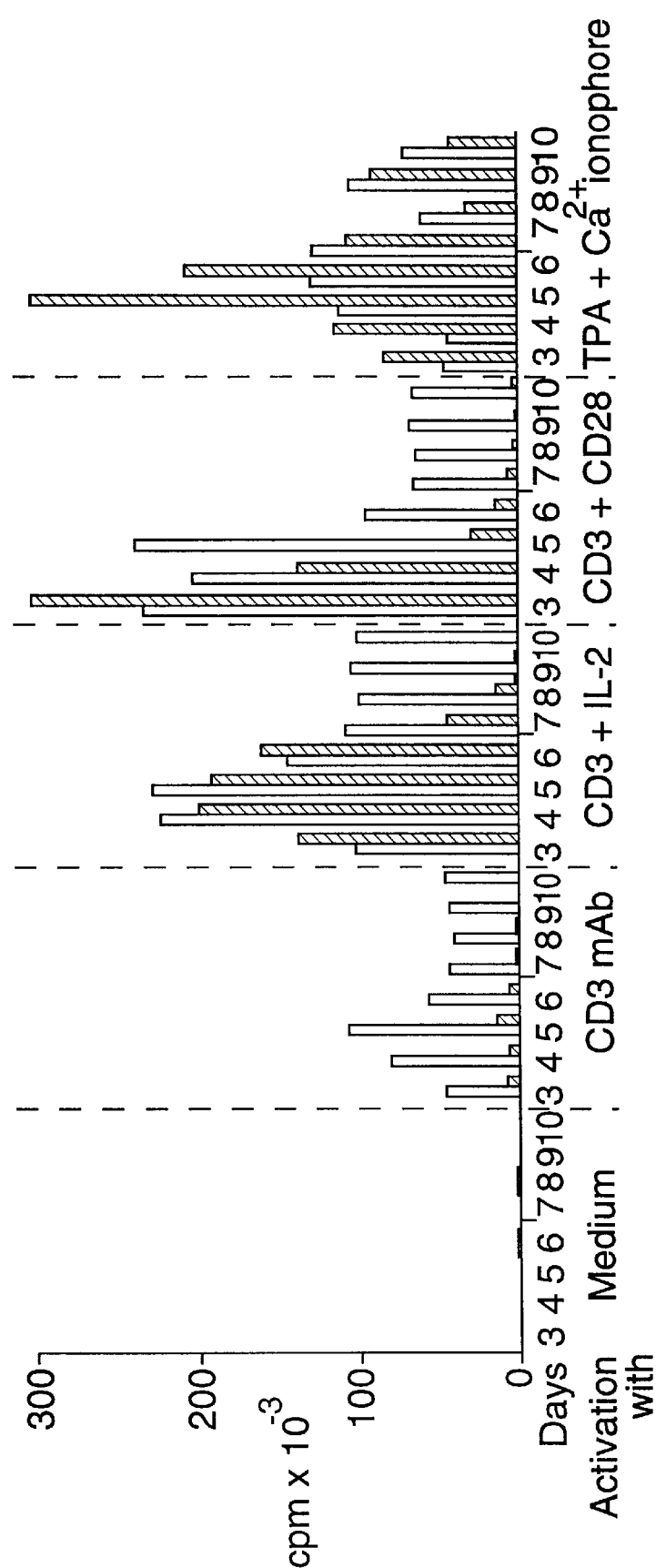
FIG. 11 shows kinetics of anergy induction by IL-10 in CD4+ T cells. CD4+ T cells were activated with crosslinked anti-CD3 mAbs in the absence (white bars) or presence (black bars) of IL-10 (100 U/ml). After different incubation periods, ranging from 3 to 10 days as indicated, cells were collected, washed, and restimulated as indicated under each panel with either medium alone, crosslinked anti-CD3 mAbs, crosslinked anti-CD3 mAbs plus IL-2 (20 U/ml), crosslinked anti-CD3 mAbs plus anti-CD28 mAbs (10 µg/ml), or PMA plues $Ca^{2+}$ ionophore.

To determine the kinetics of induction of T-cell anergy, $CD4^+$ T cells were activated with crosslinked anti-CD3 nAbs in the presence or absence of IL-10 and restimulated at different time points after initiation of the cultures (FIG. 11). $CD4^+$ T cells cultured in the presence of IL-10 for only 3 days already failed to proliferate in response to reactivation by crosslinked anti-CD3 mAbs. Interestingly, the anergic state of these cells could still be reversed by exogenous IL-2 (20 U/ml) or anti-CD28 (10 μg/ml). In contrast, incubation of the T cells with IL-10 for 9–10 days resulted in a complete state of anergy, which could not be reversed, either by the addition of IL-2 or anti-CD28 mabs. These results indicate that T cells activated through their TCR/CD3 complexes in the presence of IL-10 acquire different degrees of unresponsiveness, depending on the time periods they had been exposed to IL-10. This indicates that the period of IL-10 exposure will be very important in the effectiveness of suppression.

IL-10 Induced T-cell Anergy is Long-lasting

To determine the duration of the IL-10 induced anergic state in $CD4^+$ T cells after removal of IL-10, the cells were activated with crosslinked anti-CD3 mAbs in the presence or absence of IL-10 for 10 days. After this incubation period, the cells were washed and recultured for 24 days in the presence of low concentrations (2 U/ml) of exogenous IL-2, for optimal maintenance of the T cells over prolonged culture periods, but in the absence of IL-10. These T cells were collected every other day during the culture period, washed, and restimulated with anti-CD3 mAbs. T cells that previously had been incubated with IL-10 failed to proliferate even 24 days after removal of IL-10. In contrast, control $CD4^+$ T cells that had been activated by anti-CD3 mAbs in the absence of IL-10, and maintained in the absence of IL-10 for 24 days, proliferated normally in response to stimulation with anti-CD3 mAbs. In addition, the unresponsiveness observed after culturing the IL-10 treated cells for 24 days could not be reversed by IL-2 (20 U/ml) or anti- CD28 (10 jig/ml) mAbs. These results indicate that IL-10 induced T-cell anergy is profound and long lasting.

Aneraized T Cells Fail to Secrete Cytokines

T-cell anergy is generally defined as a failure of T cells to proliferate and to produce IL-2 in response to triggering of the TCR (see Schwartz, Science 248:1349–1356 (1990)). To determine whether T cells rendered unresponsive following activation with either allogeneic monocytes, or anti-CD3 mAbs, in the presence of IL-10 retained their ability to secrete cytokines, their cytokine production after restimulation with the same allogeneic monocytes or anti-CD3 mAbs, respectively, were analyzed. T cells which were rendered unresponsive following activation by either alloantigens plus IL-10, or anti-CD3 mAbs plus IL-10, failed to produce detectable amounts of IL-2, IL-4, IL-5, IL-10, TNF-α, IFN-γ, and GM-CSF at 24 hours (Table 5) or 48 hours after restimulation with the relevant allogeneic monocytes or anti-CD3 mAbs. In contrast, the untreated control cells produced levels of IL-2, IL-5, IL-10, IFN-γ, TNF-α, and GM-CSF that were comparable to those of a panel of $CD4^+$ T cells derived from different donors and stimulated in similar fashion. However, these cells did not secrete detectable levels of IL-4 (see Table 5).

CD28 expression and show that signaling through the TCR/CD3 complex, which is insufficient for T-cell proliferation, still occurs in these anergized T cells.

However, in contrast to the control cells, the anergic T cells failed to upregulate IL-2R α chain expression, indicating that inhibition of IL-2R α chain expression is a specific property of anergized T cells (FIGS. 14A and 14B). The defect in upregulation of CD25 expression was observed also in the presence of exogenous IL-2, and correlated with the failure of IL-2 to reverse T-cell anergy induced by 8–10 days of incubation with IL-10 (FIG. 11). In contrast, T cells rendered unresponsive following incubation with IL-10 for 3 days still expressed considerable levels of CD25 (FIG. 14A). Slight upregulation of CD25 was also observed following restimulation by anti-CD3 mAbs, but the levels of expression were still reduced as compared to untreated cells. However, addition of IL-2, which was able to reverse the anergic state, resulted in comparable levels of CD25 expression on control T cells and T cells incubated in the presence of IL-10 for 3 days (FIG. 14A).

Anti-CD3 mAbs Induce Normal $Ca^{2+}$ Fluxes in Anergic T Cells

The notion that signaling through the TCR/CD3 complex occurs in anergic T cells was confirmed by measuring the

TABLE 5

Cytokine profile, after restimulation, of IL-10 induced anergic T cells

| | | cpm | IL-2 pg/ml | IL-4 pg/ml | IL-5 pg/ml | IL-10 pg/ml | TNF-α ng/ml | IFN-γ ng/ml | GM-CSF pg/ml |
|---|---|---|---|---|---|---|---|---|---|
| CD3 | control cells | 42,369 | 875 ± 59 | <40 | 80 ± 23 | 1,067 ± 226 | 10.5 ± 0.9 | 5.5 ± 0.6 | 1,245 ± 687 |
| | anergic cells | 2,635 | <40 | <40 | <20 | <50 | <0.1 | <0.1 | <50 |
| TPA + $Ca^{2+}$ ionophore | control cells | 147,217 | 2,121 ± 317 | <40 | 841 ± 127 | 51 ± 27 | 21.6 ± 5.1 | 7.6 ± 3.1 | 2,721 ± 635 |
| | anergic cells | 169,321 | 1,921 ± 427 | <40 | 1,517 ± 415 | 117 ± 4.3 | 18.4 ± 3.6 | 8.4 ± 2.6 | 1,615 ± 317 |
| Monocytes | control cells | 32,236 | 617 ± 42 | <40 | 64 ± 15 | 897 ± 125 | 9.2 ± 0.5 | 2.3 ± 0.1 | 987 ± 98 |
| | anergic cells | 869 | <40 | <40 | <20 | <50 | <0.1 | <0.1 | <50 |

$CD4^+$ T cells were activated with either crosslinked anti-CD3 mAbs (10 μg/ml), allogeneic monocytes in the absence (control cells) or presence (anergic cells) of IL-10 (100 U/ml). Cells were kept in culture for 10 days, washed, and restimulated with crosslinked anti-CD3 mAbs; or TPA (1 pg/ml) and $Ca^{2+}$ ionophore (A23187: 500 ng/ml); or allogeneic PBMC, respectively. Supernatants were harvested after 24 hr and the levels of cytokines were analyzed by ELISA. To measure cell proliferation, cells were pulsed with [$^3$H] TdR for 12 h at the end of day 3 for cells activated with crosslinked anti-CD3 mAbs, or at the end of day 5 for cells activated with allogeneic monocytes.

FIG. 9 shows that activation with PMA and $Ca^{2+}$ ionophore. completely reversed IL-10 induced-unresponsiveness of anti-CD3 activated T cells. Table 5 shows that activation of anergic T cells by PMA and $Ca^{2+}$ ionophore for 24 hrs also resulted in levels of IL-2, IL-5, IL-10, IFN-γ, and TNF-α production that were comparable to those of their non-anergized counterpart.

Anergic T Cells Fail to Express CD25 After Activation

Phenotypic analysis of T cells rendered anergic following activation by anti-CD3 mAbs in the presence of IL-10 revealed no major differences as compared to their untreated counterparts, with the exception of a decrease in the IL-2R α chain (CD25) expression on the anergic T cells (see FIGS. 13 and 14A and 14B). No modulation of CD3 or CD28 expression was observed on anergic cells, and activation by crosslinked anti-CD3 mabs enhanced CD3, CD28, and class II MHC expression to the same extent as on control cells (FIG. 13). These data exclude the possibility that the T-cell unresponsiveness was related to defective TCR/CD3 or induction of $Ca^{2+}$ fluxes in these cells. After loading with Indo-1, cells were activated with anti-CD3 mAbs crosslinked by goat anti-mouse immunoglobulin, as indicated in FIG. 15. $Ca^{2+}$ fluxes induced in anergized T cells following activation with crosslinked anti-CD3 mAbs, were comparable to those in untreated control T cells (FIG. 15). The loading of the anergic and control cells with Indo-1 was equivalent, as shown by the comparable rise of $Ca^{2+}$ fluxes induced in the cells by addition of $Ca^{2+}$ ionophore (FIG. 15). These results indicate that IL-10 induced anergy affects downstream events involved in T-cell activation.

The present study shows that human peripheral blood $CD4^+$ T cells activated by allogeneic monocytes in the presence of IL-10 for 10 days were rendered unresponsive in an antigen-specific fashion. These unresponsive $CD4^+$ T cells failed to proliferate and to produce cytokines when restimulated by the same allogeneic monocytes. However, these T-cell populations proliferated normally in response to third party alloantigens. A comparable state of T-cell anergy was induced following activation of CD4+ T cells by anti-CD3 mAbs in the presence of IL-10. The IL-10 induced anergy was dose-dependent and lasted for more than 24 days after withdrawal of IL-10, which was the maximal time period analyzed. Furthermore the anergic state could not be reversed by exogenous IL-2, or the addition of anti-CD28 mAbs. In addition, T-cell anergy could not be induced by stimulation with allogeneic monocytes, or anti-CD3 mAbs in the presence of anti-IL-2 receptor mAbs. These results indicate that T-cell anergy is specifically induced by IL-10 and is not simply related to down regulation of IL-2 production by these cells.

IL-10 induced T-cell anergy differs clearly from T-cell unresponsiveness induced by incubation of mouse or human T cells with antigenic peptides in the absence of professional APC. See, e.g., Sloan-Lancaster, et al., J. Exp. Med. 180:1195–1205 (1994); Lamb, et al., J. Exp. Med. 157:1434–1447 (1983); and Fasler, et al., J. Immunol. 155:4199–4206 (1995). In this latter case, the expression of the TCR/CD3 complex was down-regulated and no mobilization of $[Ca^{2+}]_i$ was observed (Lamb, et al., J. Exp. Med. 157:1434–1447 (1983); and Fasler, et al., J. Immunol. 155:4199–4206 (1995)), unlike the findings with IL-10 induced anergy.

On the other hand, CD4+ T cells energized by IL-10 share many characteristics with anergic T cells described in murine models of anergy induced by lack of costimulatory signals. See De Silva, et al., J. Immunol. 147:3261–3267 (1991); Schwartz, Science 248:1349–1356 (1990); Suzuki, et al., Int. Immunol. 71:37–43 (1995); and Ramsdell and Fowlkes, Science 257:1130–1134 (1992). Both these forms of anergic cells failed to proliferate and to produce IL-2, but they had a normal expression of CD3 or CD28 surface molecules, and normal calcium fluxes after mobilization of the TCR/CD3 complex. See Schwartz, Science 248:1349–1356 (1990). However, T-cell anergy induced by IL-10 is much more profound than that described in these murine models, since the proliferative response of anergic T cells cannot be restored by addition of IL-2 or anti-CD28 mAbs. Furthermore, not only IL-2 production, but also the production, upon subsequent stimulation, of IFN-γ, IL-5, IL-10, TNF-α, and GM-CSF by these anergic cells was impaired. Therefore, induction of T-cell anergy by IL-10 is not simply due to inhibition of IL-2 production and prevention of productive CD28-CD80/CD86 interactions. IL-10 energized T cells are also different from T cells that undergo apoptosis or energized T cells able to secrete cytokines in the absence of proliferation. See Jenkins, Immunol. Today 132:69–73 (1992); and Groux, et al., Eur. J. Immunol. 23:1623–1629 (1993). In fact, no significant cell loss by apoptosis was observed in the anergic T cells cultured in IL-10 and the anergic T cells were viable as proven by the normal proliferation after stimulation with $Ca^{2+}$ ionophore and PMA.

Overall, these data indicate that signaling through the TCR/CD3 complex is selectively impaired in IL-10 anergized T cells. This is not due to a down regulation of the TCR or CD28 molecules, since the anergic T cells expressed levels of TCR/CD3 and CD28 that were comparable to those of untreated T cells. Furthermore, although stimulation of the anergic T cells through the TCR/CD3 complex did not result in cell proliferation and cytokine production, a clear increase in CD3, CD28, and class II MHC expression was observed following restimulation of the cells with anti-CD3 mAbs, indicating that some degree of TCR activation occurred in these anergic cells.

This notion was further supported by the observation that $Ca^{2+}$ fluxes in anergized T cells were normal following CD3 activation, demonstrating that calcineurin mediated signaling is not affected. Importantly, a complete reversal of anergy was observed after activation with PMA and $Ca^{2+}$ ionophore. These stimuli, which circumvent TCR activation, completely restored proliferation and cytokine secretion by anergic cells. These findings suggest that IL-10 interferes with proximal events in the TCR signaling pathway, probably at the level of Ras-MAP kinase activation, as is suggested by mouse models of anergy induction. See, e.g., Kang, et al., Science 257:1134–1138 (1992); Fields, et al., Science 271:1276–1278 (1996); and Li, et al., Science 271:1272–1275 (1996). Alternatively, although the signaling cascade downstream of p21ras seems to be intact, it cannot be excluded that IL-10 induces a negative regulator of this signaling pathway.

T cells rendered anergic by activation and incubation with IL-10 for 9–10 days failed, in contrast to their untreated counterparts, to upregulate the IL-2R α chain expression when restimulated with anti-CD3 mAbs. It is therefore tempting to speculate that this defect in upregulation of IL-2R α chain expression accounts for the failure of exogenous IL-2 to reverse anergy. This hypothesis is supported by the observation that T cells rendered anergic by activation and incubation with IL-10 for 3 days, and which still expressed CD25, could be rescued by exogenous IL-2. A comparable, but less profound, defect in IL-2 utilization has been reported for superantigen induced T-cell unresponsiveness in TCR-transgenic mice. See Bhandoola, et al., J. Immunol. 151:2355–2367 (1993). Taken together, these data suggest that anergy induction may be permanent if induced properly.

Among the mechanisms responsible for induction of tolerance to alloantigens a nondeletional mechanism that results in functional inactivation of the appropriate alloreactive T cells has been proposed. This functional inactivation can be achieved by blocking costimulatory signals provided by accessory molecules expressed on APC and T cells. See Lenschow and Bluestone, Curr. Opin. Immunol. 5:747–752 (1993); Linsley, et al., Science 257:792–795 (1992); Charlton, et al., Immunol. Cell. Biol. 692:89–93 (1991); and Nakao, et al., J. Immunol. 153:5819–5825 (1994). Prevention of the interaction between CD28 and either CD80 or CD86 appears to be critical for this induction of anergy, but blockade of other costimulatory molecules such as CD2, CD4, or CTLA-4 may also be involved. See Boussiotis, et al., J. Exp. Med. 180:1665–1673 (1994). However, the fact that the tolerance induced in these experimental models is long-lasting and potentially irreversible suggests underlying mechanisms which may be more complex than the mere lack of a second signal to the T helper cell upon recognition of alloantigens. It is possible that some form of active suppression is mediated by cytokines. These cytokines may contribute to the induction or maintenance of T-cell anergy not only by down-regulating costimulatory molecules, but also by inducing the expression of negative regulators, such as CTLA-4. See Tivol, et al., Immunity 3:541–547 (1995). In humans, SCID patients are one of the few examples in which in vivo tolerance is obtained after HLA-mismatched transplantation. This tolerance is due to a nondeletional mechanism that is responsible for the functional inactivation of T cells specifically recognizing the host alloantigens. See above, and Roncarolo, et al., J. Exp. Med. 167:1523–1534 (1988); and Bacchetta, et al., J. Clin. Invest. 91:1067–1078 (1993). These host-reactive T cells secrete high levels of IL-10 in vitro, and high IL-10 levels have been observed in vivo, suggesting that IL-10 may play a role in the induction and maintenance of tolerance. See Bacchetta, et al., J. Exp. Med. 179:493–502 (1994). Based on the present results it is tempting to conclude that the high levels of IL-10 observed in these patients render the host-reactive T cells anergic in vivo. High levels of IL-10 secretion prior to transplantation have been also shown to correlate with a successful outcome of the transplant (Holler, et al., Eur. J. Cancer. 31:39–45 (1995)), further supporting the hypothesis that IL-10 might play a role in the induction of tolerance.

Collectively, these data suggest that IL-10 has an important role in transplantation tolerance by inducing anergy to donor-specific and/or host-specific alloantigens. In addition, they suggest that IL-10 will have a potential clinical utility in preventing or reducing GVHD and allograft rejection.

FIG. 16 shows that the proliferative responses of purified CD4$^+$ T cells that had been rendered anergic following stimulation with crosslinked anti-CD3 mAbs (100 ng/ml) in the presence of IL-10 (100 U/ml) for 10 days, can be partially restored following restimulation with very high concentrations of crosslinked anti-CD3 mAbs.

Table 6 shows that the restimulation of CD4$^+$ T cells that have been anergized following stimulation by crosslinked anti-CD3 mAbs in the presence of IL-10 for 10 days with extremely high levels of anti-CD3 mAbs (700 mg/ml), results in low levels of proliferation and in et Th3 cytokine production profile, which is characterized by the production of high levels of IL-10, very low levels of IL-2 and no detectable levels of IL-4. In addition, IL-5, IFN-γ, GM-CSF, and TNF-α production can be detected. In contrast, the anergized CD4$^+$ T cells failed to proliferate and to produce cytokines when stimulated with crosslinked anti-CD3 mAbs at concentrations of 10 μg/ml.

obtained from anergized or non-anergized control T-cell populations.

TABLE 7

Cytokine profile of CD4$^+$ T cell clones obtained from anergic cells, in pg/ml.

|  | no. clones | IL-2 | IL-4 | IL-5 | IL-10 | IFN-γ | TNF-α |
|---|---|---|---|---|---|---|---|
| Anergic |  |  |  |  |  |  |  |
| Th3 | 15 | 10 | 10 | 1070 | 12290 | 3870 | 5950 |
| Th0 | 5 | 530 | 2270 | 6120 | 660 | 1990 | 2340 |
| Th2 | 5 | 10 | 3250 | 13690 | 1340 | 350 | 1140 |
| Th1 | 5 | 520 | 10 | 80 | 790 | 6330 | 6310 |
| Control |  |  |  |  |  |  |  |
| Th0 | 5 | 490 | 2900 | 11240 | 850 | 2656 | 4210 |
| Th2 | 5 | 10 | 4890 | 22210 | 1690 | 440 | 520 |
| Th1 | 5 | 470 | 10 | 10 | 470 | 3040 | 2120 |

FIG. 18 shows that IL-10 production by Th3 clones occurs rapidly after activation of the cells.

Example 9
Human Th3 Cell Clones Isolation of Purified CD4$^+$ T Cells

Peripheral blood mononuclear cells were prepared by centrifugation over Ficoll-hypaque. CD4$^+$ T cells were purified by negative selection. Negative purification was performed using a cocktail of antibodies directed against non-CD4$^+$ T cells: CD8, CD14, CD16, CD19, CD20, CD56, HLA-DR. Cells were incubated with saturating amounts of antibodies for 20 min at 4° C. After washing, Dynabeads (Dynal, Norway) were added at a ratio of 10 beads/target cell

TABLE 6

Cytokine profile upon restimulation with anti-CD3 mAbs of anergic cells

|  |  | cpm | IL-2 pg/ml | IL-4 pg/ml | IL-5 pg/ml | IL-10 pg/ml | TNF-α ng/ml | IFN-γ ng/ml | GM-CSF pg/ml |
|---|---|---|---|---|---|---|---|---|---|
| CD3 10 μg/ml | control cells | 42,369 | 875 ± 59 | <40 | 80 ± 23 | 1067 ± 226 | 10.5 ± 0.9 | 5.5 ± 0.6 | 1245 + 687 |
|  | anergic cells | 2,635 | <40 | <40 | <20 | <40 | <20 | <40 | <40 |
| CD3 700 μg/ml | control cells | 75,236 | 1045 + 105 | <40 | 107 ± 39 | 1145 ± 321 | 11.2 ± 1.3 | 4.3 ± 1.2 | 1569 ± 537 |
|  | anergic cells | 24,569 | 321 ± 65 | <40 | 445 ± 51 | 6421 ± 547 | 9.5 ± 0.8 | 1.6 ± 0.4 | 1125 ± 327 |

Cells (2.5 × 10$^6$ cells/ml) were stimulated with crosslinked anti-CD3 mAb (100 ng/ml) in the presence (anergic cells) or absence (control cells) of IL-10 (100 U/ml). After 10 days, cells were collected, layered over a Ficoll-Hypaque gradient, washed 3 times, and restimulated at 2.5 × 10$^5$ cells/ml with crosslinked CD3 mAb (either 10 μg/ml or 700 μg/ml). Twenty-four hours later, supernatants were collected and cytokine amounts were measured by ELISA. Results are mean ± SD of multiple measurements of one representative experiment.

FIG. 17 shows the proliferative responses of Th3 clones as compared to those of Th1 and Th2 clones.

Table 7 shows the cytokine production profile of Th3, Th0, Th1, and Th2 clones obtained from anergic cell populations of 2 different donors. The various T-cell clones were collected 12 days after stimulation with an irradiated feeder cell mixture+PMA and restimulated by a mixture of anti-CD3 and anti-CD28 mAbs for 24 hrs. Cytokine production (mean±SD) is expressed as pg/10$^6$ cells/ml. The characteristic cytokine production profile of Th3 clones is shown: no significant production of IL-2 and IL-4, but very high levels of IL-10 production. In addition, these cells produce IL-5 and IFN-γ and TNF-α. This cytokine production profile is clearly different from that of the Th0, Th1, and Th2 clones and incubated for 1 hr at 4° C. Beads and contaminating cells were removed by magnetic field. The remaining cells were resuspended with the same amount of beads and a second incubation period for 1 hr at 4° C. was performed. After removing contaminating cells, CD4$^+$ T cells were analyzed by FACScan (Becton Dickinson, Montain View, Calif.) and revealed to be more than 90–95% positive. In some experiments, CD4$^+$ T were purified by positive selection using magnetic beads directly coated with CD4 mAbs, according to the manufacturer's instructions (Dynal, Norway). With this procedure cells were more than 95% pure.

Culture Conditions

In these assays, cells were cultured in Yssel's medium supplemented with 10% FCS and 1% human serum.

For crosslinked anti-CD3 mAbs activation, 100 μg/ml (for cloning anergic cells) or 500 ng/ml (for induction of anergy) of anti-CD3 mAbs (SPV-T3) diluted in 0.1 M Tris buffer, pH 9.5, was incubated for a week at 4° C. in flat bottom 96 wells plates. Then, the plates are washed three times with RPMI.

Induction of Anergy and Cloning

To induce anergy, CD4+ T cells were cultured at $2.5 \times 10^5$ cells/ml in 24 well plates (Linbro, ICN Biomedical, Ohio) and activated with crosslinked anti-CD3 mabs in the presence of IL-10 (100 U/ml). After 10 days, cells were collected, layered on a Ficoll-hypaque gradient to remove dead cells, washed twice, and cloned at 0.3 cells/well. End point dilution cloning was performed by diluting anergic cells in feeder ($5 \times 10^5$ PBMC+$5 \times 10^4$ EBV transformed B cells (JY)) plus 2 U/ml of IL-2 on plates previously coated with 100 μg/ml of anti-CD3 mAbs. After 10 days, fresh medium, containing 2 U/ml of IL-2 was added in each well. Every 3 weeks, all wells were reactivated with feeders ($10^6$ PBMC+$10^5$ EBV-LCL)+PHA (10 μg/ml)+IL-2 (2U/ml). After 5–8 weeks, cells that grow out were transferred in 48 well plates and then to 24 well plates.

Maintenance of Th3 Cells

T cell clones were stimulated every 3 weeks with feeders ($10^6$ PBMC+$10^5$ EBV-LCL)+PHA (10 μg/ml)+IL-2 (2 U/ml). Every 3 days cells were checked, split if necessary, and fresh medium containing 2 U/ml of IL-2 was added.

Thus, the present invention provides Th3 cells, purified to homogeneity, e.g., in a clonal form, or populations comprising Th3 cells at high levels, including at least about 40%, generally at least about 50%, typically at least about 60%, more typically at least about 70%, preferably at least about 80%, more preferably at least about 90%, and in especially preferred embodiments, at least about 95% or higher purity of Th3 type cells.

Applicants have deposited separate cultures of *E. coli* MC1061 carrying pH5C, pH15C, and pBCRF1(SRα) with the American Type Culture Collection, Rockville, Md., USA (ATCC), on Dec. 20, 1989, under accession numbers 68191, 68192, and 68193, respectively. These deposits were made under conditions as provided under ATCC's agreement for Culture Deposit for Patent Purposes, which assures that, the deposit will be made available to the U.S. Commissioner of Patents and Trademarks pursuant to 35 U.S.C. §122 and 37 C.F.R. §1.14, and will be made available to the public upon issue of a U.S. patent, which requires that the deposit be maintained. Availability of the deposited strain is not to be construed as a license to practice the invention in contravention of the rights granted under the authority of any government in accordance with its patent laws.

The descriptions of the foregoing embodiments of the invention have been presented for purpose of illustration and description. They are not intended to be exhaustive or to limit the invention to the precise forms disclosed, and obviously many modifications and variations are possible in light of the above teaching. The embodiments were chosen and described in order to best explain the principles of the invention to thereby enable others skilled in the art to utilize the invention in various embodiments and with various modifications as are suited to the particular use contemplated. It is intended that the scope of the invention be defined by the claims appended hereto.

What is claimed is:

1. A composition comprising T cells that exhibit anergy for a specified antigen, wherein the antigen is an alloantigen, a bacterial antigen, a parasitic antigen or an allergen, wherein at least 40% of the T cells in the composition are T cells that exhibit anergy for the specified antigen, wherein said composition is produced by a process comprising contacting a population of T cells with both the antigen and exogenous IL-10 for at least about 5 days.

2. The composition of claim 1 wherein the population of T cells is from human blood.

3. The composition of claim 1 wherein the population of T cells is contacted with IL-10 for at least about 7 days.

4. The composition of claim 1 wherein the population of T cells is contacted with antigen for at least about 7 days.

5. The composition of claim 1 wherein said T cells that exhibit anergy for a specified antigen are derived from a single clone.

6. The composition of claim 1, wherein said exogenous IL-10 is human.

7. The composition of claim 1, wherein said antigen is an MHC polypeptide.

8. The composition of claim 1 that is a clonal population of T cells.

9. A composition comprising T cells that are anergic for an allogeneic monocyte antigen, wherein said composition is produced by a process comprising contacting a population of T cells with allogenic monocytes and exogenous IL-10.

10. The composition of claim 9 wherein the population of T cells is from peripheral blood.

11. The composition of claim 10 wherein the population of T cells is contacted with allogeneic monocytes and IL-10 for at least 5 days.

12. The composition of claim 9, wherein said exogenous IL-10 is human.

13. A method of producing a composition comprising T cells that are anergic for an allogeneic monocyte antigen, wherein said composition is produced by a process comprising contacting a population of T cells with allogeneic monocytes and exogenous IL-10.

14. The method of claim 13 wherein the population of T cells are from peripheral blood.

15. The method of claim 13 wherein the population of T cells is contacted with allogeneic monocytes and IL-10 for at least 5 days.

16. The method of claim 13, wherein said exogenous IL-10 is human.

17. A T cell that exhibits anergy for an MHC antigen, wherein said T cell is produced by contacting a precursor of said T cell with exogenous IL-10 together with said antigen for at least 3 days, and wherein said T cell is characterized by producing at least about 5-times more IL-10 when stimulated with an anti-CD3 antibody than does a Th2 cell stimulated with an anti-CD3 antibody.

* * * * *

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 178 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

```
Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
                20                  25                  30

Phe Pro Gly Asn Leu Pro Asn Met Leu Arg Asp Leu Arg Asp Ala Phe
            35                  40                  45

Ser Arg Val Lys Thr Phe Phe Gln Met Lys Asp Gln Leu Asp Asn Leu
        50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
```

-continued

```
                    100                 105                 110
Gly Glu Asn Leu Lys Thr Leu Arg Leu Arg Leu Arg Arg Cys His Arg
                115                 120                 125
Phe Leu Pro Cys Glu Asn Lys Ser Lys Ala Val Glu Gln Val Lys Asn
            130                 135                 140
Ala Phe Asn Lys Leu Gln Glu Lys Gly Ile Tyr Lys Ala Met Ser Glu
145                 150                 155                 160
Phe Asp Ile Phe Ile Asn Tyr Ile Glu Ala Tyr Met Thr Met Lys Ile
                165                 170                 175
Arg Asn
```

(2) INFORMATION FOR SEQ ID NO:2:

(i) SEQUENCE CHARACTERISTICS:
        (A) LENGTH: 170 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Met Glu Arg Arg Leu Val Val Thr Leu Gln Cys Leu Val Leu Leu Tyr
1               5                   10                  15
Leu Ala Pro Glu Cys Gly Gly Thr Asp Gln Cys Asp Asn Phe Pro Gln
                20                  25                  30
Met Leu Arg Asp Leu Arg Asp Ala Phe Ser Arg Val Lys Thr Phe Phe
                35                  40                  45
Gln Thr Lys Asp Glu Val Asp Asn Leu Leu Leu Lys Glu Ser Leu Leu
            50                  55                  60
Glu Asp Phe Lys Gly Tyr Leu Gly Cys Gln Ala Leu Ser Glu Met Ile
65                  70                  75                  80
Gln Phe Tyr Leu Glu Glu Val Met Pro Gln Ala Glu Asn Gln Asp Pro
                85                  90                  95
Glu Ala Lys Asp His Val Asn Ser Leu Gly Glu Asn Leu Lys Thr Leu
                100                 105                 110
Arg Leu Arg Leu Arg Arg Cys His Arg Phe Leu Pro Cys Glu Asn Lys
                115                 120                 125
Ser Lys Ala Val Glu Gln Ile Lys Asn Ala Phe Asn Lys Leu Gln Glu
            130                 135                 140
Lys Gly Ile Tyr Lys Ala Met Ser Glu Phe Asp Ile Phe Ile Asn Tyr
145                 150                 155                 160
Ile Glu Ala Tyr Met Thr Ile Lys Ala Arg
                165                 170
```

(2) INFORMATION FOR SEQ ID NO:3:

(i) SEQUENCE CHARACTERISTICS:
        (A) LENGTH: 160 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Ser Pro Gly Gln Gly Thr Gln Ser Glu Asn Ser Cys Thr His Phe Pro
1               5                   10                  15
Gly Asn Leu Pro Asn Met Leu Arg Asp Leu Arg Asp Ala Phe Ser Arg
```

```
                  20                  25                  30
Val Lys Thr Phe Phe Gln Met Lys Asp Gln Leu Asp Asn Leu Leu Leu
                 35                  40                  45
Lys Glu Ser Leu Leu Glu Asp Phe Lys Gly Tyr Leu Gly Cys Gln Ala
 50                  55                  60
Leu Ser Glu Met Ile Gln Phe Tyr Leu Glu Glu Val Met Pro Gln Ala
 65                  70                  75                  80
Glu Asn Gln Asp Pro Asp Ile Lys Ala His Val Asn Ser Leu Gly Glu
                 85                  90                  95
Asn Leu Lys Thr Leu Arg Leu Arg Leu Arg Arg Cys His Arg Phe Leu
                 100                 105                 110
Pro Cys Glu Asn Lys Ser Lys Ala Val Glu Gln Val Lys Asn Ala Phe
                 115                 120                 125
Asn Lys Leu Gln Glu Lys Gly Ile Tyr Lys Ala Met Ser Glu Phe Asp
                 130                 135                 140
Ile Phe Ile Asn Tyr Ile Glu Ala Tyr Met Thr Met Lys Ile Arg Asn
145                 150                 155                 160

(2) INFORMATION FOR SEQ ID NO:4:

(i) SEQUENCE CHARACTERISTICS:
         (A) LENGTH: 147 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:4:

Thr Asp Gln Cys Asp Asn Phe Pro Gln Met Leu Arg Asp Leu Arg Asp
 1                   5                  10                  15
Ala Phe Ser Arg Val Lys Thr Phe Phe Gln Thr Lys Asp Glu Val Asp
                 20                  25                  30
Asn Leu Leu Leu Lys Glu Ser Leu Leu Glu Asp Phe Lys Gly Tyr Leu
                 35                  40                  45
Gly Cys Gln Ala Leu Ser Glu Met Ile Gln Phe Tyr Leu Glu Glu Val
 50                  55                  60
Met Pro Gln Ala Glu Asn Gln Asp Pro Asp Ala Lys Asp His Val Asn
 65                  70                  75                  80
Ser Leu Gly Glu Asn Leu Lys Thr Leu Arg Leu Arg Leu Arg Arg Cys
                 85                  90                  95
His Arg Phe Leu Pro Cys Glu Asn Lys Ser Lys Ala Val Glu Gln Ile
                 100                 105                 110
Lys Asn Ala Phe Asn Lys Leu Gln Glu Lys Gly Ile Tyr Lys Ala Met
                 115                 120                 125
Ser Glu Phe Asp Ile Phe Ile Asn Tyr Ile Glu Ala Tyr Met Thr Ile
                 130                 135                 140
Lys Ala Arg
145

(2) INFORMATION FOR SEQ ID NO:5:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (ii) MOLECULE TYPE: cDNA
```

(xi) SEQUENCE DESCRIPTION: SEQ ID NO:5:

CTAAGGAGGT TTAAC                                                         15

(2) INFORMATION FOR SEQ ID NO:6:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:6:

ATGAGCTCAT                                                               10

(2) INFORMATION FOR SEQ ID NO:7:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:7:

AGCCCAGGCC AGGGCACCCA GTCTGAGAAC AGCTGCACCC ACTTCCCAGG TAACCGGTAC         60

(2) INFORMATION FOR SEQ ID NO:8:

(i) SEQUENCE CHARACTERISTICS:
            (A) LENGTH: 56 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:8:

CGGTTACCTG GGAAGTGGGT GCAGCTGTTC TCAGACTGGG TGCCCTGGCC TGGGCT            56

(2) INFORMATION FOR SEQ ID NO:9:

(i) SEQUENCE CHARACTERISTICS:
            (A) LENGTH: 62 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:9:

GTAACCTGCC TAACATGCTT CGAGATCTCC GAGATGCCTT CAGCAGAGTG AAGACTTTCT         60
TT                                                                       62

(2) INFORMATION FOR SEQ ID NO:10:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:10:

CTTCACTCTG CTGAAGGCAT CTCGGAGATC TCGAAGCATG TTAGGCAG                48

(2) INFORMATION FOR SEQ ID NO:11:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

CAAATGAAGG ATCAGCTGGA CAACTTGTTC TTAAG                              35

(2) INFORMATION FOR SEQ ID NO:12:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

CTTAAGAACA AGTTGTCCAG CTGATCCTTC ATTTGAAAGA AAGT                    44

(2) INFORMATION FOR SEQ ID NO:13:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

GAGTCCTTGC TGGAGGACTT TAAGGGTTAC CTGGGTTGCC AAGCCTTGTC TGAGATGATC    60

CAGTTTTAT                                                          69

(2) INFORMATION FOR SEQ ID NO:14:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GATCATCTCA GACAAGGCTT GGCAACCCAG GTAACCCTTA AAGTCCTCCA GCAAGGACTC    60

CTAGATAAAA CTG                                                     73

(2) INFORMATION FOR SEQ ID NO:15:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

```
CTAGAGGAGG TGATGCCCCA AGCTGAGAAC CAAGACCCAG ACATCAAGGC GCATGTTAAC        60

G                                                                       61
```

(2) INFORMATION FOR SEQ ID NO:16:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

```
GTTAACATGC GCCTTGATGT CTGGGTCTTG GTTCTCAGCT TGGGGCATCA CCTCCTCTAG        60

TCGAC                                                                   65
```

(2) INFORMATION FOR SEQ ID NO:17:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

```
AACTCCCTGG GGGAGAACCT GAAGACCCTC AGGCTGAGGC TACGGCGCTG TCATCGATCT        60

GCA                                                                     63
```

(2) INFORMATION FOR SEQ ID NO:18:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

```
GATCGATGAC AGCGCCGTAG CCTCAGCCTG AGGGTCTTCA GGTTCTCCCC CAGGGAGTT         59
```

(2) INFORMATION FOR SEQ ID NO:19:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

```
CGATTTCTTC CCTGTCAAAA CAAGAGCAAG GCCGTGGAGC AGGTGAAGAA CGCGTGCATG        60
```

(2) INFORMATION FOR SEQ ID NO:20:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

CACGCGTTCT TCACCTGCTC CACGGCCTTG CTCTTGTTTT GACAGGGAAG AAAT          54

(2) INFORMATION FOR SEQ ID NO:21:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

CGCGTTTAAT AATAAGCTCC AAGACAAAGG CATCTACAAA GCCATGAGTG AGTTTGAC      58

(2) INFORMATION FOR SEQ ID NO:22:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

ACTCATGGCT TTGTAGATGC CTTTGTCTTG GAGCTTATTA TTAAA                    45

(2) INFORMATION FOR SEQ ID NO:23:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

ATCTTCATCA ACTACATAGA AGCCTACATG ACAATGAAGA TACGAAACTG A             51

(2) INFORMATION FOR SEQ ID NO:24:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

AGCTTCAGTT TCGTATCTTC ATTGTCATGT AGGCTTCTAT GTAGTTGATG AAGATGTCAA    60

ACTC                                                                64

(2) INFORMATION FOR SEQ ID NO:25:

(i) SEQUENCE CHARACTERISTICS:
        (A) LENGTH: 498 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

```
AATTCATGGA GCGAAGGTTA GTGGTCACTC TGCAGTGCCT GGTGCTGCTT TACCTGGCAC          60

CTGAGTGTGG AGGTACAGAC CAATGTGACA ATTTTCCCCA GACCTAAGAG ATGCCTTCAG         120

TCGTGTTAAA ACCTTTTTCC AGACAAAGGA CGAGGTAGAT AACCTTTTGC TCAAGGAGTC         180

TCTGCTAGAG GACTTTAAGG ATGCCAGGCC CTGTCAGAAA TGATCCAATT CTACCTGGAG         240

GAAGTCATGC CACAGGCTGA AACCAGGACC CTGAAGCCAA AGACCATGTC AATTCTTTGG         300

GTGAAAATCT AAAGACCCTA CGGCTCCGCC TGCGCAGGTG CCACAGGTTC CTGCCGTGTG         360

AGAACAAGAG TAAAGCTGTG GAACAGATAA AAAATGCCTT TAACAAGCTG CAGGAAAAAG         420

GAATTTACAA AGCCATGAGT GAATTTGACA TTTTTATTAA CTACATAGAA GCATACATGA         480

CAATTAAAGC CAGGTGAG                                                       498

(2) INFORMATION FOR SEQ ID NO:26:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

GAATTCCCAG GTTTAACGTA AGGAGGTTTA ACCATCGATG                                40
```